(12) United States Patent
Liu et al.

(10) Patent No.: US 12,378,328 B2
(45) Date of Patent: Aug. 5, 2025

(54) BIOHYBRID PEPTIDOGLYCAN OLIGOMERS

(71) Applicants: Nanyang Technological University, Singapore (SG); National University of Singapore, Singapore (SG)

(72) Inventors: Xuewei Liu, Singapore (SG); Bee Eng Mary Chan, Singapore (SG); Hongwei Duan, Singapore (SG); Jingxi He, Singapore (SG); Kim Le Mai Hoang, Singapore (SG); Liang Yang, Singapore (SG)

(73) Assignees: Nanyang Technological University, Singapore (SG); National University of Singapore, Singapore (SG)

( * ) Notice: Subject to any disclaimer, the term of this patent is extended or adjusted under 35 U.S.C. 154(b) by 374 days.

(21) Appl. No.: 17/267,271

(22) PCT Filed: Sep. 19, 2019

(86) PCT No.: PCT/SG2019/050473
§ 371 (c)(1),
(2) Date: Feb. 9, 2021

(87) PCT Pub. No.: WO2020/060491
PCT Pub. Date: Mar. 26, 2020

(65) Prior Publication Data
US 2022/0213232 A1 Jul. 7, 2022

(30) Foreign Application Priority Data
Sep. 18, 2019 (SG) .......................... 10201808123Y

(51) Int. Cl.
| | |
|---|---|
| *C08B 37/00* | (2006.01) |
| *A61K 47/54* | (2017.01) |
| *A61K 47/61* | (2017.01) |
| *A61K 47/64* | (2017.01) |
| *A61P 31/04* | (2006.01) |
| *C08B 37/08* | (2006.01) |
| *C12Q 1/18* | (2006.01) |

(52) U.S. Cl.
CPC .......... *C08B 37/003* (2013.01); *A61K 47/542* (2017.08); *A61K 47/61* (2017.08); *A61K 47/64* (2017.08); *A61P 31/04* (2018.01); *C12Q 1/18* (2013.01)

(58) Field of Classification Search
None
See application file for complete search history.

(56) References Cited

U.S. PATENT DOCUMENTS

2018/0201652 A1 7/2018 Chan et al.

FOREIGN PATENT DOCUMENTS

WO 2006113792 A2 10/2006

OTHER PUBLICATIONS

Vollmer, Waldemar, Didier Blanot, and Miguel A. De Pedro. "Peptidoglycan structure and architecture." FEMS microbiology reviews 32.2 (2008): 149-167.*
Hou, Zheng, et al. "Nanoparticles of short cationic peptidopolysaccharide self-assembled by hydrogen bonding with antibacterial effect against multidrug-resistant bacteria." ACS applied materials & interfaces 9.44 (2017): 38288-38303.*
Welzel; Syntheses around the Transglycosylation Step in Peptidoglycan Biosynthesis; Chem. Rev. 105, 4610-4660 (2005).
Lee; Synthetic Efforts in Preparations of Components of the Bacterial Cell Wall in Chemical Glycobiology; vol. 990 54-78 (American Chemical Society, 2008).
Lebar et al., Forming Cross-Linked Peptidoglycan from Synthetic Gram-Negative Lipid II. J. Am. Chem. Soc. 135, 4632-4635 (2013).
Lee et al.; From Genome to Proteome to Elucidation of Reactions for All Eleven Known Lytic Transglycosylases from Pseudomonas aeruginosa; Angew; Chem. Int. Ed. 56, 2735-2739 (2017).
Wang et al.; Synthesis of Peptidoglycan Fragments from Enterococcus faecalis with Fmoc-Strategy for Glycan Elongation. Chem. Asian J. 12, 27-30 (2017).
Ye et al.; Better Substrates for Bacterial Transglycosylases. J. Am. Chem. Soc. 123, 3155-3156 (2001).
Liu et al.; Acceptor Specificity and Inhibition of the Bacterial Cell-Wall Glycosyltransferase MurG. ChemBioChem 4, 603-609 (2003).
Cho et al.; Structural insights into the bactericidal mechanism of human peptidoglycan recognition proteins. Proc. Natl. Acad. Sci. USA 104, 8761-8766 (2007).
Shih et al.; Effect of the Peptide Moiety of Lipid II on Bacterial Transglycosylase; Angew; Chem. Int. Ed. 51, 10123-10126 (2012).
Zhang et al.; Synthesis of Heptaprenyl?Lipid IV to Analyze Peptidoglycan Glycosyltransferases. J. Am. Chem. Soc. 129, 3080-3081 (2007).
Wang et al., Primer Preactivation of Peptidoglycan Polymerases. J. Am. Chem. Soc. 133, 8528-8530 (2011).
Qiao et al., Detection of Lipid-Linked Peptidoglycan Precursors by Exploiting an Unexpected Transpeptidase Reaction. J. Am. Chem. Soc. 136, 14678-14681 (2014).
Liang et al., Metabolic labelling of the carbohydrate core in bacterial peptidoglycan and its applications. Nat. Commun. 8, 15015 (2017).

(Continued)

*Primary Examiner* — Patrick T Lewis
(74) *Attorney, Agent, or Firm* — Patterson + Sheridan, LLP

(57) ABSTRACT

The invention relates to a compound of formula Ia and/or formula Ib: or a pharmaceutically acceptable salt, solvate or prodrug thereof, where the groups are defined herein. The invention also relates to a pharmaceutical formulation comprising the compound for treating or detecting a microbial infection in a subject, a method of determining antimicrobial resistance of a microbial infection using the compound, and a method of determining an effective dose of one or more antimicrobial agents to kill a microorganism using the compound.

20 Claims, 16 Drawing Sheets

(56) References Cited

OTHER PUBLICATIONS

Figure 1:
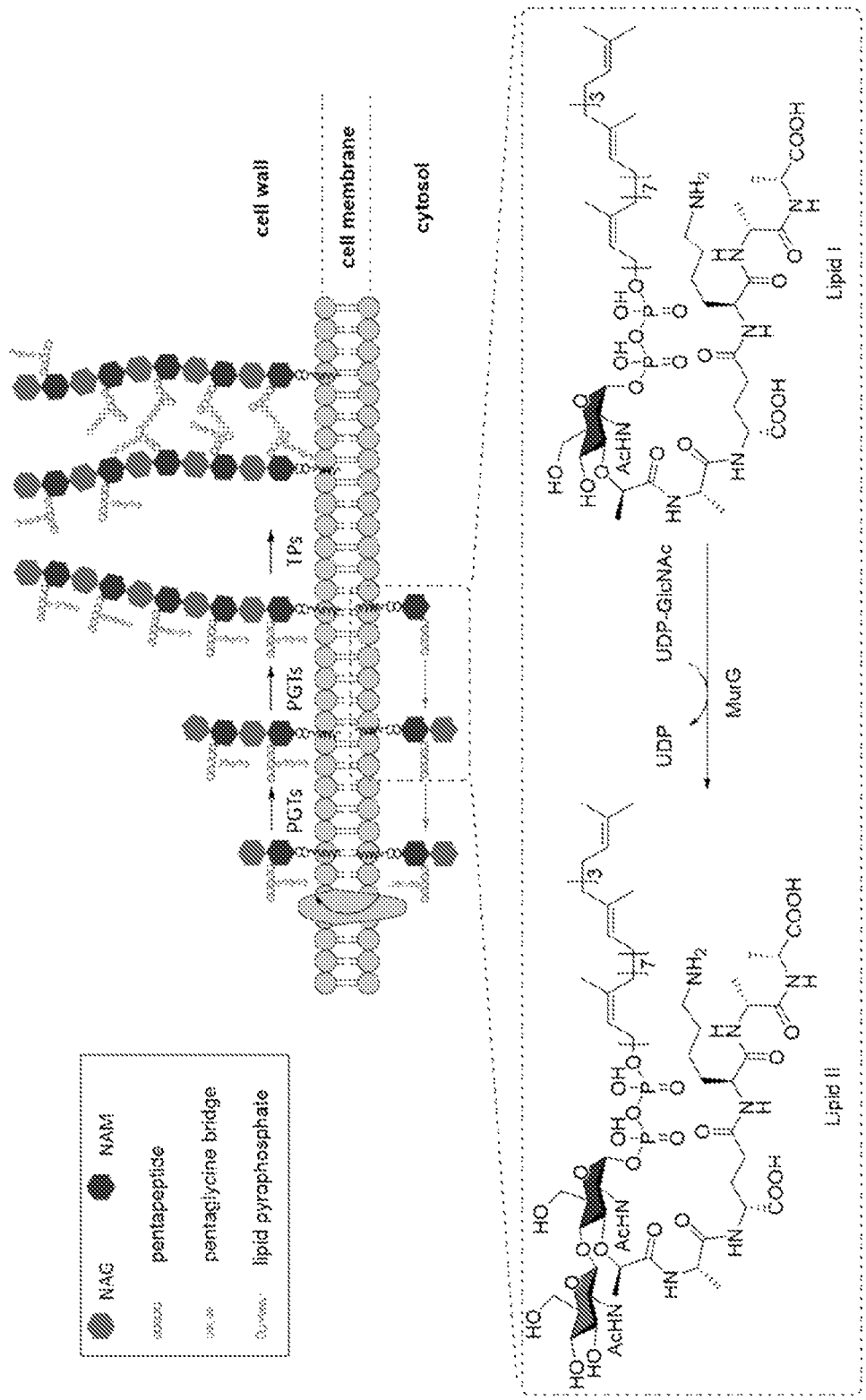

Pidgeon et al., Metabolic Profiling of Bacteria by Unnatural C-terminated D-Amino Acids. Angew. Chem. Int. Ed. 54, 6158-6162 (2015).
Vollmer et al., Peptidoglycan structure and architecture. FEMS Microbiol. Rev. 32, 149-167 (2008).
Langer; New Methods of Drug Delivery; Science (1990) 249, 1527.
Ifuku et al.I Preparation of highly chemoselective N-phthaloyl chitosan in aqueous media. Green Chem. 13, 1499-1502 (2011).
Binette et al.; Regioselective Silylation of N-Phthaloylchitosan with TBDMS and TBDPS Groups. Biomacromolecules 8, 1812-1815 (2007).
Lupoli et al.; Transpeptidase-Mediated Incorporation of d-Amino Acids into Bacterial Peptidoglycan. J. Am. Chem. Soc. 133, 10748-10751 (2011).
Hermanson; Chapter 10—Fluorescent Probes in Bioconjugate Techniques (Third edition) 395-463 (Academic Press, Boston, 2013).
Burgess et al., Loss of human Greatwall results in G2 arrest and multiple mitotic defects due to deregulation of the cyclin B-Cdc2/PP2A balance. Proc. Natl. Acad. Sci. USA 107, 12564-12569 (2010).
McCloy et al.; Partial inhibition of Cdk1 in G2 phase overrides the SAC and decouples mitotic events. Cell Cycle 13, 1400-1412 (2014).
Huang et al.; Crystal structure of *Staphylococcus aureus* transglycosylase in complex with a lipid II analog and elucidation of peptidoglycan synthesis mechanism. Proc. Natl. Acad. Sci. USA 109, 6496-6501 (2012).
Chang et al.; High frequency transformation of Bacillus subtilis protoplasts by plasmid DNA. Molec. Gen. Genet. 168, 111-115 (1979).
Hakenbeck et al.; ?- Lactam resistance in *Streptococcus pneumoniae*: penicillin-binding proteins and non-penicillin-binding proteins. Mol. Microbiol. 33, 673-678 (1999).
Boneca et al.; Vancomycin resistance: occurrence, mechanisms and strategies to combat it. Expert Opin. Ther. Targets 7, 311-328 (2003).
Waxman et al.; Penicillin-Binding Proteins and the Mechanism of Action of Beta-Lactam Antibiotics. Annu. Rev. Biochem. 52, 825-869 (1983).
Holtje; Growth of the stress-bearing and shape-maintaining murein sacculus of *Escherichia coli*. Microbiol. Mol. Biol. Rev. 62, 181-203 (1998).
Wong et al.; Peptidoglycan biosynthesis—Unexploited antibacterial targets within a familiar pathway. Adv. Exp. Med. Biol. 456, 197-217 (1998).
Typas et al., From the regulation of peptidoglycan synthesis to bacterial growth and morphology. Nat. Rev. Microbiol. 10, 123-136 (2012).
Schneider et al.; Plectasin, a Fungal Defensin, Targets the Bacterial Cell Wall Precursor Lipid II. Science 328, 1168-1172 (2010).
Ling et al.; A new antibiotic kills pathogens without detectable resistance. Nature 517, 455-459 (2015).
Kuru et al. In Situ Probing of Newly Synthesized Peptidoglycan in Live Bacteria with Fluorescent D-Amino Acids. Angew. Chem. Int. Ed. 51, 12519-12523 (2012).
Bugg; Biosynthesis Imaging cell-wall biosynthesis live. Nat. Chem. 5, 10-12 (2013).
Siegrist et al.; D-Amino Acid Chemical Reporters Reveal Peptidoglycan Dynamics of an Intracellular Pathogen. ACS Chem. Biol. 8, 500-505 (2013).
Sarkar et al.; In Vivo Probe of Lipid II-Interacting Proteins; Angew; Chem. Int. Ed. 55, 8401-8404 (2016).
Lebar et al.; Reconstitution of Peptidoglycan Cross-Linking Leads to Improved Fluorescent Probes of Cell Wall Synthesis. J. Am. Chem. Soc. 136, 10874-10877 (2014).
Sadamoto et al., Cell-Wall Engineering of Living Bacteria. J. Am. Chem. Soc. 2002, 124 (31), 9018-9019.
Silhavy et al.; The Bacterial Cell Envelope; Cold Spring Harb Perspect Biol. 2010, 2(5):a000414 doi: 10.1101/cshperspect. a000414.
Lee et al; The Mechanism of Action of Lysobactin; Am. Chem. Soc. 2016, 138 (1), 100-103.
Vannieuwenhze et al.; The First Total Synthesis of Lipid II: The Final Monomeric Intermediate in Bacterial Cell Wall Biosynthesis Am. Chem. Soc. 2002, 124 (14), 3656-3660.
Gampe et al.; Modular synthesis of diphospholipid oligosaccharide fragments of the bacterial cell wall and their use to study the mechanism of moenomycin and other antibiotics; Tetrahedron 67 (2011) 9771-9778.
Derouaux et al.; Peptidoglycan glycosyltransferase substrate mimics as templates for the design of new antibacterial drugs; Front. Immunol. 2013, 4, 1-6.
International Search Report and Written Opinion in related application PCT/SG2019/050473 dated Dec. 12, 2019.
Huang, L.-Y. et al., Enzymatic synthesis of lipid II and analogues. Angew Chem Int Ed, Jul. 2, 2014, vol. 53, No. 31, pp. 8060-8065 [Retrieved on Dec. 4, 2019] <DOI: 10.1002/ANIE.201402313 Figure 2 compound 7, Figure 3; Supporting Information pp. 1-30.
Dumbre, S. et al., Synthesis of Modified Peptidoglycan Precursor Analogues for the Inhibition of Glycosyltransferase. J. Am. Chem. Soc., May 2, 2012, vol. 134, No. 22, pp. 9343-9351 [Retrieved on Dec. 4, 2019] <DOI: 10.1021 /JA302099U> Figure 1, Figure 2 compound 1, Table 2, and Supporting Information pp. 1-216,.
Kuru, E. et al., Synthesis of fluorescent d-amino acids and their use for probing peptidoglycan synthesis and bacterial growth in situ. Nature Protocols, Dec. 4, 2014, vol. 10, No. 1, pp. 33-52 [Retrieved on Dec. 4, 2019] <DOI: 10.1038/NPROT.2014.197> Figure 3, p. 35-36 Labeling strategies and applications.
Shih, H.-W. et al., A New Synthetic Approach toward Bacterial Transglycosylase Substrates, Lipid II and Lipid IV. Org. Lett., Jul. 28, 2011, vol. 13, No. 17, pp. 4600-4603 [Retrieved on Dec. 4, 2019] <DOI: 10.1021 /OL201806D> Scheme 3, Figure 3, p. S22-S23 section Transglycosylation reaction of *E. coli* PBP1 b TGase with NBD-Lipid IV and Lipid II in the supporting document.
Liu, H. et al., Characterization of a transglycosylase domain of *Streptococcus pneumoniae* PBP1 b. Bioorganic & Medicinal Chemistry, Jul. 5, 2006, vol. 14, No. 21, pp. 7187-7195 [Retrieved on Dec. 4, 2019] <DOI: 10.1016/J.BMC.2006.06.058> Figure 1.

\* cited by examiner

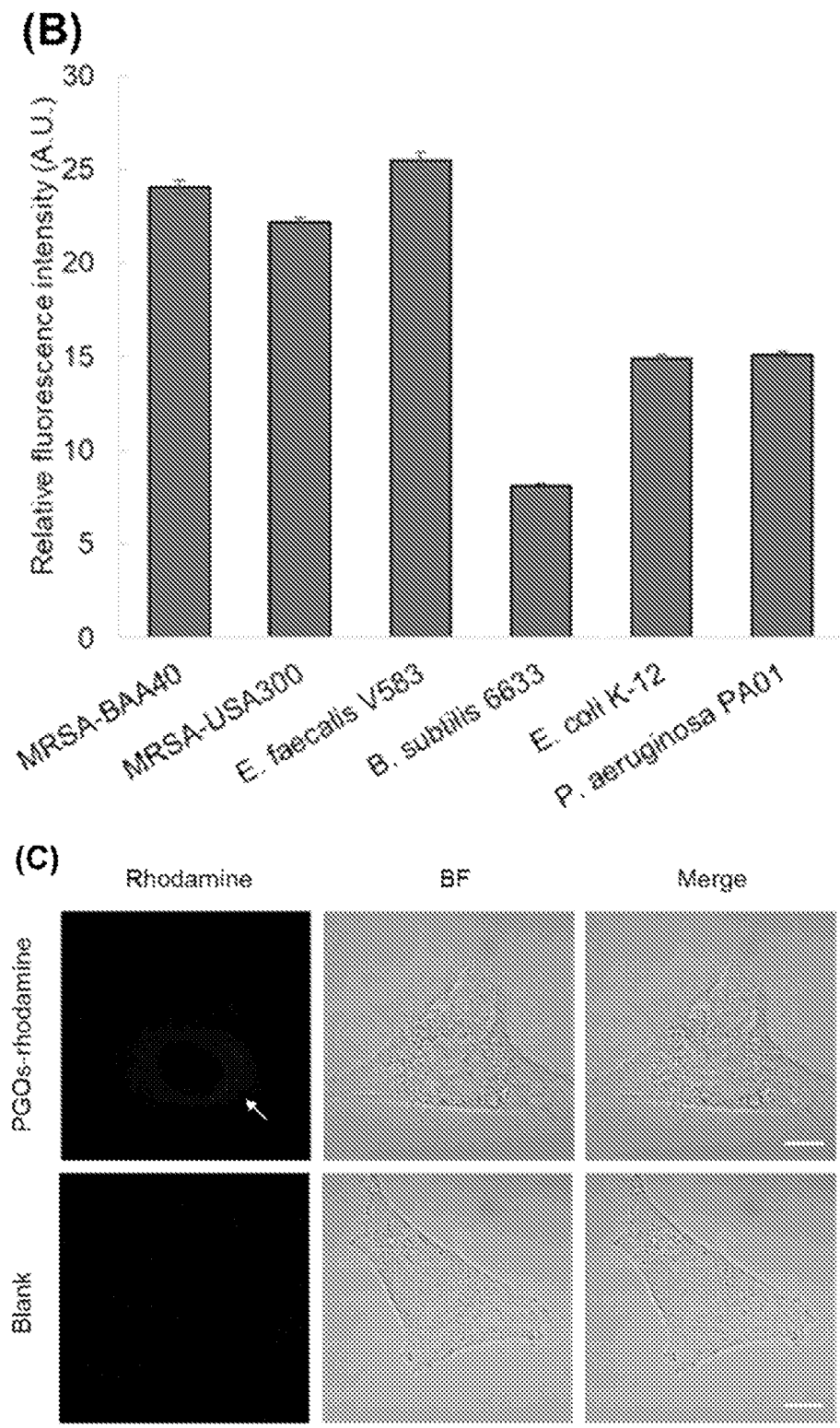
FIG. 4B-C

BIOHYBRID PEPTIDOGLYCAN OLIGOMERS

FIELD OF INVENTION

The invention relates to a compound and a pharmaceutical formulation comprising the compound, which can be for treating or detecting a microbial infection in a subject. The invention also relates to a method of determining antimicrobial resistance of a microbial infection using the compound, and a method of determining an effective dose of one or more antimicrobial agents to kill a microorganism using the compound.

BACKGROUND

The listing or discussion of a prior-published document in this specification should not necessarily be taken as an acknowledgement that the document is part of the state of the art or is common general knowledge.

The rise of multidrug-resistant bacteria pathogens is a global threat to public health, driving the search for new and more effective antibiotics. The biosynthetic pathway of bacterial cell walls remains an attractive drug target, due to its ubiquitous presence across all bacterial phyla and its complete absence in human cells. In fact, highly successful broad-spectrum antibiotics such as vancomycin, penicillin, and the associated beta-lactam families specifically disrupt various stages of bacterial cell wall biogenesis.

The major constituent of bacterial cell walls in both Gram-positive and Gram-negative bacteria is the network of peptidoglycan (PG). The PG network forms a resilient structure that protects bacteria against varying osmotic pressures, and provides an anchoring platform for extracytosolic proteins such as Braun's lipoprotein. At the molecular level, PG contains repeating units of N-acetyl-glucosamine (NAG) linked N-acetyl-muramic acid (NAM), with the latter covalently linked to a pendant pentapeptide. Different bacteria strains demonstrate variance in the exact structure of the pentapeptides, which are all cross-linked to the same NAG-NAM oligosaccharide chains to generate the three-dimensional network of PG that is characteristic of all bacterial cell walls.

NAG-NAM oligosaccharide elongation and peptide cross-linking are thus shared processes in all bacteria, mediated by a variety of peptidoglycan glycosyltransferases (PGTs) and transpeptidases (TPs) respectively. As shown in FIG. 1, MurG (MurG is the name of an enzyme which couples NAG and NAM for synthesis of Lipid II), a PGT, catalyzes the glycosylation reaction between UDP-GlcNAC, which contains NAG (UDP stands for uridine diphosphate), and the Lipid I substrate, which contains NAM and a pendant pentapeptide, to form the lipid-linked NAG-NAM β-(1,4) disaccharide known as Lipid II. After a pentaglycine bridge is added to Lipid II, it is translocated to the exterior surface of the cell membrane and incorporated into the peptidoglycan network by peptidoglycan glycosyltransferases (PGTs) to form peptidoglycan oligomers. Cross-linking by transpeptidases (TPs) completes peptidoglycan biosynthesis. Some TPs bind to penicillin, and are thus known as penicillin-binding proteins (PBPs).

TP enzymes have been the target for several modern broad-spectrum antibiotics such as penicillin and vancomycin. However, little is known about the PGTs and their enzymatic properties, in part due to the limited availability of both relevant substrates and appropriate in vitro assays. Towards this end, some encouraging efforts have been devoted to synthesizing the Lipid I-IV compounds as PGT substrates, through chemical or chemoenzymatic pathways (*Chem. Rev.*, 2005, 105, 4610-4660; *Chemical Glycobiology*, Vol. 990 54-78 (American Chemical Society, 2008); *J. Am. Chem. Soc.*, 2013, 135, 4632-4635; *Angew. Chem. Int. Ed.*, 2014, 53, 8060-8065; *Angew. Chem. Int. Ed.*, 2017, 56, 2735-2739; *Chem. Asian J.*, 2017, 12, 27-30). Through these substrates, invaluable information on PGT enzymatic properties have been gathered, and early attempts were made to chemically engineer the substrates into potential inhibitors for mechanistic studies, structure-activity relationship studies, and novel antibiotic designs (*J. Am. Chem. Soc.* 2011, 123, 3155-3156; *Chem Bio Chem*, 2003, 4, 603-609; *Proc. Natl. Acad. Sci. USA*, 2007, 104, 8761-8766; *Angew. Chem. Int. Ed.* 2012, 51, 10123-10126).

One of the major obstacles inhibiting further progress was the difficulty in obtaining the Lipid I-IV substrates. An overwhelming number of steps are required to obtain just the tetrasaccharide unit, reported at nearly 63 steps starting from monosaccharides (*Angew. Chem. Int. Ed.*, 2017, 56, 2735-2739), even though the tetrasaccharide is still suboptimal. Longer N-saccharide oligomers are likely to be more biologically relevant substrates for PGTs and TPs (FIG. 1) (*J. Am. Chem. Soc.* 2007, 129, 3080-3081; *Org. Lett.* 2011, 13, 4600-4603; *J. Am. Chem. Soc.* 2011, 133, 8528-8530).

Figure 13:
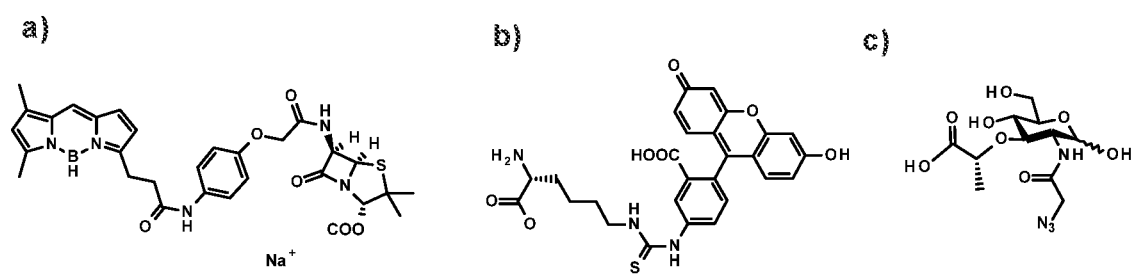

Three types of metabolic labeling agents for studying bacterial cell walls have been reported. They are fluorescence dyes which are conjugates of either antibiotic, D-amino acid or sugar (*J. Am. Chem. Soc.*, 2014, 136, 14678-14681; *Nat. Commun.* 2017, 8, 15015; see FIG. 13). Antibiotic conjugates are the most established labeling agents, being already commercialised by various companies. One example is penicillin V conjugate (BOCILLIN™ FL Penicillin; FIG. 13a). Such compounds bind to the enzymes responsible for peptidoglycan biosynthesis through inhibitory activities. Hence, the cells labelled by this mechanism are not viable for any follow-up assays, as it gives only a snapshot of the growth inhibited cells.

D-amino acid conjugates, such as carboxyfluorescein-conjugated lysine monomers (FIG. 13b), have been recently developed for metabolic labelling. They are added to cell wall by bacterial transpeptidases to replace the D-amino acids residing on peptide terminals. The incorporation of the conjugates leave the target cells unharmed, allowing for mechanistic studies of live cells based on fluorescence. However, the agents must reach the cell wall to be taken up by bacterial transpeptidases. It was shown that such a class of substrates showed inefficient uptake in Gram-negative species, possibly due to the presence of an outer membrane (*Angew. Chem. Int. Ed.*, 2015, 54, 6158-6162). In addition, D-amino acids encompass limited functionalities and binding sites and are thus significantly influenced by the deviations in binding pocket arrangement of each bacterial strain as their peptide sequence varies (*FEMS Microbiol. Rev.*, 2008, 32, 149-167).

Sugar conjugates (FIG. 13c) are the most recently developed agents for bringing fluorophores into bacterial cell walls. They are incorporated into cell walls through interaction with bacterial glycosyltransferases at an earlier stage of cell maturation. Hence, they are not blocked by the outer membrane found on Gram-negative species, and have a broader spectrum of application. However, the sugar itself did not demonstrate selective recognition for bacteria over mammalian cells, and so experiments involving mammalian cells had to be done in two steps—the ambient labelling agents must be cleared of bacteria before incubation with mammalian cells, or else fluorescence could be found in both species.

There is therefore a need for an efficient compound or substrate that solves one or more of the problems identified above.

SUMMARY OF INVENTION

In a first aspect of the invention, there is provided a compound of formula Ia and/or formula Ib:

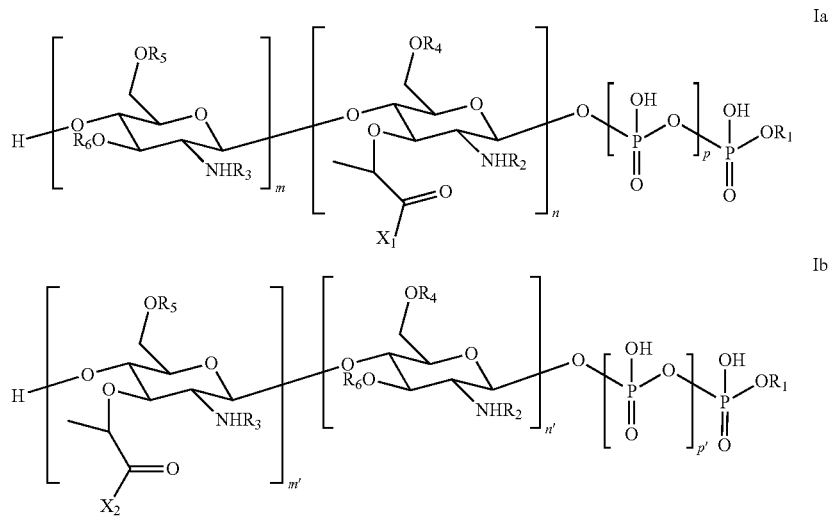

Ia

Ib wherein:
- $R_1$ represents $C_1$ to $C_{20}$ alkyl or —$CH_2CH(CO_2H)OC_{1-20}$ alkyl;
- $R_2$ and $R_3$ each independently represent —$C(=O)R_7$;
- $R_4$ to $R_6$ each represent H;
- each $R_7$ independently represents $C_1$ to $C_{20}$ alkyl;
- $X_1$ and $X_2$ independently represent -$AA_1$-$AA_2$-$AA_3$-$_D$-Ala-$AA_4$, where:
  - $AA_1$ is selected from $_L$-Ala, $_L$-Gly, $_D$-Gly or $_L$-Ser;
  - $AA_2$ is selected from $_D$-isoglutamate ($\gamma$-$_D$-glutamate, $\gamma$-$_D$-Glu), $_D$-isoglutamine, or threo-3-hydroxyglutamate
  - $AA_3$ is selected from $_L$-homoserine, $_D$-homoserine, $_D$-5-hydroxylysine, $_D$-Orn, $_L$-Lys, Lys, $_L$-Orn, $_L$-2,4-diaminobutyrate, or $_L$-5-hydroxylysine, where the amino group is functionalised to become a $NHR_8$ group and/or, where present, the hydroxyl group is functionalised to become a $OR_8$ group; and
  - $AA_4$ is selected from $_D$-Ala, $_D$-Ser or $_D$-Lacate ($_D$-Lac),
- at each occurrence $R_8$ is independently selected from one or more of H, a fluorescent group or a pharmaceutically active moiety,
- n and m, and n' and m' are alternating repeating units, where n is from 5 to 100 and m is from 4 to 100, provided that m has the same value as n or is n−1 and n' is from 5 to 100 and m' is from 4 to 100, provided that m' has the same value as n' or is n'−1,
- p or p' are 1 or 0, or
- a pharmaceutically acceptable salt, solvate or prodrug thereof.

In embodiments of the first aspect of the invention, the compounds of formula Ia and Ib may be Ia' and Ib', respectively

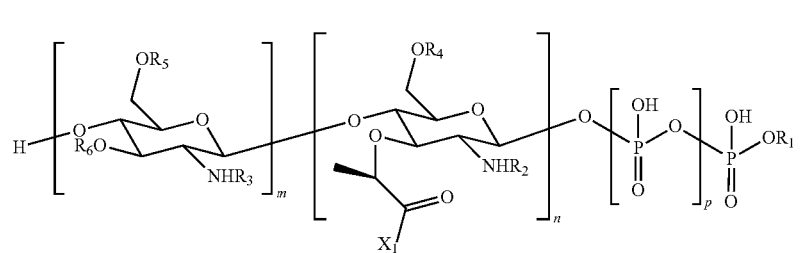

Ia'

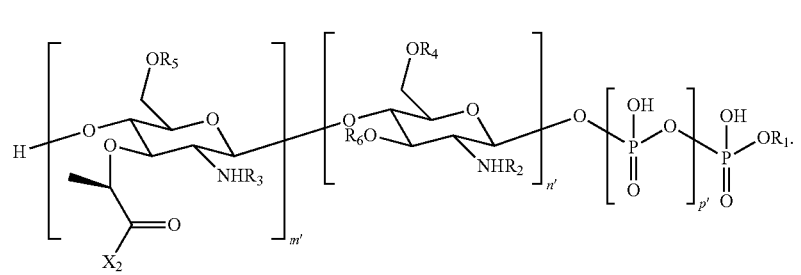

Ib'.

In embodiments of the above aspect and embodiment:

(i) when p and/or p' is 1 and $R_1$ represents $C_1$ to $C_{20}$ alkyl, then $R_8$ may represent a fluorescent group or a pharmaceutically active moiety or when p and/or p' is 0 and $R_1$ represents $-CH_2CH(CO_2H)OC_{1-20}$ alkyl, then $R_8$ may represent H;

(ii) when p and/or p' is 1, $R_1$ may represent $C_{10}$ to $C_{15}$ alkyl such as $C_{14}$ alkyl, or when p and/or p' is 0, $R_1$ may represent $-CH_2CH(CO_2H)OC_{10-15}$ alkyl, such as $-CH_2CH(CO_2H)OC_{12}$ alkyl;

(iii) each $R_7$ independently may represent $C_1$ to Ce alkyl, such as $C_1$ alkyl;

(iv) $AA_1$ may be selected from $_L$-Ala, $_L$-Gly, or $_L$-Ser, $AA_2$ may be selected from $_D$-isoglutamate ($\gamma$-$_D$-glutamate, $\gamma$-$_D$-Glu) or $_D$-isoglutamine, $AA_3$ may be selected from $_L$-Lys, $_D$-Lys, $_L$-Orn or $_L$-2,4-diaminobutyrate, where the amino group may be functionalised to become a $NHR_8$, and $AA_4$ may be selected from $_D$-Ala or $_D$-Ser (e.g. $AA_1$ may be $_L$-Ala, $AA_2$ may be $_D$-isoglutamate ($\gamma$-$_D$-glutamate, $\gamma$-$_D$-Glu), $AA_3$ may be selected from $_L$-Orn or, more particularly, $_L$-Lys, where the amino group may be functionalised to become a $NHR_8$ group and $AA_4$ may be $_D$-Ala);

(v) n may be from 5 to 50 and m may be from 4 to 50, provided that m has the same value as n or is n−1, n' may be from 5 to 50 and m' may be from 4 to 50, provided that m' has the same value as n' or is n'−1 (e.g. n may be from 5 to 25 and m may be from 4 to 25, provided that m has the same value as n or is n−1; n' may be from 5 to 25 and m' may be from 4 to 25, provided that m' has the same value as n' or is n'−1), optionally wherein the sum of n+m or n'+m' may be selected from one or more of 10, 25 or 50;

(vi) when a $R_8$ group is a fluorescent group, it may be selected from one or more of a rhodamine, a cyanine and a naphthalimide, where the point of attachment of the rhodamine, cyanine and naphthalimide to the rest of the molecule is through a $SO_2$ or $C=O$ moiety (e.g. $R_8$ may be selected from one or more of:

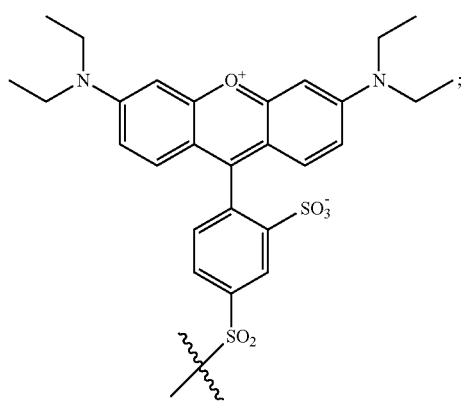

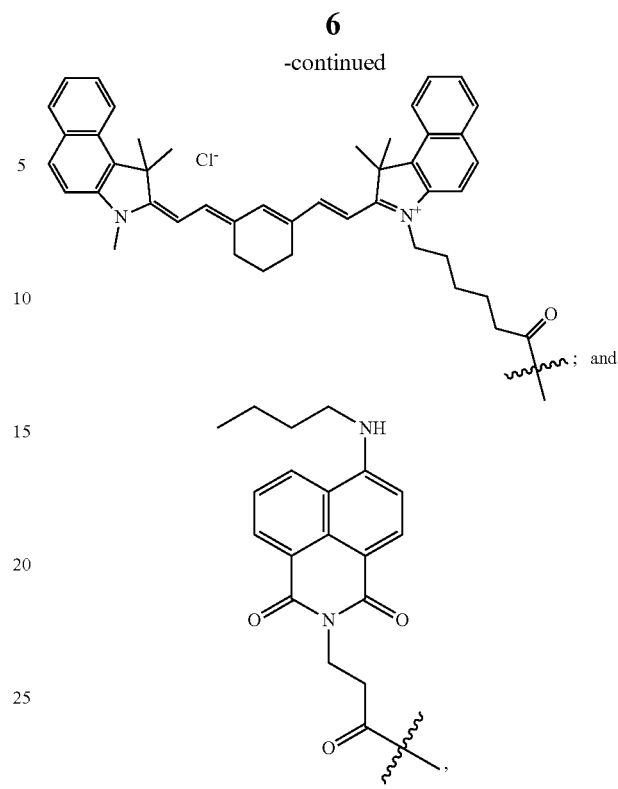

where the wavy line in each of the above moieties represents the point of attachment to the rest of the molecule);

(vii) when a $R_8$ group is a pharmaceutically active moiety, it may be selected from one or more of an antibiotic and an antigen moiety, where the point of attachment of the antibiotic and the antigen moiety to the rest of the molecule is through a $SO_2$ or $C=O$ moiety (e.g. $R_8$ may be selected from one or more of:

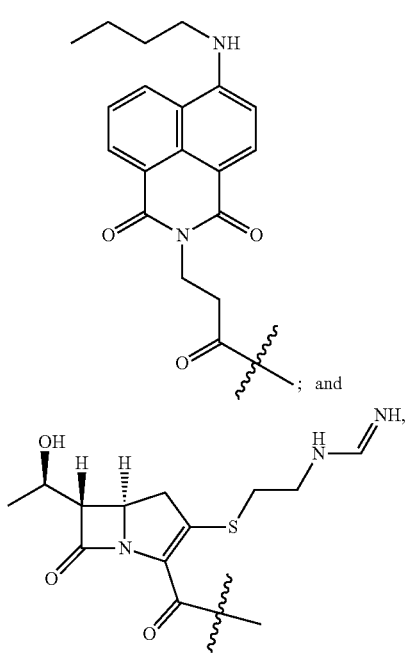

where the wavy line in each of the above moieties represents the point of attachment to the rest of the molecule).
In particular embodiments that are disclosed herein the compounds of formula Ia and Ib (or Ia' and Ib') may be selected from:
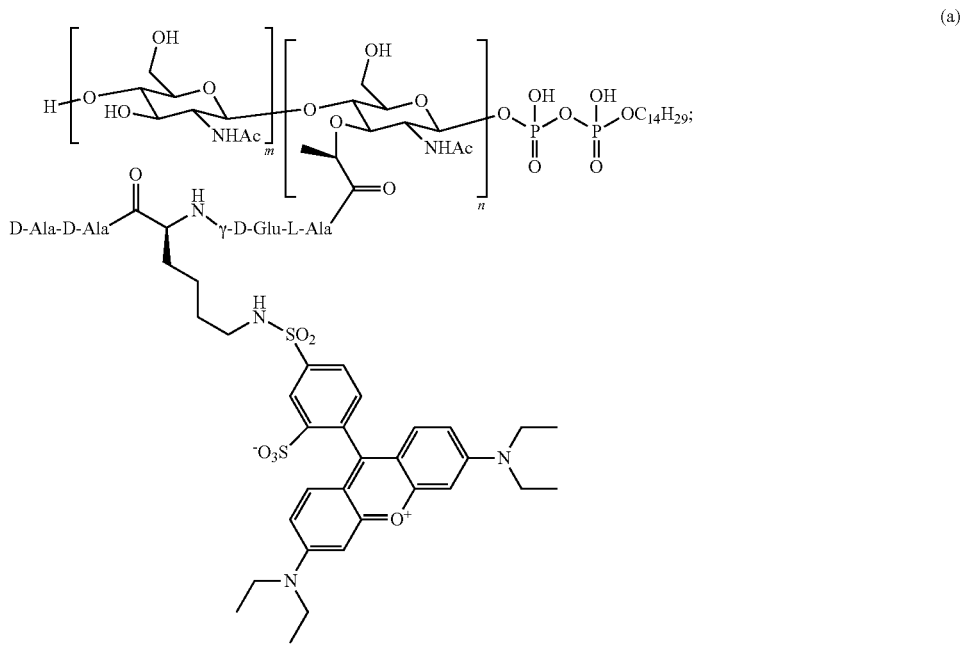
(a)
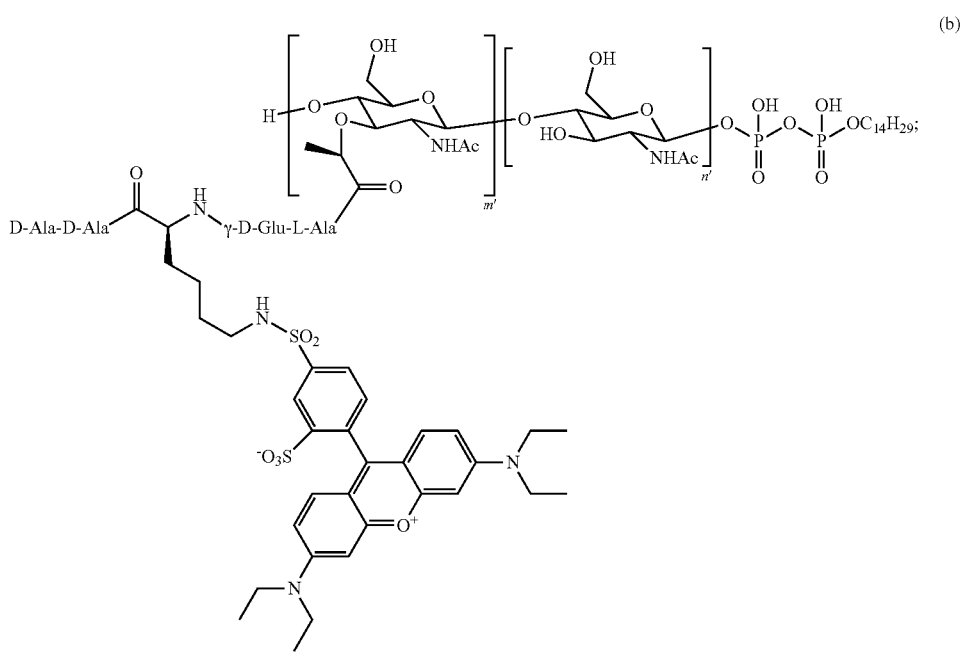
(b)

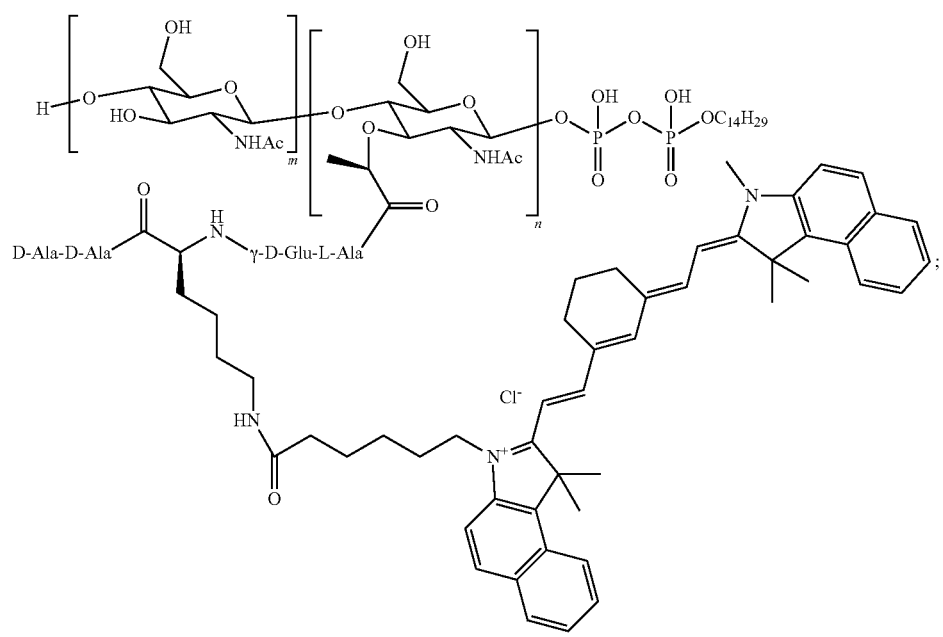
(c)
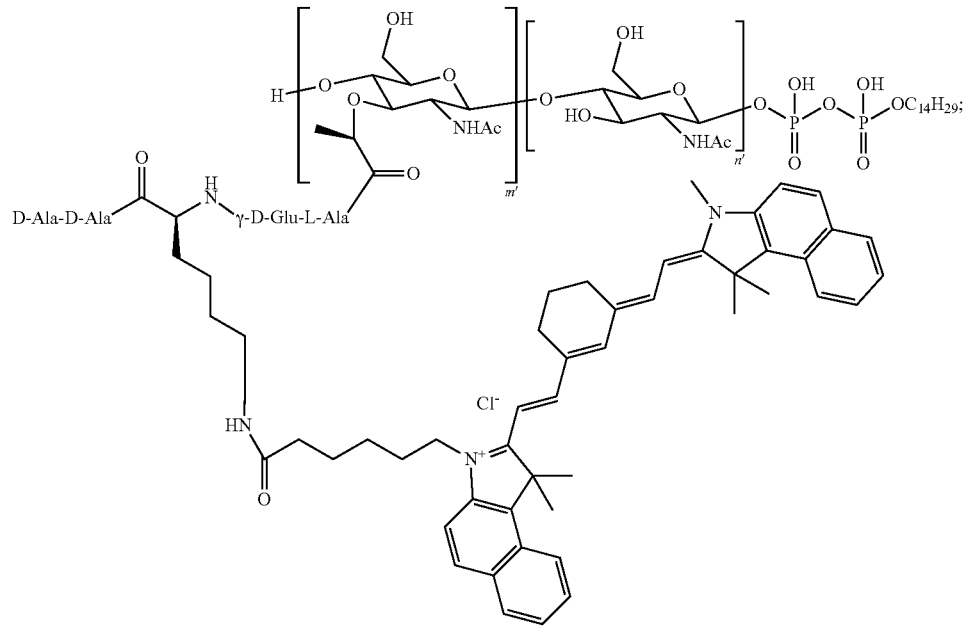
(d)

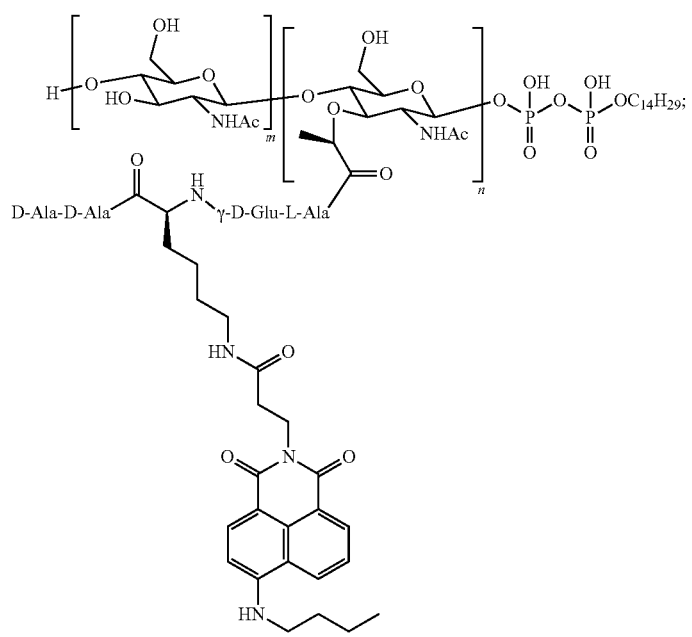
(e)
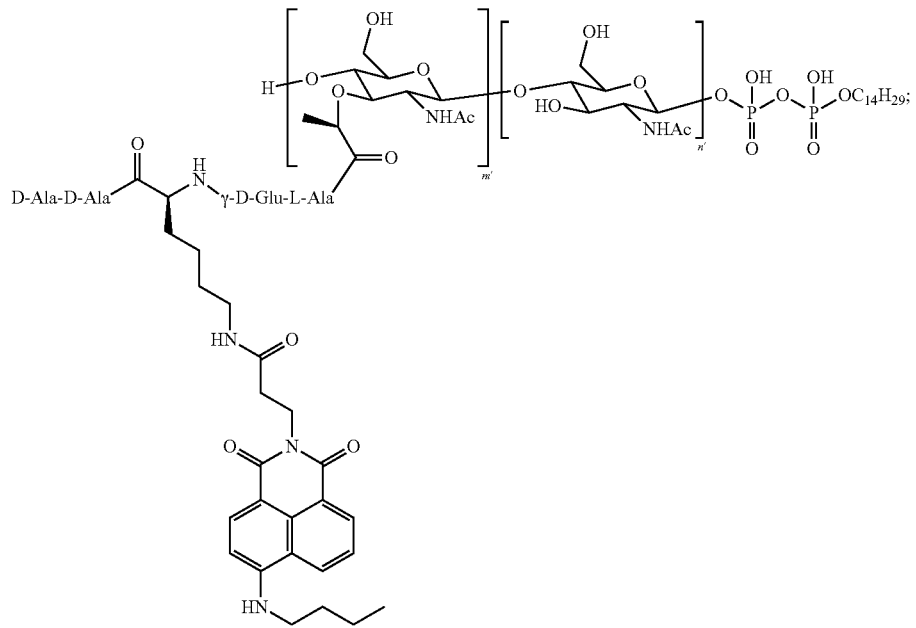
(f)

-continued
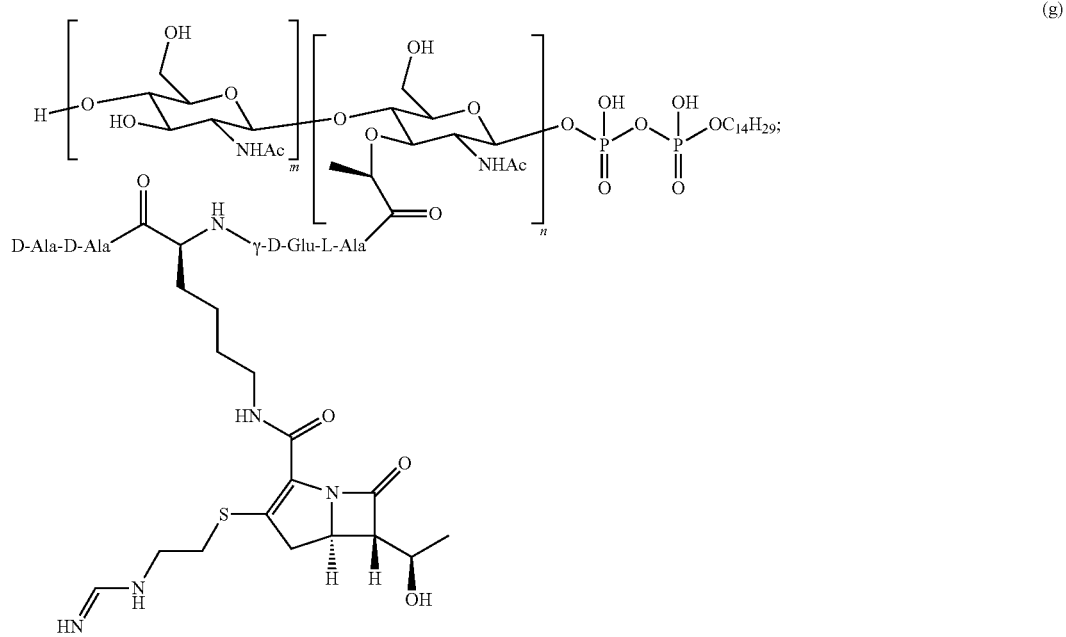
(g)
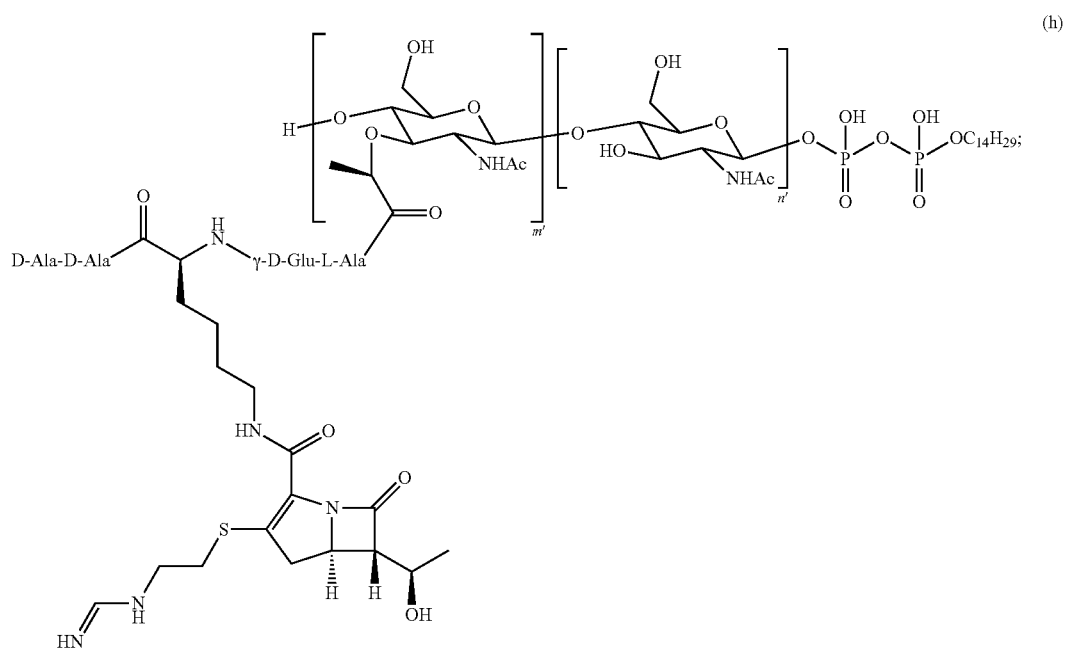
(h)
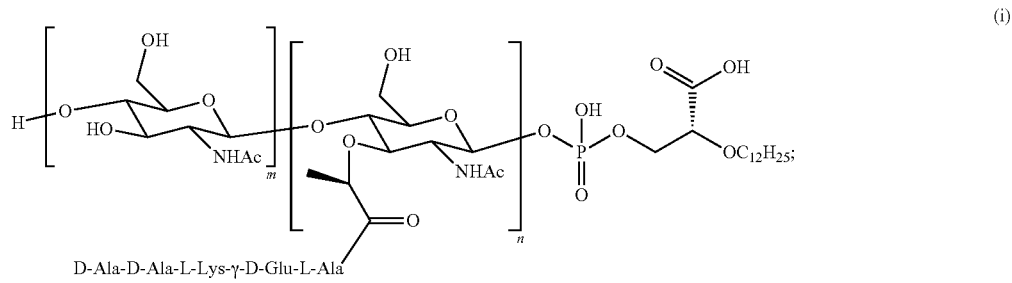
(i)

-continued
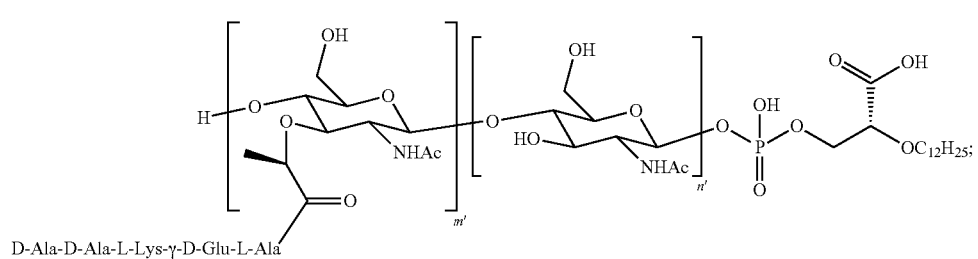
(j)
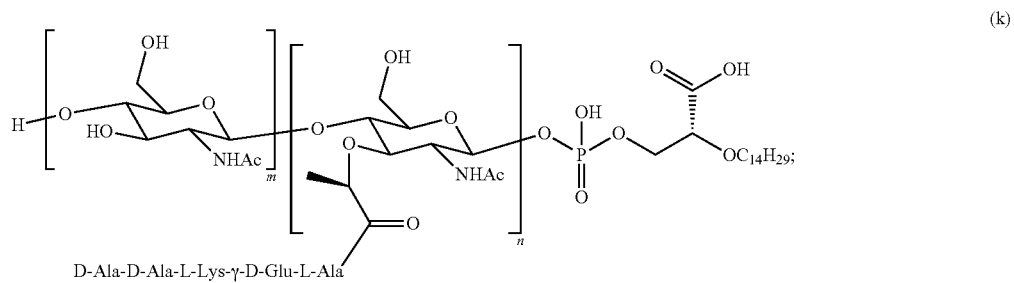
(k)
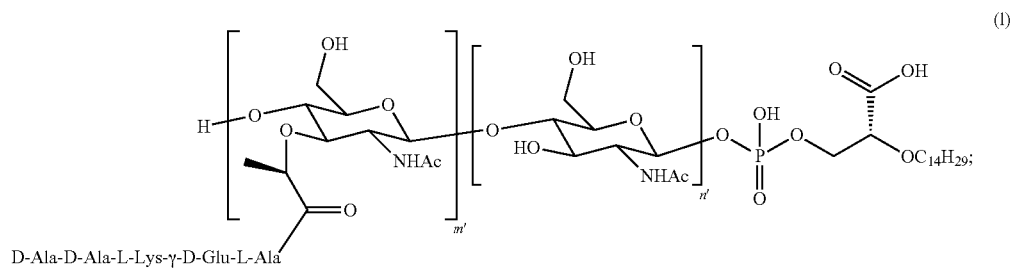
(l)
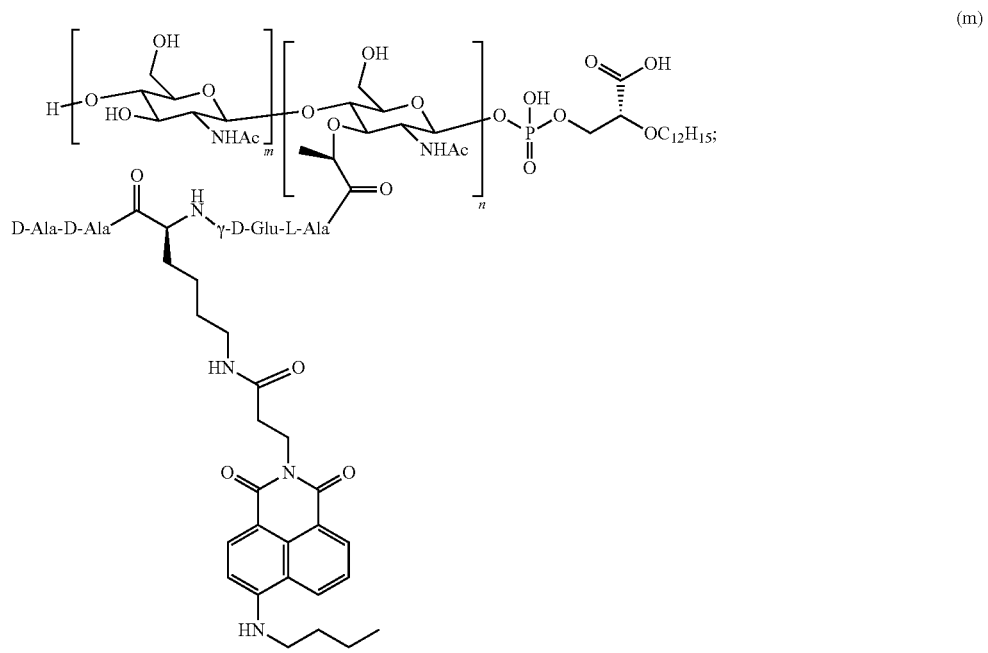
(m)

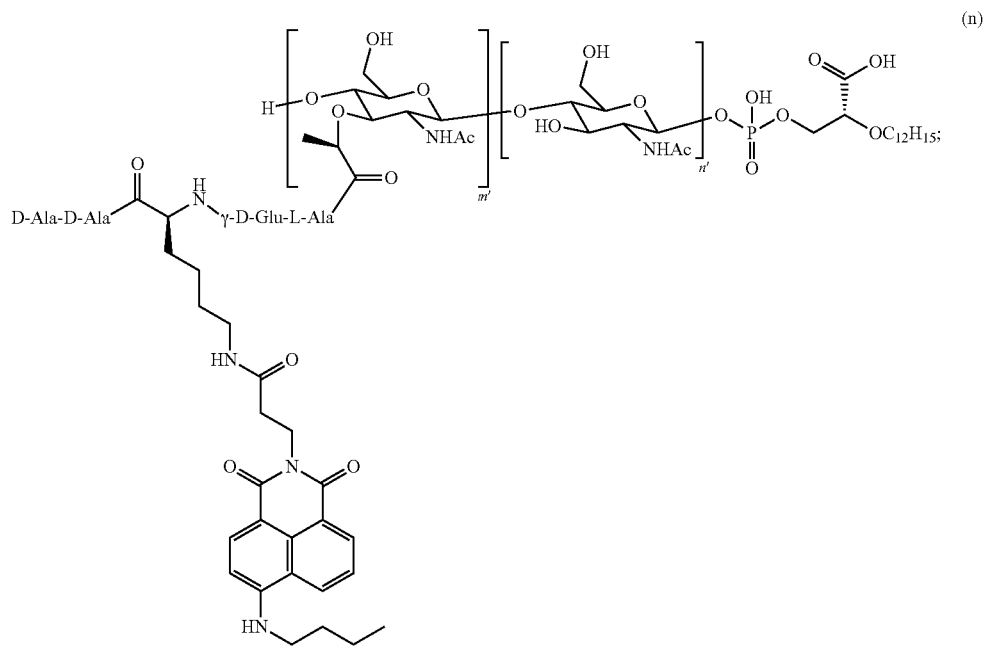
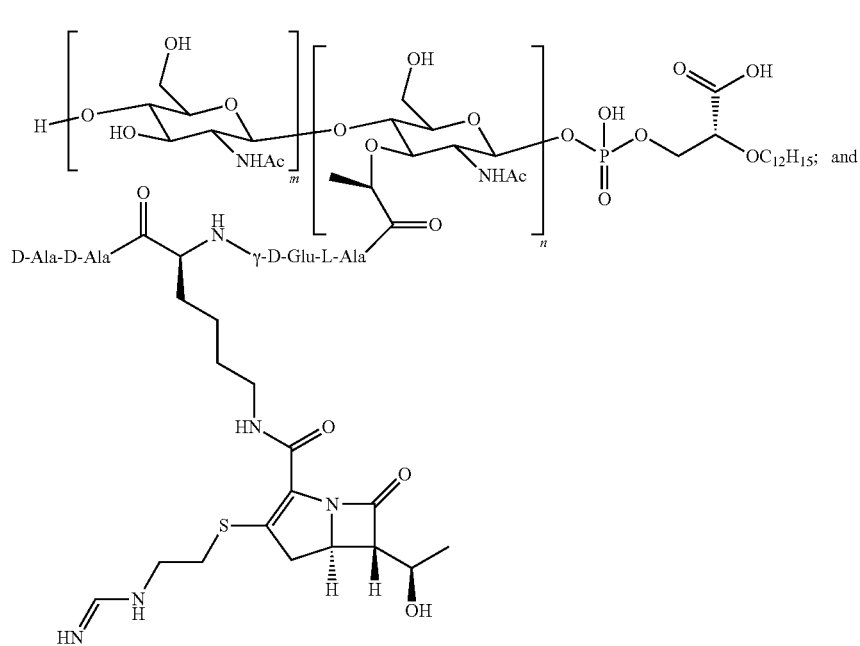

-continued

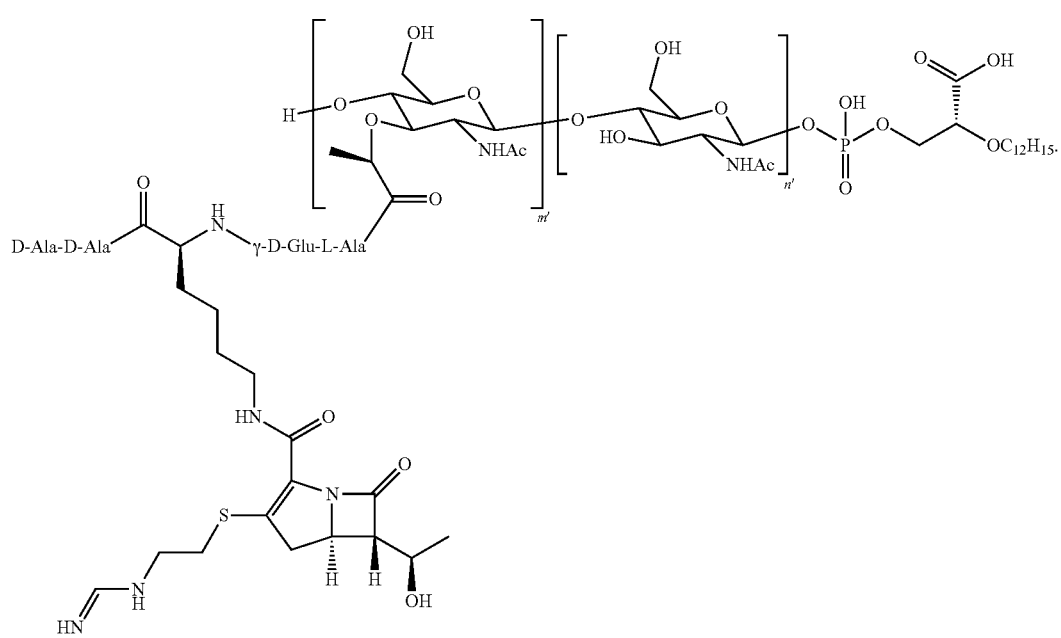

(p)

In a second aspect of the invention, there is provided a pharmaceutical formulation comprising a compound of formula Ia and/or formula Ib as described in the first aspect of the invention or any technically sensible combination of its embodiments and a pharmaceutically acceptable excipient, diluent or carrier.

In a third aspect of the invention, there is provided a use of a compound of formula Ia and/or formula Ib as described in the first aspect of the invention or any technically sensible combination of its embodiments or a pharmaceutically acceptable salt, solvate or prodrug thereof, in medicine.

In a fourth aspect of the invention, there is provided a:
(Ai) use of a compound of formula Ia and/or formula Ib as described in the first aspect of the invention or any technically sensible combination of its embodiments where $R_8$ is a pharmaceutically active moiety, or a pharmaceutically acceptable salt, solvate or prodrug thereof, in the preparation of a medicament for treating a microbial infection;
(Aii) compound of formula Ia and/or formula Ib as described in the first aspect of the invention or any technically sensible combination of its embodiments where $R_8$ is a pharmaceutically active moiety, or a pharmaceutically acceptable salt, solvate or prodrug thereof, for use in the treatment of a microbial infection;
(Aiii) method of treatment of a microbial infection comprising administering a pharmaceutically effective amount of a compound of formula Ia and/or formula Ib as described in the first aspect of the invention or any technically sensible combination of its embodiments where $R_8$ is a pharmaceutically active moiety, or a pharmaceutically acceptable salt, solvate or prodrug thereof, to a subject in need thereof.

In a fifth aspect of the invention, there is provided a:
(Bi) use of a compound of formula Ia and/or formula Ib as described in the first aspect of the invention or any technically sensible combination of its embodiments where $R_8$ is a fluorescent group, or a pharmaceutically acceptable salt, solvate or prodrug thereof, in the preparation of a medicament for detecting a microbial infection in a subject, wherein following administration of the compound of formula Ia and/or formula Ib to the subject and irradiation of the subject with light, a microbial infection is detected by the presence of fluorescence;
(Bii) compound of formula Ia and/or formula Ib as described in the first aspect of the invention or any technically sensible combination of its embodiments where $R_8$ is a fluorescent group, or a pharmaceutically acceptable salt, solvate or prodrug thereof, for use in detecting a microbial infection in a subject, wherein following administration of the compound of formula Ia and/or formula Ib to the subject and irradiation of the subject with light, a microbial infection is detected by the presence of fluorescence;
(Biii) method of detecting a microbial infection in a subject comprising administering a pharmaceutically effective amount of a compound of formula Ia and/or formula Ib as described in the first aspect of the invention or any technically sensible combination of its embodiments where $R_8$ is a fluorescent group, or a pharmaceutically acceptable salt, solvate or prodrug thereof, to a subject, subsequently exposing the subject to light irradiation and detecting a microbial infection by the presence of fluorescence.

In a sixth aspect of the invention, there is provided a method of determining antimicrobial resistance of a microbial infection in a sample in vitro, the method comprising the steps of:
(A) contacting the sample with an antimicrobial to provide an antimicrobial sample;
(B) contacting the antimicrobial sample after a period of time with a compound of formula Ia and/or formula Ib as described in the first aspect of the invention or any technically sensible combination of its embodiments where $R_8$ is a fluorescent group, or a pharmaceutically acceptable salt, solvate or prodrug thereof; and (C) detecting fluorescence produced by the fluorescent group upon exposure to a light source, wherein detection of fluorescence is used to determine antimicrobial resistance.

In embodiments of the seventh aspect of the invention:
(AA) the method may be conducted in parallel or series, such that multiple samples are subjected to steps (A) to (C) with a plurality of individual antimicrobials and/or combinations of antimicrobials to determine the antimicrobial resistance profile of the microbial infection;
(AB) the period of time in step (B) may be from 5 minutes to 24 hours, such as 30 minutes to 12 hours, such as 45 minutes to 6 hours, such as 1 hour.

In an eighth aspect of the invention, there is provided a method of determining an effective dose of one or more antimicrobial agents to kill a microorganism, the method comprising the steps of:
(iA) contacting one or more antimicrobial test solutions comprising one or more antimicrobial agents with the microorganism to provide one or more test samples, when there are two or more test samples, the concentration of each of the one or more antimicrobial agents is varied between the two or more antimicrobial test solutions to define a range;
(iB) contacting each of the one or more test samples after a period of time with a compound of formula Ia and/or formula Ib as described in any one of claims 1 to 10 and 13(*a*) to 13(*f*) where $R_8$ is a fluorescent group, or a pharmaceutically acceptable salt, solvate or prodrug thereof; and
(iC) detecting fluorescence produced by the fluorescent group upon exposure to a light source in each of the test samples, wherein
detection of fluorescence in a test sample indicates the concentration of the one or more antimicrobial agents in said antimicrobial test solution is not effective, and the lack of detection of fluorescence indicates the concentration of the one or more antimicrobial agents in said antimicrobial test solution is effective, thereby determining the effective dose of the one or more antimicrobial agents.

In embodiments of the eighth aspect of the invention, the period of time in step (iB) is from 5 minutes to 24 hours, such as 30 minutes to 12 hours, such as 45 minutes to 6 hours, such as 1 hour.

In a ninth aspect of the invention, there is provided a method of making a compound of formula Ia and/or Ib as described in the first aspect of the invention or any technically sensible combination of its embodiments, wherein the compound(s) is obtained and/or obtainable from a chitosan molecule comprising from 9 to 100 sugar units, such as from 10 to 50 sugar units, such as 10 to 25 sugar units.

DRAWINGS

FIG. 1 Peptidoglycan biosynthesis in bacteria. MurG is an enzyme that catalyzes the glycosylation reaction between UDP-GlcNAC (which contains NAG) and Lipid I substrate (which contains NAM and a pendant pentapeptide), to form the lipid-linked NAG-NAM β-(1,4) disaccharide known as Lipid II. After a pentaglycine bridge is added to Lipid II, it is translocated to the exterior surface of the cell membrane and incorporated into the peptidoglycan network by peptidoglycan glycosyltransferases (PGTs) to form peptidoglycan oligomers. Cross-linking by transpeptidases (TPs) completes peptidoglycan biosynthesis. Some TPs bind to penicillin, and are thus known as penicillin-binding proteins (PBPs).

Figure 2:
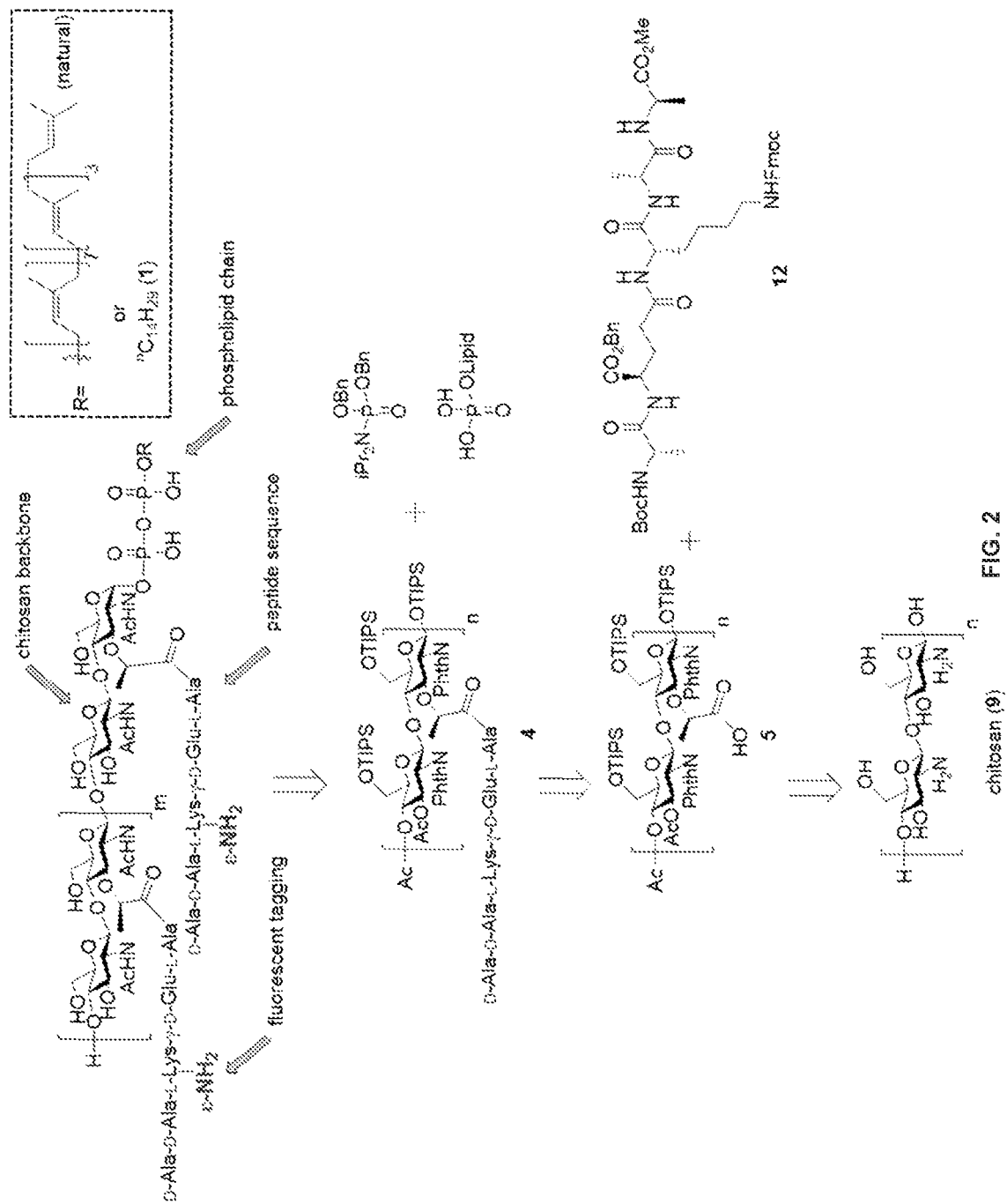

FIG. 2 Retrosynthetic analysis of Peptidoglycan Oligomers (PGOs) 1 from chitosan 9. Key steps and challenges are highlighted in the synthesis. PGOs 1 can be divided into the pentapeptide subunit (capable of fluorescent tagging), the NAG-NAM oligosaccharide subunit, and the phospholipid chain. The lipid linker can be added to 4, while the pentapeptide 12 can be added to 5.

FIG. 3 Synthesis of PGO. A, Total synthesis of PGO 1 and rhodamine-labeled PGO 1 from low molecular weight chitosan 9. Reactions and conditions. a, phthalic anhydride (3 equiv), AcOH/$H_2O$ b, Imidazole, TIPSCl (7 equiv), DMF c, NaH, 2-bromopropanoate (0.5 equiv), DMF d, acetic anhydride (5 equiv), pyridine e, $H_2NR$ (peptide) (1 equiv), HATU, HOAt, DIPEA, DMF, f, 1) TBAF, hydrazine, AcOH, MeOH, 2) $Ac_2O$ g, 1) $MeNH_2$, 2) 1H-tetrazole, dibenzyl N,N-diisopropylphosphoramidite (2 equiv), 3) tert-butyl hydroperoxide, $CH_2Cl_2$, h, 1) $H_2$, Pd/C, MeOH, 2) $^nC_{14}H_{29}OPO(OH)_2$ (2 equiv), DMF, 3) LiOH, MeOH/$H_2O$ (v/v, 1:1). B, LC-ESI-TOF MS analysis of metabolites from lysozyme degradation assay. Two major resultant peaks at t=0.69 min and t=0.99 min correspond to the NAG-NAM subunit and the phospholipid respectively. The remaining peaks were from metabolites from the enzyme and the buffer used in the lysozyme degradation assay.

FIG. 4 PGOs are successfully incorporated into both Gram-positive and -negative bacterial cell walls. a, Fluorescence STED confocal studies of 6 different bacteria strains. (top set of images) color marks fluorescence from the membrane dye FM 1-43fx, (middle set of images) color marks fluorescence from the PGOs-rhodamine, and (bottom set of images) color indicates colocalisation of the two fluorophores in bacterial cells. Scale bar=2 μm. b, Relative fluorescence intensity on bacterial surfaces after incorporation of PGOs. A total of above one hundred cells from each strain were used for measurements (refer to Example 6), and the average PGOs-rhodamine fluorescence signal per cell was measured for comparison. c, Confocal microscopic images of 3T3 cells incubated with (top row) and without (bottom row) PGOs-rhodamine. Incubation was done at 100 μg/mL substrate concentration for 1 hour, which was the same as the conditions adopted for bacteria. Scale bar=10 μm.

Figure 5:
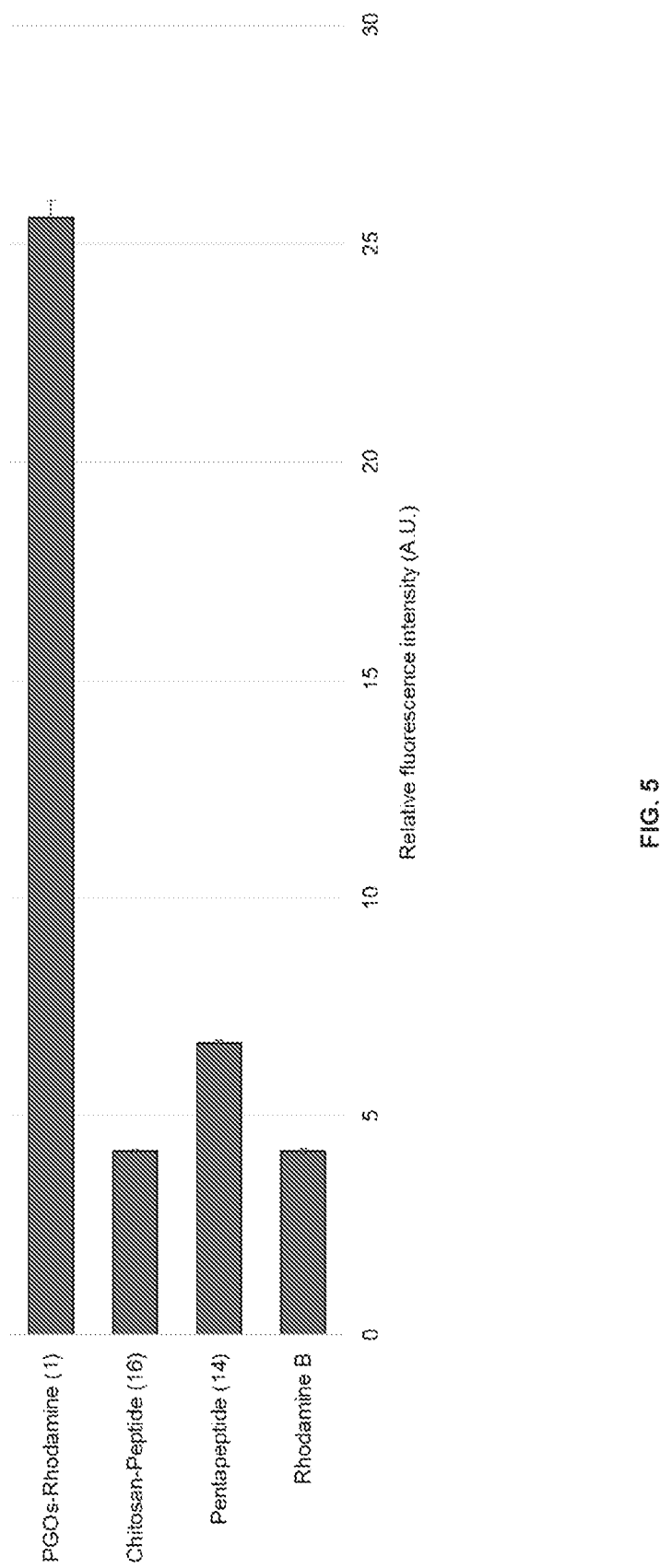

FIG. 5 Cell surface relative fluorescence intensity of *E. faecalis* after incubation with different substrates. A total of above one hundred cells from each strain were used for measurements (refer to Example 6), and the average fluorescence signal per cell was measured for comparison.

FIG. 6 Mechanism of PGO incorporation. a, Magnified STED confocal microscopic images of *S. aureus* and *E. faecalis*, scale bar=1 μm. b, Localisation of PGOs-rhodamine and Boc-FL in wild-type and L-form *E. faecalis*OG1RF imaged with TIRF microscopy. Scale bar=1 μm for wild-type and 10 μm for L-form respectively. PGOs-rhodamine (red) and Boc-FL (green) are co-localised in the septa of wild-type cells, and the punctae of L-form cells. c, Calorimetric titration of PGOs 1 with *E. coli* PBP1a.

Figure 7:
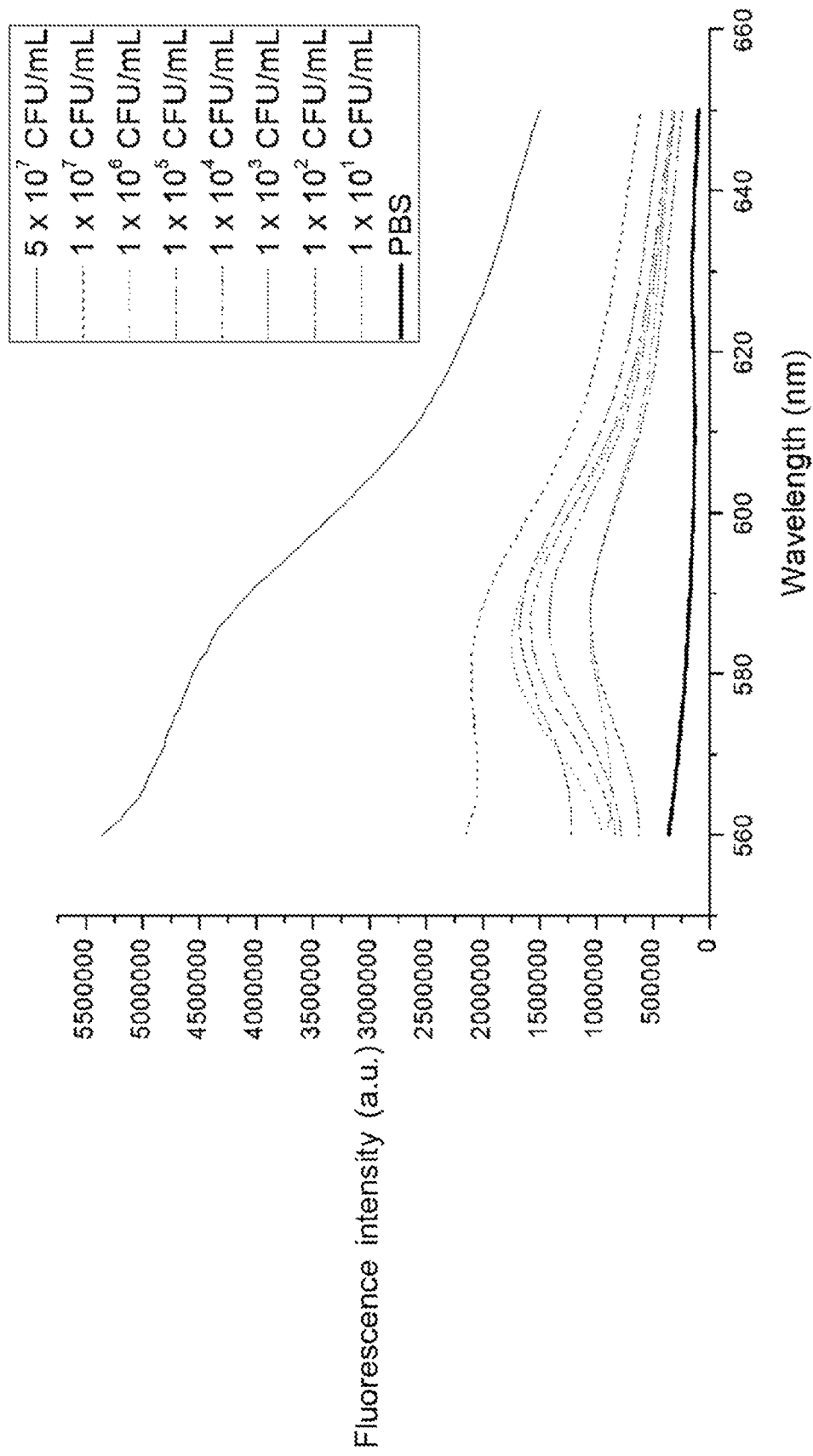

FIG. 7 Fluorescence intensity of bacteria suspension labelled with PGOs-rhodamine. All suspensions (including PBS control) were incubated with PGOs-rhodamine at 200 μg/mL for 1 hour and washed with PBS before measurement of fluorescence with fluorospectrometer.

Figure 8:
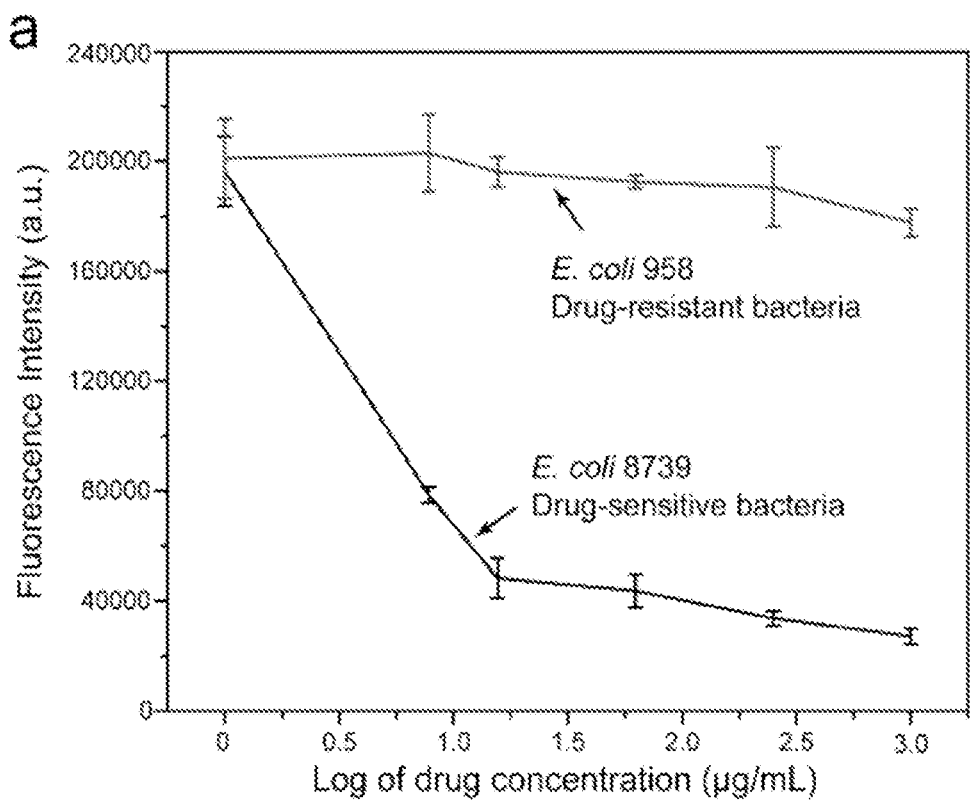
Figure 8:
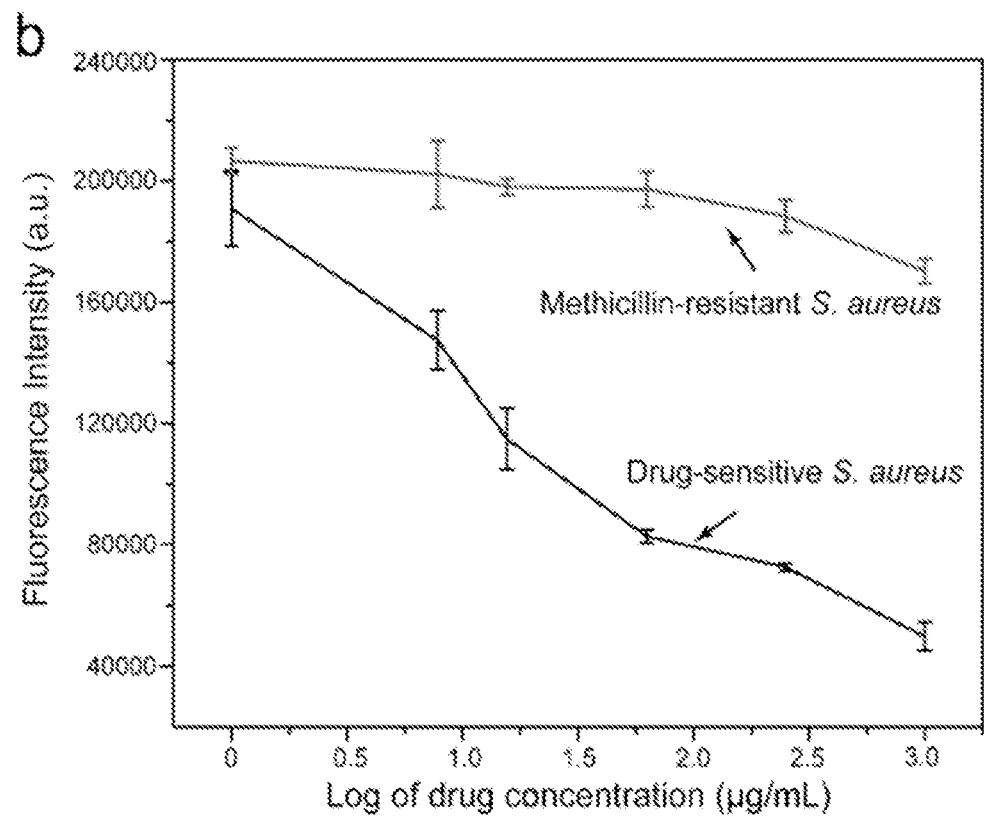

FIG. 8 Selective labelling of antibiotic resistant bacteria. Fluorescence intensity comparison of resistant and susceptible a, *E. coli* and b, *S. aureus* at $10^6$ CFU/mL.

Figure 9:
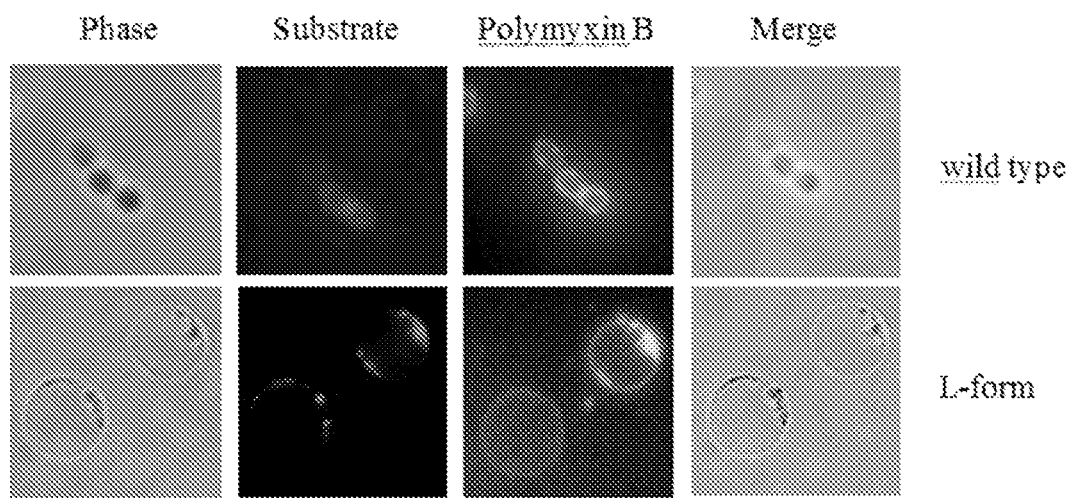

FIG. 9 TIRF images of Wild type and L-form cells of *E. faecalis* OG1RF grown in DM3 medium were incubated with sulforhodamine B labelled substrate 1 and membrane affinity dye Polymyxin B-BODIPY FL. Scale bars, 1 μm and 10 μm for wild and L-forms respectively.

Figure 10:
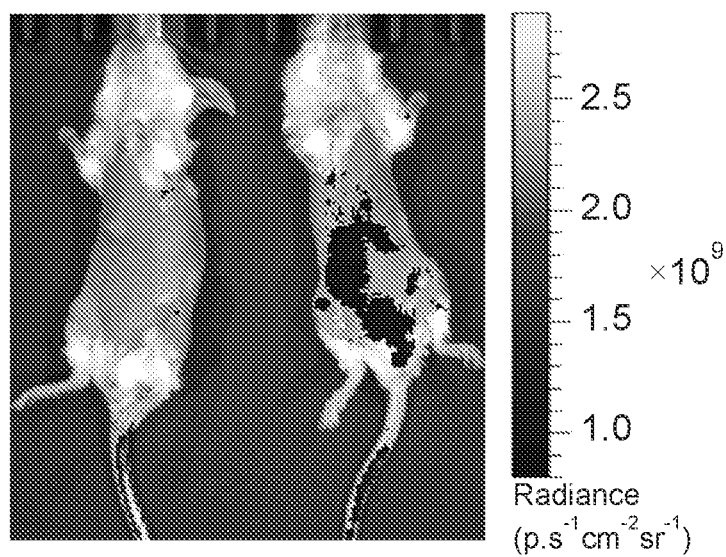

FIG. 10 Representative images for non-infected mice (left) and infected mice (right) 8 hours after receiving intravenous injection of PGOs-Cy7.5.

Figure 11:
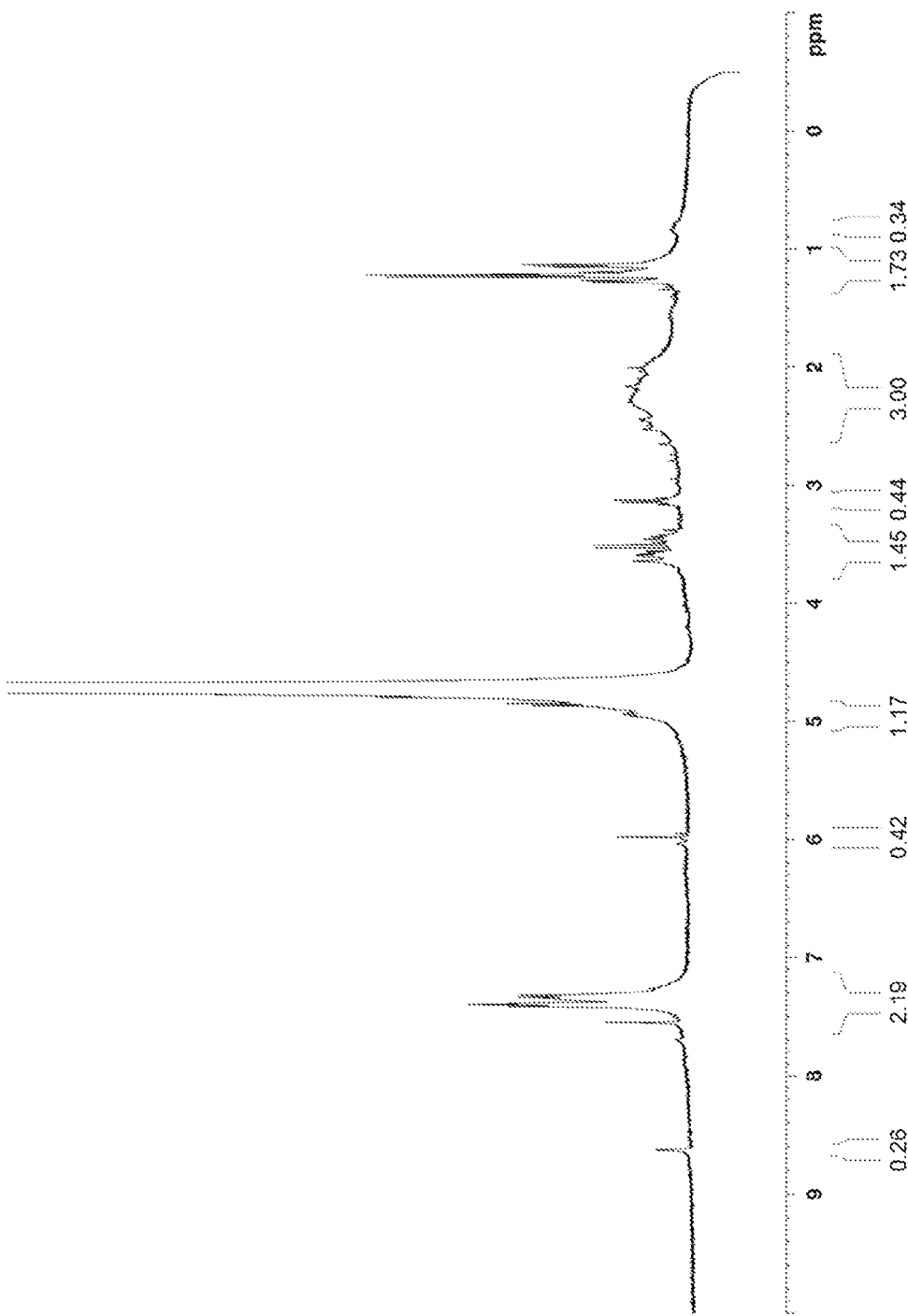

FIG. 11 $^1$H NMR spectrum of fluorescently labeled 1 used for STED confocal microscopy (400 MHz, D$_2$O).

Figure 12:
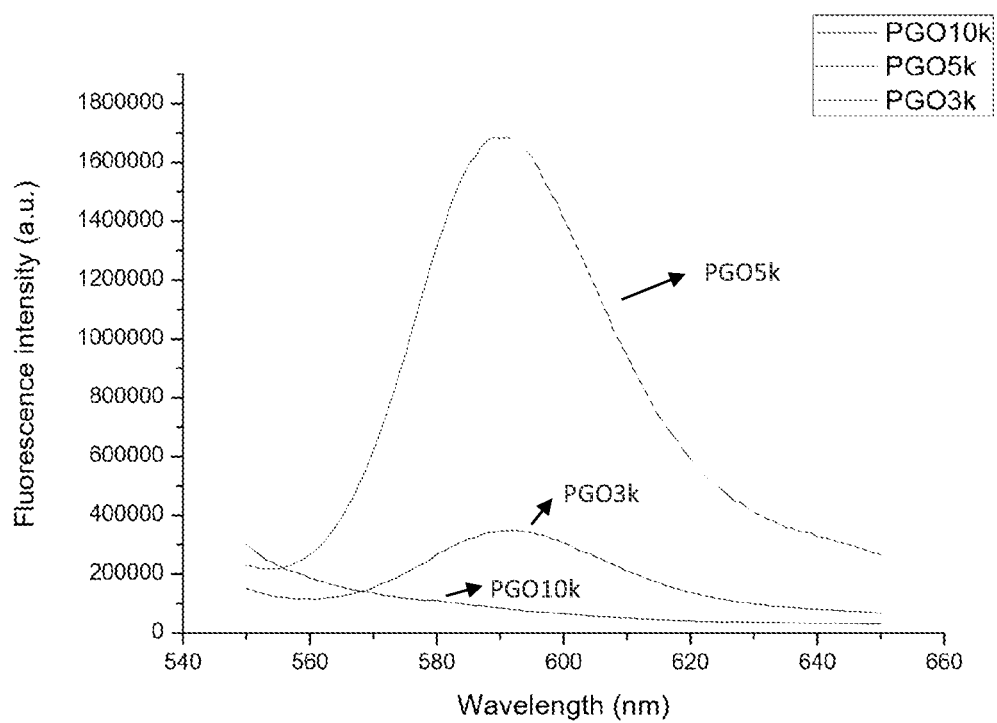

FIG. 12 Fluorescence intensity of bacterial samples after incubation with PGOs-rhodamine of varying sizes. Intensity is in arbitrary units (a.u.). The samples were labelled according to the molecular weight of chitosans they were synthesized from.

FIG. 13 Examples from three categories of fluorescent dye conjugates reported in use for labelling bacterial cell wall.

DESCRIPTION

The current invention relates to biohybrid peptidoglycan oligomers (PGOs) that can be efficiently synthesised from chitosan, a biopolymer readily available from crustacean waste. The PGOs disclosed herein are selectively taken up by Gram-positive and Gram-negative bacteria strains, but not mammalian cells. Additionally, these PGOs can be modified to target specific bacteria strains, such as through modification of the pentapeptide present in each PGO. The PGOs can be conjugated to a fluorescent dye or a pharmaceutical drug (or multiples of each). They have the potential to be customised for determining anti-microbial resistance of a microbial infection, bacteria bioimaging studies and development of novel antibiotics.

Thus in a first aspect of the invention, there is provided a compound of formula Ia and/or formula Ib:

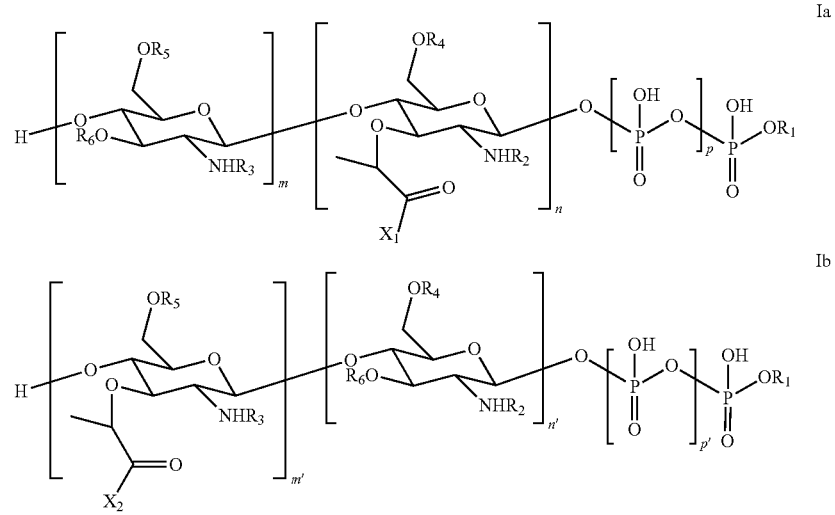

wherein:
R$_1$ represents C$_1$ to C$_{20}$ alkyl or —CH$_2$CH(CO$_2$H)OC$_{1-20}$ alkyl;
R$_2$ and R$_3$ each independently represent —C(=O)R$_7$;
R$_4$ to R$_6$ each represent H;
each R$_7$ independently represents C$_1$ to C$_{20}$ alkyl;
X$_1$ and X$_2$ independently represent -AA$_1$-AA$_2$-AA$_{3\text{-}D}$-Ala-AA$_4$, where:

AA$_1$ is selected from $_L$-Ala, $_L$-Gly, $_D$-Gly or $_L$-Ser;
AA$_2$ is selected from $_D$-isoglutamate (γ-$_D$-glutamate, γ-$_D$-Glu), $_D$-isoglutamine, or threo-3-hydroxyglutamate
AA$_3$ is selected from $_L$-homoserine, $_D$-homoserine, $_D$-5-hydroxylysine, $_D$-Orn, $_L$-Lys, Lys, $_L$-Orn, $_L$-2,4-diaminobutyrate, or $_L$-5-hydroxylysine, where the amino group is functionalised to become a NHR$_8$ group and/or, where present, the hydroxyl group is functionalised to become a OR$_8$ group; and
AA$_4$ is selected from $_D$-Ala, $_D$-Ser or $_D$-Lactate ($_D$-Lac),
at each occurrence R$_8$ is independently selected from one or more of H, a fluorescent group or a pharmaceutically active moiety,
n and m, and n' and m' are alternating repeating units, where n is from 5 to 100 and m is from 4 to 100, provided that m has the same value as n or is n−1 and n' is from 5 to 100 and m' is from 4 to 100, provided that m' has the same value as n' or is n'−1,
p or p' are 1 or 0, or
a pharmaceutically acceptable salt, solvate or prodrug thereof.

When used herein, three letter codes for amino acids are used in line with their conventional meanings in the art. It will be appreciated that in some bacterial strains, $_D$-lactate may be found in place of D-alanine. When used herein, it may be referred to by the three letter code $_D$-Lac.

References herein (in any aspect or embodiment of the invention) to compounds of formula Ia and/or Ib (including compounds of formula Ia' and/or Ib') includes references to such compounds per se, to tautomers of such compounds, as well as to pharmaceutically acceptable salts or solvates, or pharmaceutically functional derivatives of such compounds.

It will be appreciated that the methods of making the compounds of formula Ia and Ib (and hence the compounds of formula Ia' and Ib') may result in a mixture of said compounds. As such, the compounds disclosed herein may be a mixture of the compounds of formula Ia and formula Ib (and hence the compounds of formula Ia' and Ib'). As will be appreciated, the exact mixture obtained will depend on various factors determined by the synthetic route used to make the compounds and the reagents used. Therefore, while the mixture obtained may be a 50:50 wt % mixture, it may also be a mixture of from 0.0001:99.9999 to 99.9999: 0.0001 wt % mixture. In addition, it is contemplated that the compounds of formula Ia and Ib (and hence the compounds of formula Ia' and Ib') may be synthesised or isolated from each other to provide substantially pure compound thereof (or salts, solvates or prodrugs thereof).

Pharmaceutically acceptable salts that may be mentioned include acid addition salts and base addition salts. Such salts may be formed by conventional means, for example by reaction of a free acid or a free base form of a compound of formula Ia and Ib (including the compounds of formula Ia' and Ib') with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of formula Ia and Ib (including the compounds of formula Ia' and Ib') in the form of a salt with another counter-ion, for example using a suitable ion exchange resin.

Examples of pharmaceutically acceptable salts include acid addition salts derived from mineral acids and organic acids, and salts derived from metals such as sodium, magnesium, or preferably, potassium and calcium.

Examples of acid addition salts include acid addition salts formed with acetic, 2,2-dichloroacetic, adipic, alginic, aryl sulphonic acids (e.g. benzenesulphonic, naphthalene-2-sulphonic, naphthalene-1,5-disulphonic and p-toluenesulphonic), ascorbic (e.g. L-ascorbic), L-aspartic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), malonic, (±)-DL-mandelic, metaphosphoric, methanesulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, tartaric (e.g. (+)-L-tartaric), thiocyanic, undecylenic and valeric acids.

Particular examples of salts are salts derived from mineral acids such as hydrochloric, hydrobromic, phosphoric, metaphosphoric, nitric and sulphuric acids; from organic acids, such as tartaric, acetic, citric, malic, lactic, fumaric, benzoic, glycolic, gluconic, succinic, arylsulphonic acids; and from metals such as sodium, magnesium, or preferably, potassium and calcium.

As mentioned above, also encompassed by formula Ia and Ib (including the compounds of formula Ia' and Ib') are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particularly preferred solvates are hydrates, and examples of hydrates include hemihydrates, monohydrates and dihydrates.

For a more detailed discussion of solvates and the methods used to make and characterise them, see Bryn et al., *Solid-State Chemistry of Drugs*, Second Edition, published by SSCI, Inc of West Lafayette, Ind., USA, 1999, ISBN 0-967-06710-3.

The term "prodrug" of a relevant compound of formula Ia and Ib (including the compounds of formula Ia' and Ib') includes any compound that, following oral or parenteral administration, is metabolised in vivo to form that compound in an experimentally-detectable amount, and within a predetermined time (e.g. within a dosing interval of between 6 and 24 hours (i.e. once to four times daily)).

Prodrugs of compounds of formula Ia and Ib (including the compounds of formula Ia' and Ib') may be prepared by modifying functional groups present on the compound in such a way that the modifications are cleaved, in vivo when such prodrug is administered to a mammalian subject. The modifications typically are achieved by synthesizing the parent compound with a prodrug substituent. Prodrugs include compounds of formula Ia and Ib (including the compounds of formula Ia' and Ib') wherein a hydroxyl, amino, sulfhydryl, carboxyl or carbonyl group in a compound of formula Ia and Ib (including the compounds of formula Ia' and Ib') is bonded to any group that may be cleaved in vivo to regenerate the free hydroxyl, amino, sulfhydryl, carboxyl or carbonyl group, respectively.

Examples of prodrugs include, but are not limited to, esters and carbamates of hydroxyl functional groups, esters groups of carboxyl functional groups, N-acyl derivatives and N-Mannich bases. General information on prodrugs may be found e.g. in Bundegaard, H. "Design of Prodrugs" p. 1-92, Elsevier, New York-Oxford (1985).

Compounds of formula Ia and Ib (including the compounds of formula Ia' and Ib'), as well as pharmaceutically acceptable salts, solvates and pharmaceutically functional derivatives of such compounds are, for the sake of brevity, hereinafter referred to together as the "compounds of formula Ia and/or Ib".

Compounds of formula Ia and Ib (including the compounds of formula Ia' and Ib') may contain double bonds and may thus exist as E (entgegen) and Z (zusammen) geometric isomers about each individual double bond. All such isomers and mixtures thereof are included within the scope of the invention.

Compounds of formula Ia and Ib (including the compounds of formula Ia' and Ib') may exist as regioisomers and may also exhibit tautomerism. All tautomeric forms and mixtures thereof are included within the scope of the invention.

Compounds of formula Ia and Ib (including the compounds of formula Ia' and Ib') may contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

In embodiments herein, the word "comprising" may be interpreted as requiring the features mentioned, but not limiting the presence of other features. Alternatively, the word "comprising" may also relate to the situation where only the components/features listed are intended to be present (e.g. the word "comprising" may be replaced by the phrases "consists of" or "consists essentially of"). It is explicitly contemplated that both the broader and narrower interpretations can be applied to all aspects and embodiments of the present invention. In other words, the word "comprising" and synonyms thereof may be replaced by the phrase "consisting of" or the phrase "consists essentially of" or synonyms thereof and vice versa.

Unless otherwise stated, the term "alkyl" refers to an unbranched or branched, cyclic, saturated or unsaturated (so forming, for example, an alkenyl or alkynyl) hydrocarbyl radical, which may be substituted or unsubstituted (with, for example, one or more halo atoms). Where the term "alkyl" refers to an acyclic group, it is preferably $C_{1-10}$ alkyl and, more preferably, $C_{1-6}$ alkyl (such as ethyl, propyl, (e.g. n-propyl or isopropyl), butyl (e.g. branched or unbranched butyl), pentyl or, more preferably, methyl). Where the term "alkyl" is a cyclic group (which may be where the group "cycloalkyl" is specified), it is preferably $C_{3-12}$ cycloalkyl and, more preferably, $C_{5-10}$ (e.g. $C_{5-7}$) cycloalkyl.

For the avoidance of doubt, references herein to the compound of formula Ia and/or Ib include, where the context permits, references to any of compounds of formula Ia, Ib, Ia' or Ib'. Further, references to any of compounds of formula Ia, Ib, Ia' or Ib' includes references to such compounds per se, to tautomers of such compounds, as well as to pharmaceutically acceptable salts or solvates, or pharmaceutically functional derivatives of such compounds.

Further embodiments of the invention that may be mentioned include those in which the compound of formula Ia and/or Ib (including a compound of formula Ia' and/or Ib') is isotopically labelled. However, other particular embodiments of the invention that may be mentioned include those in which the compound of formula Ia and/or Ib (including the compound of formula Ia' and/or Ib') is not isotopically labelled.

The term "isotopically labelled", when used herein includes references to compounds of formula Ia and Ib (including the compounds of formula Ia' and Ib') in which there is a non-natural isotope (or a non-natural distribution of isotopes) at one or more positions in the compound. References herein to "one or more positions in the compound" will be understood by those skilled in the art to refer to one or more of the atoms of the compound of formula Ia and/or Ib (including a compound of formula Ia' and/or Ib'). Thus, the term "isotopically labelled" includes references to compounds of formula Ia and Ib (including the compounds of formula Ia' and Ib') that are isotopically enriched at one or more positions in the compound.

The isotopic labelling or enrichment of the compound of formula Ia and/or Ib (including a compound of formula Ia' and/or Ib') may be with a radioactive or non-radioactive isotope of any of hydrogen, carbon, nitrogen, oxygen, sulfur, fluorine, chlorine, bromine and/or iodine. Particular isotopes that may be mentioned in this respect include $^2H$, $^3H$, $^{11}C$, $^{13}C$, $^{14}C$, $^{13}N$, $^{15}N$, $^{15}O$, $^{17}O$, $^{18}O$, $^{35}S$, $^{18}F$, $^{37}Cl$, $^{77}Br$, $^{82}Br$ and $^{125}I$).

When the compound of formula Ia and/or Ib (including a compound of formula Ia' and/or Ib') is labelled or enriched with a radioactive or nonradioactive isotope, compounds of formula I that may be mentioned include those in which at least one atom in the compound displays an isotopic distribution in which a radioactive or non-radioactive isotope of the atom in question is present in levels at least 10% (e.g. from 10% to 5000%, particularly from 50% to 1000% and more particularly from 100% to 500%) above the natural level of that radioactive or non-radioactive isotope.

In embodiments of the invention, the formula Ia and Ib may be Ia' and Ib', respectively

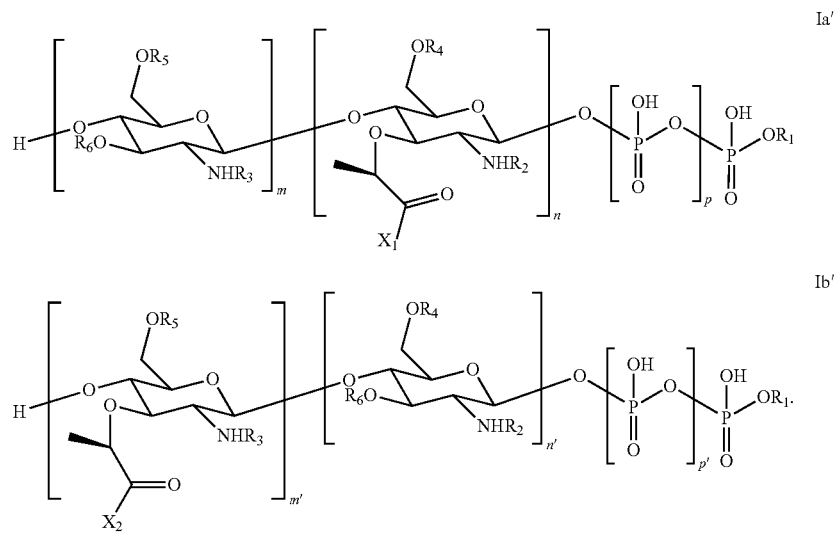

For the avoidance of doubt, the compounds of formula Ia' and Ib' may also be provided as pharmaceutically acceptable salts, solvates or prodrugs thereof.

In embodiments of the invention, when p and/or p' is 1 and $R_1$ represents $C_1$ to $C_{20}$ alkyl, then $R_8$ may represent a fluorescent group or a pharmaceutically active moiety. In such embodiments, the compounds of formula Ia and/or Ib (including compounds of formula Ia' and/or Ib') may be in a substrate configuration and so can carry a payload (i.e. a fluorescent group or a pharmaceutically active moiety). In alternative embodiments of the invention, when p and/or p' is 0 and $R_1$ represents —$CH_2CH(CO_2H)OC_{1-20}$ alkyl, then $R_8$ may represent H. In such embodiments, the compounds of formula Ia and/or Ib (including compounds of formula Ia' and/or Ib') may be in an inhibitor configuration and so do not necessarily need to carry a payload. However, it will be appreciated that compounds in the inhibitor configuration may still carry a suitable payload if desired (e.g. a pharmaceutically active moiety).

As will be appreciated, when used herein the pharmaceutically active moiety may be selected from any pharmaceutically active moiety that is capable of being covalently bonded to a compound described herein. In certain examples, this may require that the pharmaceutically active moiety, once covalently bound, retains potency against the target to which it is intended. Any suitable pharmaceutically active moiety may be used in compounds of formula Ia and/or Ib (and hence compounds of formula Ia' and/or Ib'), though it is preferred that each pharmaceutically active moiety selected herein is an antimicrobial agent. Examples of suitable antimicrobial agents that may be mentioned herein are described below.

As will be appreciated, when used herein the fluorescent group may be selected from any fluorescent group that is capable of being covalently bonded to a compound described herein. In certain examples, this may require that the fluorescent group, once covalently bound, retains its fluorescence. Any suitable fluorescent group may be used in compounds of formula Ia and/or Ib (and hence compounds of formula Ia' and/or Ib'). Examples of suitable fluorescent groups that may be mentioned herein are described below.

In further embodiments of the invention, when p and/or p' is 1, $R_1$ may represent $C_{10}$ to $C_{15}$ alkyl such as $C_{14}$ alkyl. In alternative embodiments of the invention, when p and/or p' is 0, $R_1$ may represent —$CH_2CH(CO_2H)OC_{10-15}$ alkyl, such as —$CH_2CH(CO_2H)OC_{12}$ alkyl.

Still further embodiments of the invention that may be mentioned include those that relate to compounds of formula Ia and/or Ib (and hence to compounds of formula Ia' and/or Ib') in which:
(aA) each $R_7$ may independently represent $C_1$ to $C_6$ alkyl;
(aB) $AA_1$ may be selected from $_L$-Ala, $_L$-Gly, or $_L$-Ser;
$AA_2$ may be selected from $_D$-isoglutamate (γ-$_D$-glutamate, γ-$_D$-Glu) or $_D$-isoglutamine;
$AA_3$ may be selected from $_L$-Lys, $_D$-Lys, $_L$-Orn or $_L$-2,4-diaminobutyrate, where the amino group is functionalised to become a $NHR_8$; and
$AA_4$ may be selected from $_D$-Ala or $_D$-Ser;
(aC) n may be from 5 to 25 and m may be from 4 to 25, provided that m has the same value as n or is n−1; n' may be from 5 to 25 and m' may be from 4 to 25, provided that m' has the same value as n' or is n'−1;
(aD) when a $R_8$ group is a fluorescent group, it may be selected from one or more of:

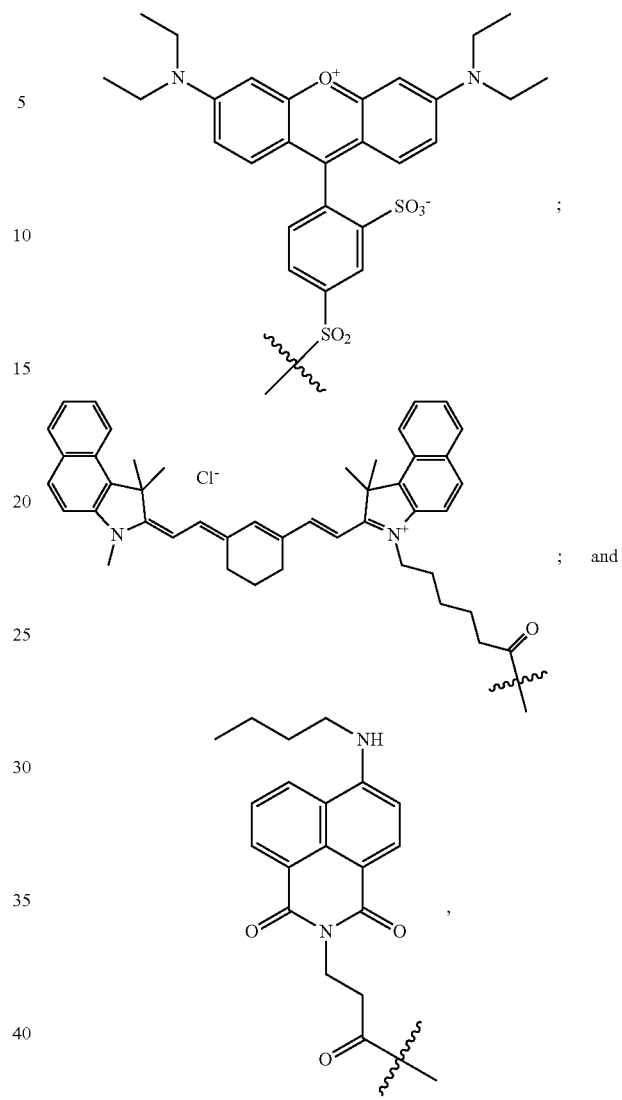

where the wavy line in each of the above moieties represents the point of attachment to the rest of the molecule;
(aE) when a $R_8$ group is a pharmaceutically active moiety, it may be selected from one or more of an antibiotic and an antigen moiety, where the point of attachment of the antibiotic and the antigen moiety to the rest of the molecule is through a $SO_2$ or C=O moiety.

Still further embodiments of the invention that may be mentioned include those that relate to compounds of formula Ia and/or Ib (and hence to compounds of formula Ia' and/or Ib') in which:
(Aa) each $R_7$ independently may represent $C_1$ alkyl;
(Ab) $AA_1$ may be $_L$-Ala;
$AA_2$ may be $_D$-isoglutamate (γ-$_D$-glutamate, γ-$_D$-Glu);
$AA_3$ may be selected from $_L$-Lys or $_L$-Orn (e.g. $_L$-Lys), where the amino group is functionalised to become a NH $R_8$ group; and
$AA_4$ may be D-Ala;
(Ac) n may be from 5 to 50 and m may be from 4 to 50, provided that m has the same value as n or is n−1; n' may be from 5 to 50 and m' may be from 4 to 50, provided that m' has the same value as n' or is n'−1, optionally wherein the sum of n+m or n'+m' is selected from one or more of 10, 25 or 50

(Ad) when a $R_8$ group is a fluorescent group, it may be selected from one or more of a rhodamine, a cyanine and a naphthalimide, where the point of attachment of the rhodamine, cyanine and naphthalimide to the rest of the molecule is through a $SO_2$ or C=O moiety;

(Ae) when a $R_8$ group is a pharmaceutically active moiety, it may be selected from one or more of:

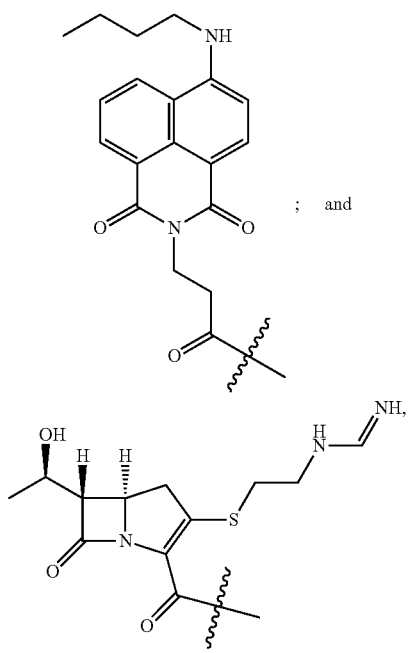
; and where the wavy line in each of the above moieties represents the point of attachment to the rest of the molecule.

For the avoidance of doubt, the term "$_D$-isoglutamate" is intended to refer to "γ-$_D$-glutamate" or "γ-D-Glu" having the structure:

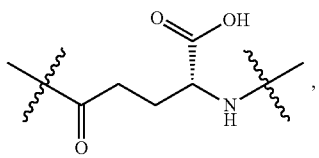 [SMILES: *N[C@H](CCC(*)=O)C(=O)O]
, when connected to other amino acids in the compounds of formula Ia and/or Ib (and hence compounds of Ia' and/or Ib'), with the wavy lines referring to the points of attachment to said other amino acids.

For the avoidance of doubt, it will be appreciated that each $R_8$ group in the compounds of formula Ia and/or Ib (and hence the compounds of formula Ia' and/or Ib') may be independently selected and so the same compound may contain multiple different pharmaceutically active moieties as well as multiple different fluorescent groups. In the case of having multiple active pharmaceutically active moieties, this may enable a single compound of formula Ia and/or Ib (or a compound of formula Ia' and/or Ib') to have broad-spectrum antimicrobial efficacy. In other embodiments, each $R_8$ group may be the same.

Embodiments of the invention that may be mentioned include those in which the compound of formula Ia and/or Ib (including compounds of formula Ia' and/or Ib') is a compound selected from the list:

(a)

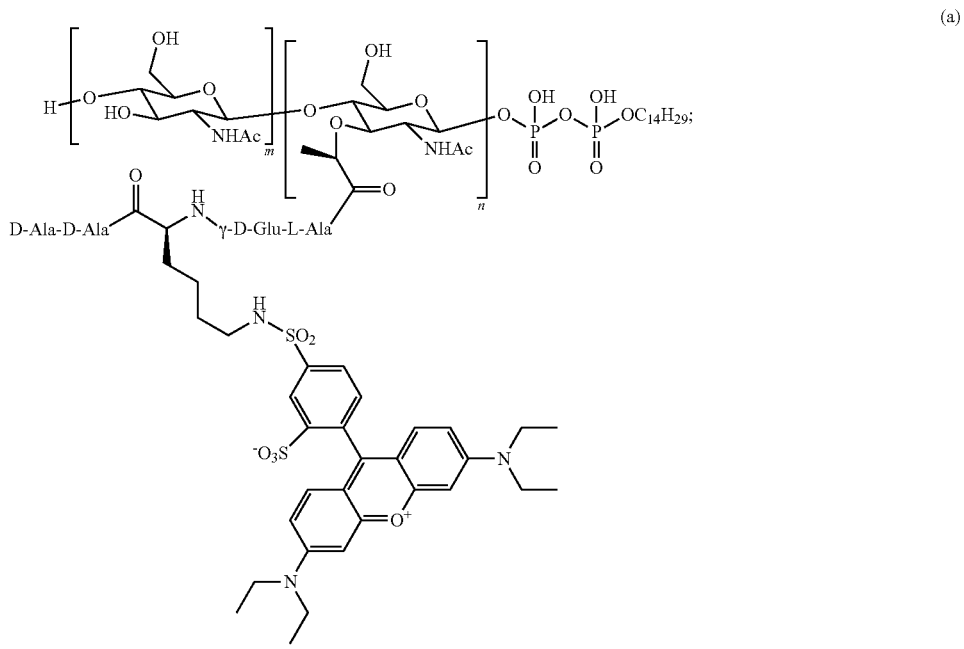

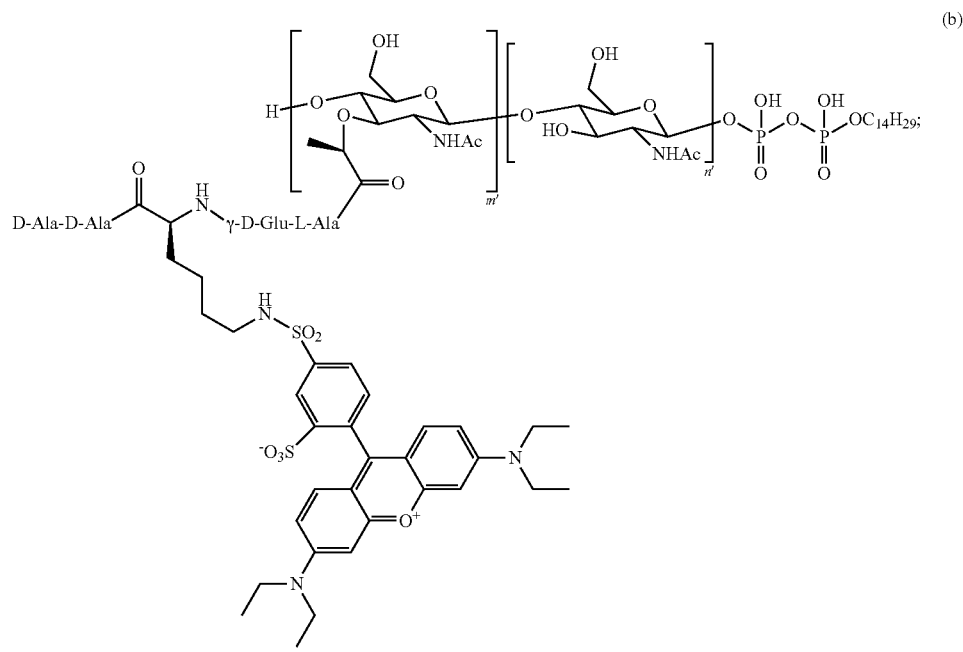
(b)
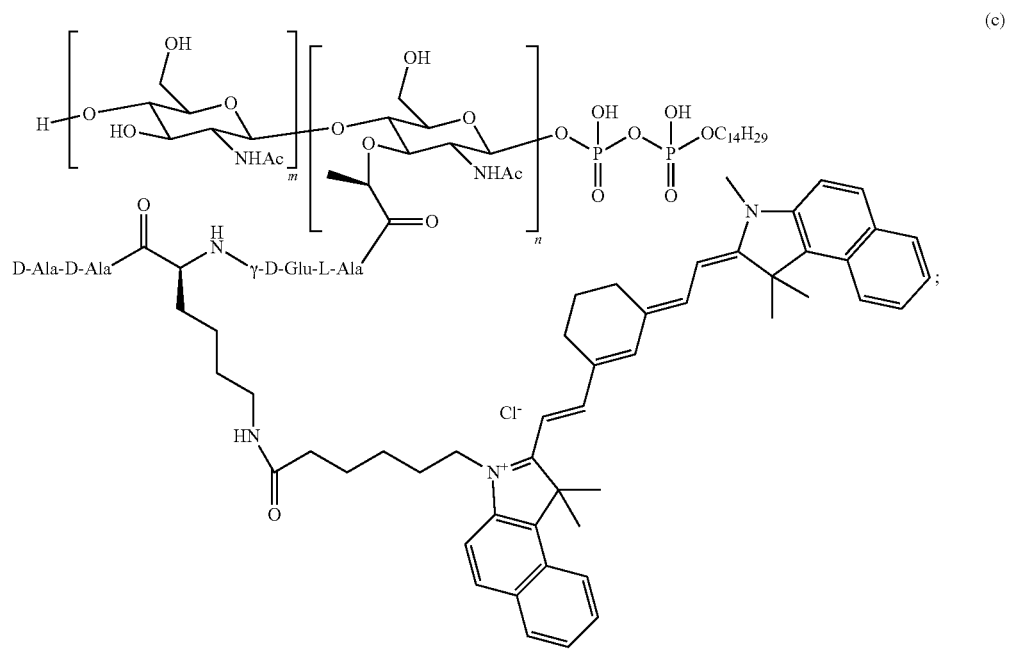
(c)

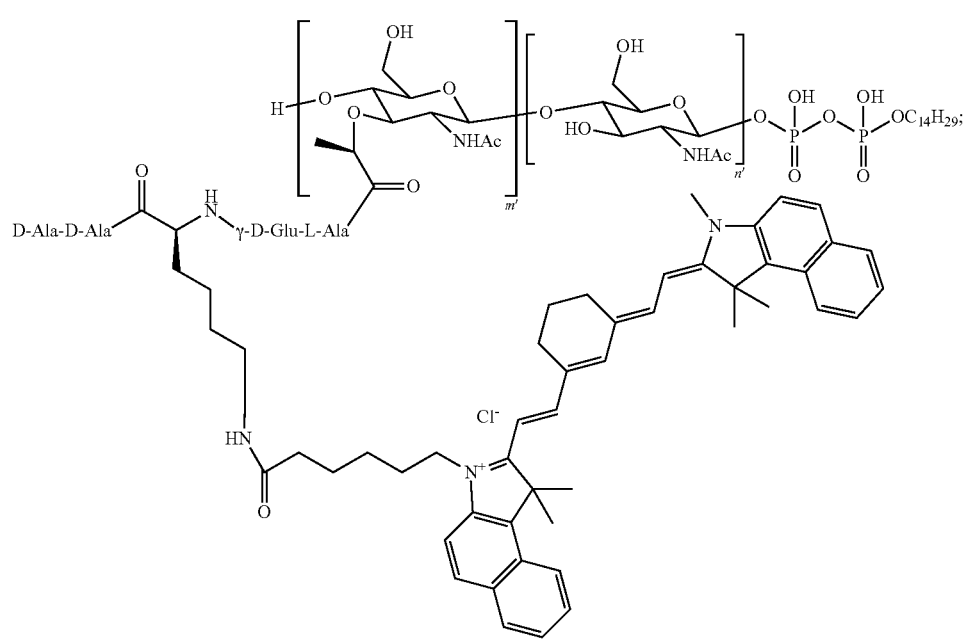
(d)
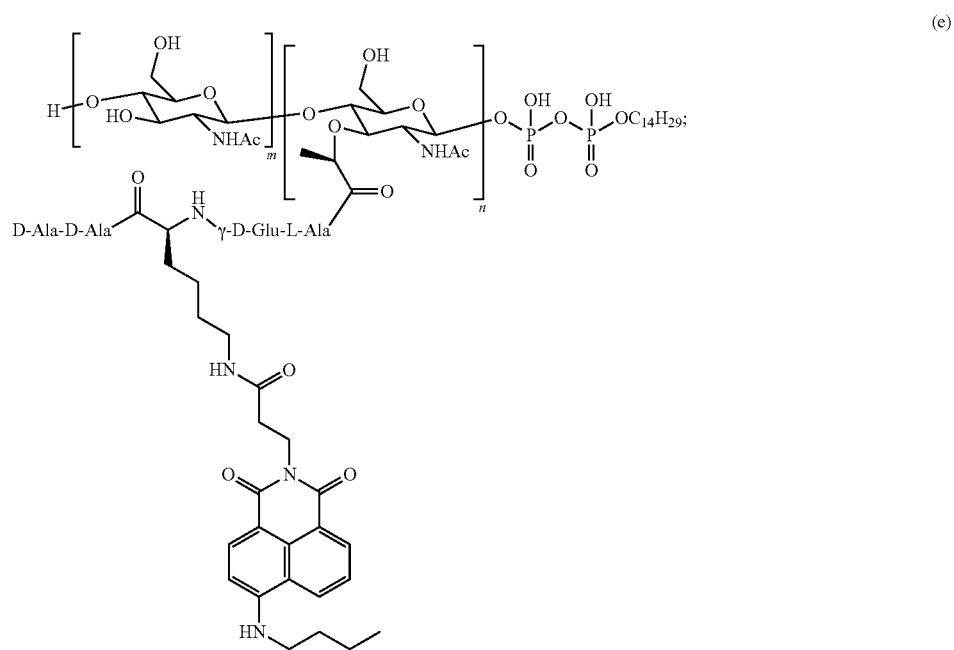
(e)

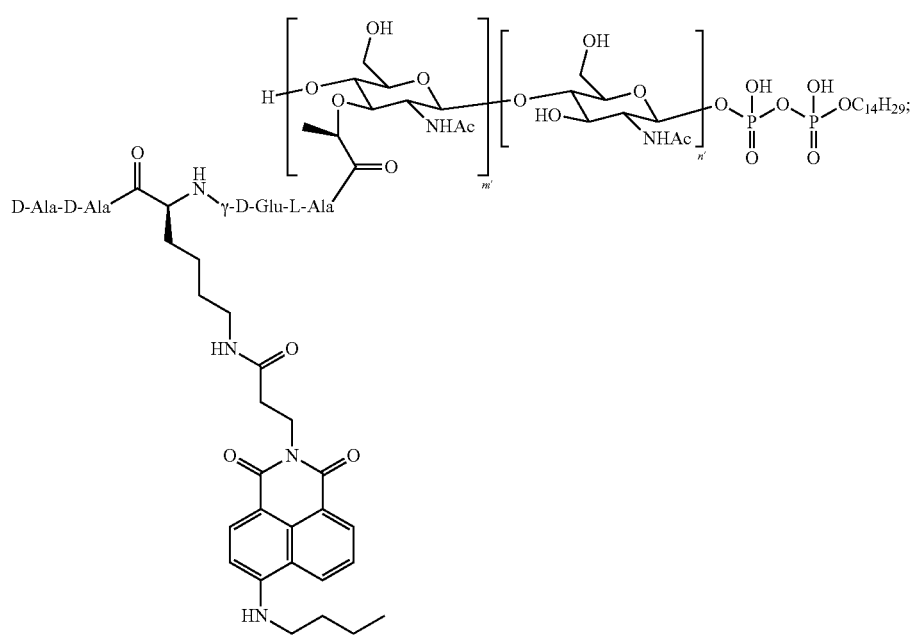
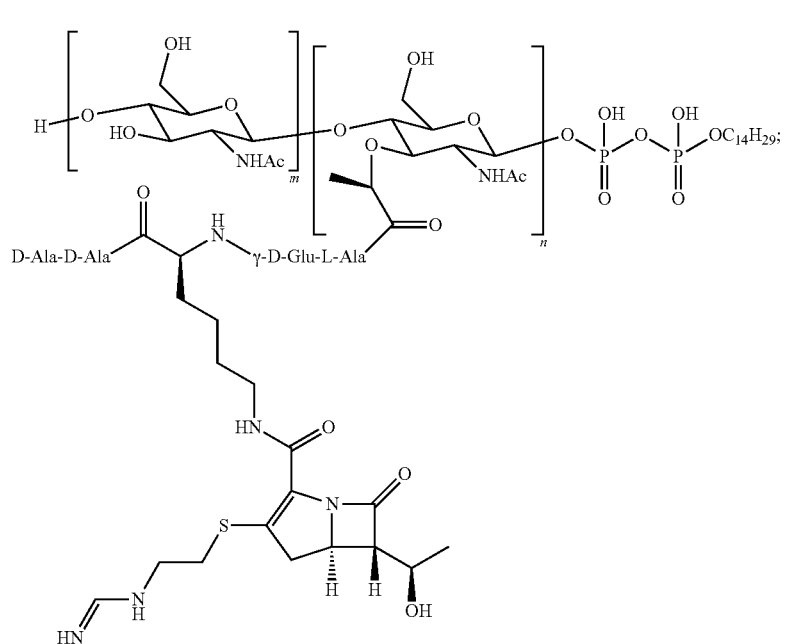

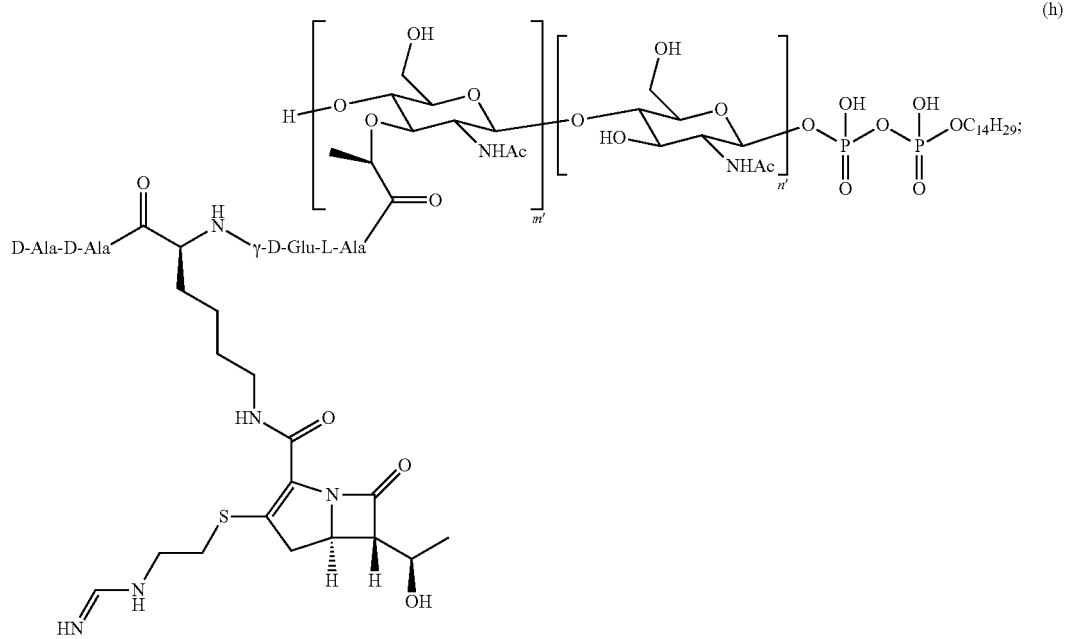
(h)
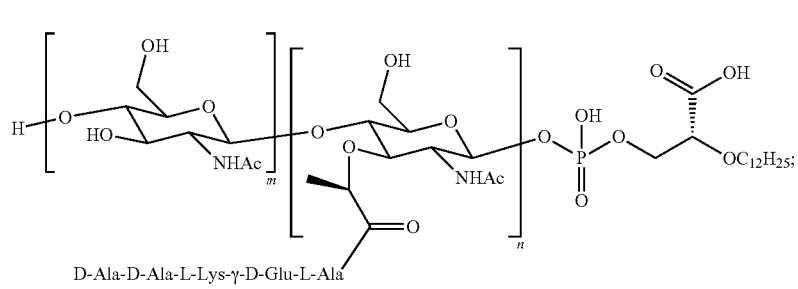
(i)
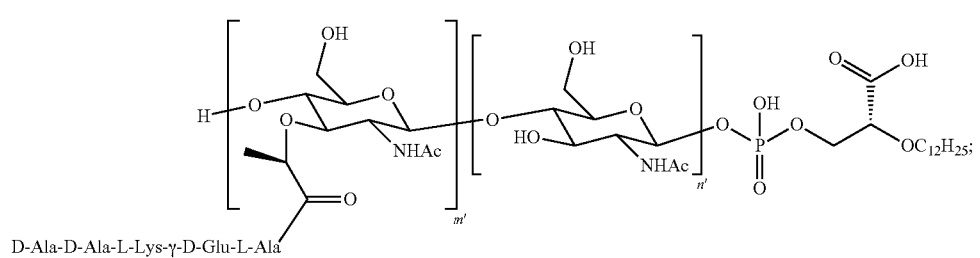
(j)
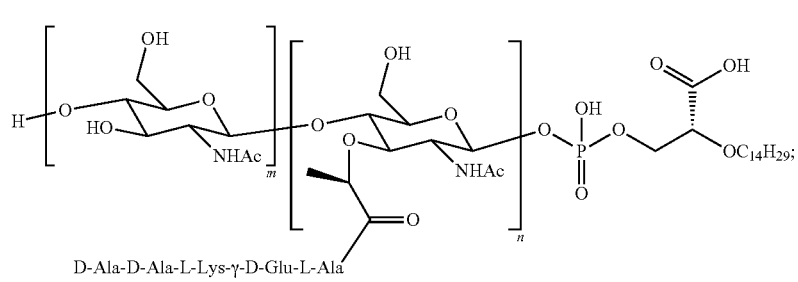
(k)

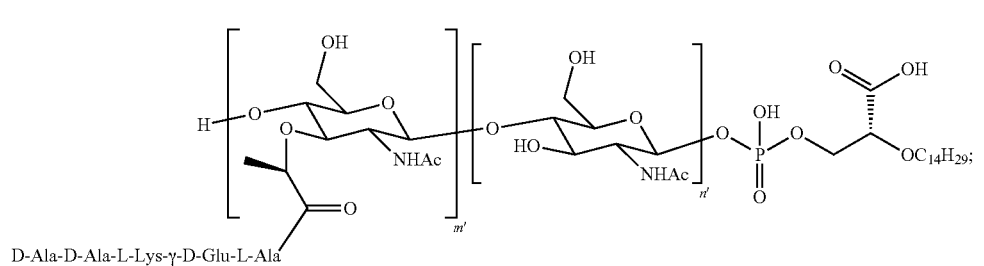
(l)
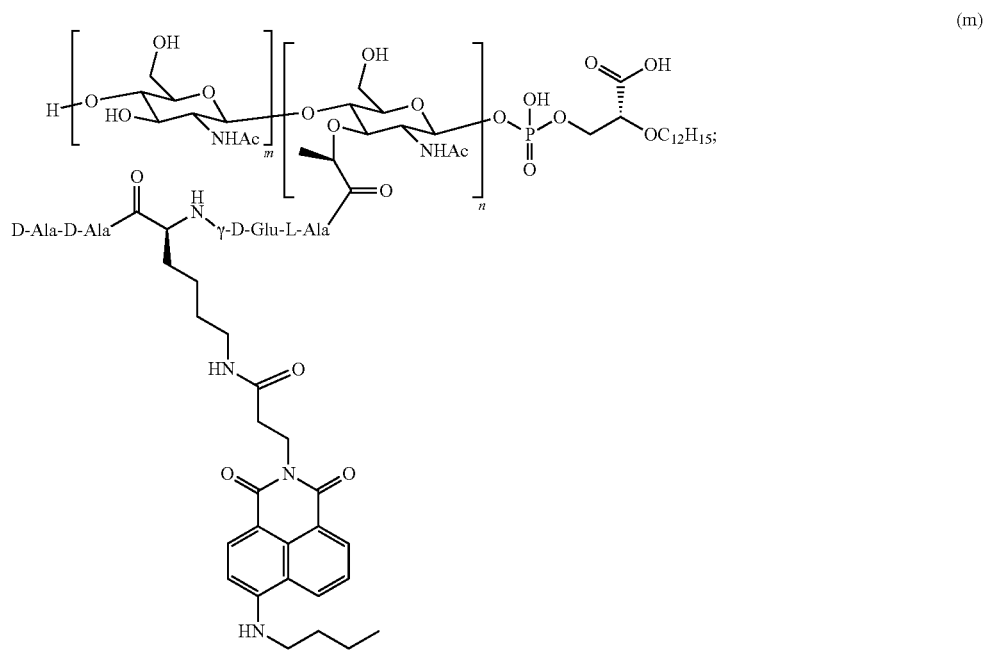
(m)
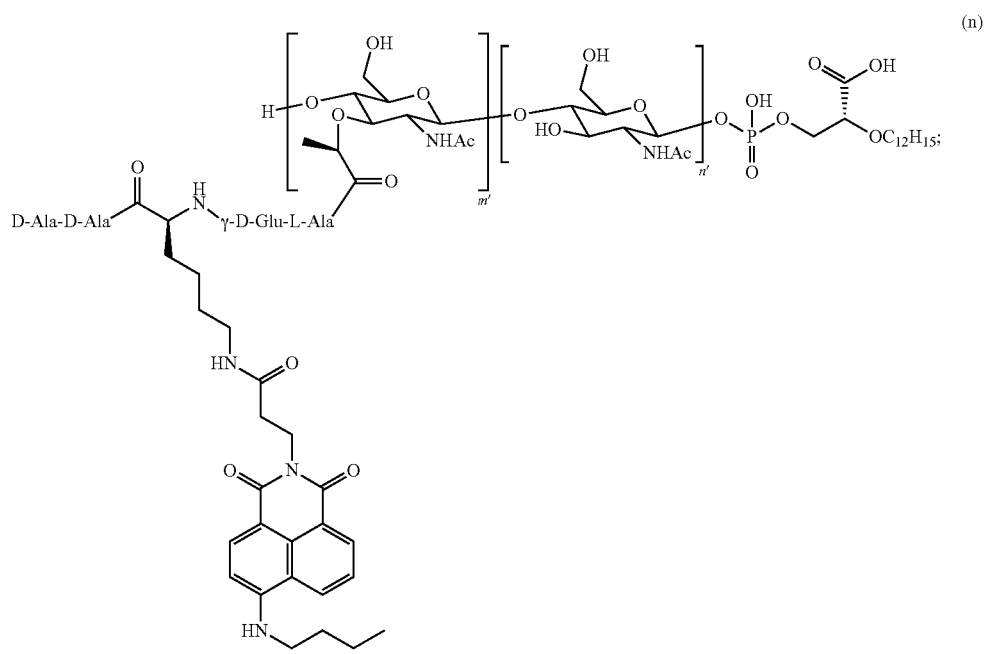
(n)

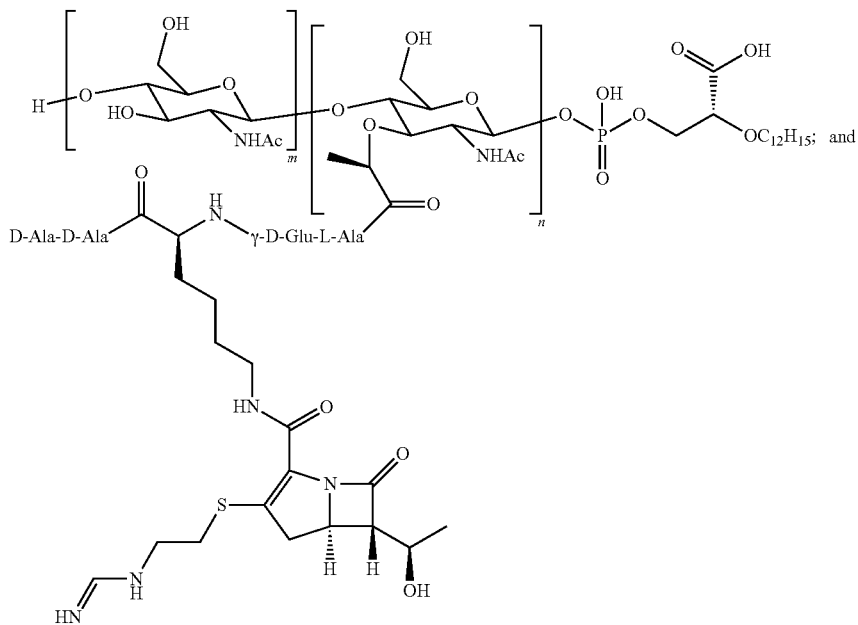

(o)

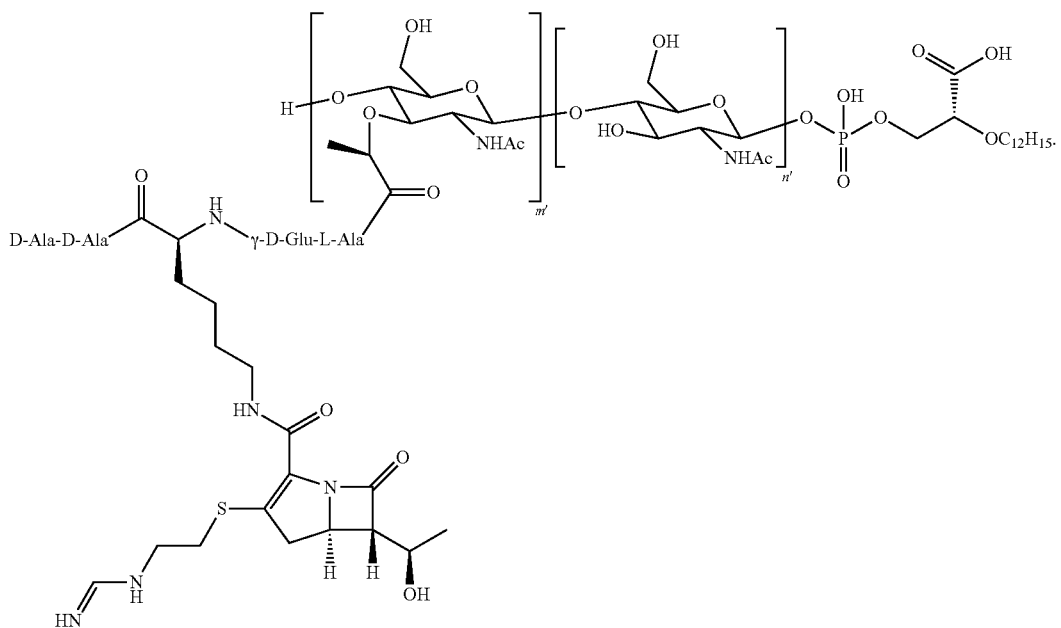

(p)

In embodiments of the invention that may be mentioned herein, the sum of n+m or n'+m' in the compounds disclosed in the list directly above may be selected from one or more of 10, 25 or 50.

Other compounds of formula Ia and/or Ib (including compounds of formula Ia' and/or Ib') that may be mentioned include the compounds of the examples described hereinafter.

In a further aspect of the invention, there is provided a pharmaceutical formulation comprising a compound of formula Ia and/or formula Ib (or a compound of formula Ia' and/or Ib') as described above and a pharmaceutically acceptable excipient, diluent or carrier.

Compounds of formula Ia and/or Ib (including compounds of formula Ia' and/or Ib') may be administered by any suitable route, but may particularly be administered orally, intravenously, intramuscularly, cutaneously, subcutaneously, transmucosally (e.g. sublingually or buccally), rectally, transdermally, nasally, pulmonarily (e.g. tracheally or bronchially), topically, by any other parenteral route, in the form of a pharmaceutical preparation comprising the compound in a pharmaceutically acceptable dosage form. Particular modes of administration that may be mentioned include oral, intravenous, cutaneous, subcutaneous, nasal, intramuscular or intraperitoneal administration.

Compounds of formula Ia and/or Ib (including compounds of formula Ia' and/or Ib') will generally be administered as a pharmaceutical formulation in admixture with a pharmaceutically acceptable adjuvant, diluent or carrier, which may be selected with due regard to the intended route of administration and standard pharmaceutical practice. Such pharmaceutically acceptable carriers may be chemically inert to the active compounds and may have no detrimental side effects or toxicity under the conditions of use. Suitable pharmaceutical formulations may be found in, for example, Remington *The Science and Practice of Pharmacy*, 19th ed., Mack Printing Company, Easton, Pa. (1995). For parenteral administration, a parenterally acceptable aqueous solution may be employed, which is pyrogen free and has requisite pH, isotonicity, and stability. Suitable solutions will be well known to the skilled person, with numerous methods being described in the literature. A brief review of methods of drug delivery may also be found in e.g. Langer, *Science* (1990) 249, 1527.

Otherwise, the preparation of suitable formulations may be achieved routinely by the skilled person using routine techniques and/or in accordance with standard and/or accepted pharmaceutical practice.

The amount of compound of formula Ia and/or Ib (including a compound of formula Ia' and/or Ib') in any pharmaceutical formulation used in accordance with the present invention will depend on various factors, such as the severity of the condition to be treated, the particular patient to be treated, as well as the compound(s) which is/are employed. In any event, the amount of compound of formula Ia and/or Ib (including a compound of formula Ia' and/or Ib') in the formulation may be determined routinely by the skilled person.

For example, a solid oral composition such as a tablet or capsule may contain from 1 to 99% (w/w) active ingredient; from 0 to 99% (w/w) diluent or filler; from 0 to 20% (w/w) of a disintegrant; from 0 to 5% (w/w) of a lubricant; from 0 to 5% (w/w) of a flow aid; from 0 to 50% (w/w) of a granulating agent or binder; from 0 to 5% (w/w) of an antioxidant; and from 0 to 5% (w/w) of a pigment. A controlled release tablet may in addition contain from 0 to 90% (w/w) of a release-controlling polymer.

A parenteral formulation (such as a solution or suspension for injection or a solution for infusion) may contain from 1 to 50% (w/w) active ingredient; and from 50% (w/w) to 99% (w/w) of a liquid or semisolid carrier or vehicle (e.g. a solvent such as water); and 0-20% (w/w) of one or more other excipients such as buffering agents, antioxidants, suspension stabilisers, tonicity adjusting agents and preservatives.

For the avoidance of doubt, in the context of the present invention, the term "treatment" includes references to therapeutic or palliative treatment of patients in need of such treatment, as well as to the prophylactic treatment and/or diagnosis of patients which are susceptible to the relevant disease states.

The terms "patient" and "patients" include references to mammalian (e.g. human) patients. As used herein the terms "subject" or "patient" are well-recognised in the art, and, are used interchangeably herein to refer to a mammal, including dog, cat, rat, mouse, monkey, cow, horse, goat, sheep, pig, camel, and, most preferably, a human. In some embodiments, the subject is a subject in need of treatment or a subject with a disease or disorder. However, in other embodiments, the subject can be a normal subject. The term does not denote a particular age or sex. Thus, adult and newborn subjects, whether male or female, are intended to be covered.

As will be appreciated, the compounds of formula Ia and/or formula Ib (or compounds of formula Ia' and/or Ib') described herein may be used in medicine, for example in the treatment of a subject or in diagnosis/identification of a microbial infection. Thus, there is provided a use of a compound of formula Ia and/or formula Ib (or a compound of formula Ia' and/or Ib') as described above or a pharmaceutically acceptable salt, solvate or prodrug thereof, in medicine.

As noted above, the compounds formula Ia and/or formula Ib (or the compounds of formula Ia' and/or Ib') described herein may be used in the treatment of a microbial infection. Thus there is provided a:

(Ai) use of a compound of formula Ia and/or formula Ib (or a compound of formula Ia' and/or Ib') as described above where $R_8$ is a pharmaceutically active moiety, or a pharmaceutically acceptable salt, solvate or prodrug thereof, in the preparation of a medicament for treating a microbial infection;

(Aii) compound of formula Ia and/or formula Ib (or a compound of formula Ia' and/or Ib') as described above where $R_8$ is a pharmaceutically active moiety, or a pharmaceutically acceptable salt, solvate or prodrug thereof, for use in the treatment of a microbial infection;

(Aiii) method of treatment of a microbial infection comprising administering a pharmaceutically effective amount of a compound of formula Ia and/or formula Ib (or a compound of formula Ia' and/or Ib') as described above where $R_8$ is a pharmaceutically active moiety, or a pharmaceutically acceptable salt, solvate or prodrug thereof, to a subject in need thereof.

Examples of compounds having an $R_8$ group containing a pharmaceutically active moiety include those disclosed as compounds (e) to (p) in the list of compounds above.

Depending on the disorder, and the patient, to be treated, as well as the route of administration, compounds of formula Ia and/or Ib (including compounds of formula Ia' and/or Ib') may be administered at varying therapeutically effective doses to a patient in need thereof.

However, the dose administered to a mammal, particularly a human, in the context of the present invention should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Administration may be continuous or intermittent (e.g. by bolus injection). The dosage may also be determined by the timing and frequency of administration. In the case of oral or parenteral administration the dosage can vary from about 0.01 mg to about 1000 mg per day of a compound of formula I.

In any event, the medical practitioner, or other skilled person, will be able to determine routinely the actual dosage, which will be most suitable for an individual patient. The above-mentioned dosages are exemplary of the average case; there can, of course, be individual instances where higher or lower dosage ranges are merited, and such are within the scope of this invention.

As noted above, the compounds formula Ia and/or formula Ib (or a compound of formula Ia' and/or Ib') described herein may be used in the detection of a microbial infection. Thus there is provided a:

(Bi) use of a compound of formula Ia and/or formula Ib (or a compound of formula Ia' and/or Ib') as described above where R$_8$ is a fluorescent group, or a pharmaceutically acceptable salt, solvate or prodrug thereof, in the preparation of a medicament for detecting a microbial infection in a subject, wherein following administration of the compound of formula Ia and/or formula Ib to the subject and irradiation of the subject with light, a microbial infection is detected by the presence of fluorescence;

(Bii) compound of formula Ia and/or formula Ib (or a compound of formula Ia' and/or Ib') as described above where R$_8$ is a fluorescent group, or a pharmaceutically acceptable salt, solvate or prodrug thereof, for use in detecting a microbial infection in a subject, wherein following administration of the compound of formula Ia and/or formula Ib (or a compound of formula Ia' and/or Ib') to the subject and irradiation of the subject with light, a microbial infection is detected by the presence of fluorescence;

(Biii) method of detecting a microbial infection in a subject comprising administering a pharmaceutically effective amount of a compound of formula Ia and/or formula Ib (or a compound of formula Ia' and/or Ib') where R$_8$ is a fluorescent group, or a pharmaceutically acceptable salt, solvate or prodrug thereof, to a subject, subsequently exposing the subject to light irradiation and detecting a microbial infection by the presence of fluorescence.

Examples of compounds having an R$_8$ group containing a fluorescent group include those disclosed as compounds (a) to (f) in the list of compounds above. It will be appreciated that compounds of formula Ia and/or formula Ib (and hence compounds of formula Ia' and/or Ib') where R$_8$ is a fluorescent group may also be useful in determining the antimicrobial resistance profile of a particular microorganism (or group of microorganisms). Thus, there is also disclosed a method of determining antimicrobial resistance of a microbial infection in a sample in vitro, the method comprising the steps of:

(A) contacting the sample with an antimicrobial to provide an antimicrobial sample;
(B) contacting the antimicrobial sample after a period of time with a compound of formula Ia and/or formula Ib (or a compound of formula Ia' and/or Ib') as described above where R$_8$ is a fluorescent group, or a pharmaceutically acceptable salt, solvate or prodrug thereof; and
(C) detecting fluorescence produced by the fluorescent group upon exposure to a light source, wherein
detection of fluorescence is used to determine antimicrobial resistance.

In such embodiments, the method may be conducted in parallel or series, such that multiple samples are subjected to steps (A) to (C) with a plurality of individual antimicrobials and/or combinations of antimicrobials to determine the antimicrobial resistance profile of the microbial infection. It will be appreciated that the period of time in step (B) may be chosen by a person skilled in the art based on their normal skill and experience. For example, the period of time in step (B) above may be from 5 minutes to 24 hours, such as 30 minutes to 12 hours, such as 45 minutes to 6 hours, such as 1 hour.

Furthermore, the compounds of formula Ia and/or Ib (and hence the compounds of formula Ia' and/or Ib') may be useful in helping to determine the dose of an antimicrobial agent that is required to effectively kill a microorganism (or a group of microorganisms). As such, there is also provided a method of determining an effective dose of one or more antimicrobial agents to kill a microorganism, the method comprising the steps of:

(iA) contacting one or more antimicrobial test solutions comprising one or more antimicrobial agents with the microorganism to provide one or more test samples, when there are two or more test samples, the concentration of each of the one or more antimicrobial agents is varied between the two or more antimicrobial test solutions to define a range;
(iB) contacting each of the one or more test samples after a period of time with a compound of formula Ia and/or formula Ib as described in any one of claims 1 to 10 and 13(a) to 13(f) where R$_8$ is a fluorescent group, or a pharmaceutically acceptable salt, solvate or prodrug thereof; and
(iC) detecting fluorescence produced by the fluorescent group upon exposure to a light source in each of the test samples, wherein
detection of fluorescence in a test sample indicates the concentration of the one or more antimicrobial agents in said antimicrobial test solution is not effective, and the lack of detection of fluorescence indicates the concentration of the one or more antimicrobial agents in said antimicrobial test solution is effective, thereby determining the effective dose of the one or more antimicrobial agents.

It will be appreciated that the period of time in step (iB) may be chosen by a person skilled in the art based on their normal skill and experience. For example, the period of time in step (iB) above may be from 5 minutes to 24 hours, such as 30 minutes to 12 hours, such as 45 minutes to 6 hours, such as 1 hour.

Finally, there is also disclosed a method of making a compound of formula Ia and/or Ib (or a compound of formula Ia' and/or Ib') as described above, wherein the compound(s) is obtained and/or obtainable from a chitosan molecule comprising from 9 to 100 sugar units, such as from 10 to 50 sugar units, such as 10 to 25 sugar units. Further details of this method are described in the examples. It will be appreciated that the experimental details described herein, when combined with a skilled person's chemical knowledge, can be used to make any compound falling with the scope of the claims hereinbelow. When used herein, the term "chitosan" may refer to chitosan per se, but it may also refer to derivatives thereof, such as chitin. In particular embodiments of the invention that may be mentioned herein, the term "chitosan" may refer to chitosan per se.

Further aspects and embodiments of the invention will now be described by reference to the following non-limiting examples.

EXAMPLES

The current invention relates to a compound, such as biohybrid peptidoglycan oligomer (PGO).

In an embodiment of the invention, the compound is PGO 1 as shown in FIG. 3. Applying retrosynthetic analysis, PGO 1 can be broken down into the lipid subunit (added to 2 after glycosylation of 3), the pentapeptide subunit (added to 3 to form 4), and the NAG-NAM oligomer (derivatised as 5). For clarity, only a disaccharide unit (NAG-NAM) is shown in 1 through 8 to demonstrate the chemical transformations as described below. It is understood that said transformations also take place at the remaining NAG-NAM units in the oligomer, which are represented by ( . . . -) which is attached to the C4 position of the NAG.

The most challenging aspect of biohybrid synthesis of PGOs is deriving the characteristic alternating pattern of NAG-NAM sugar chains in 5 from the homogeneously repeating sugar units in regular polysaccharides. In the past, this difficulty has hindered the usage of naturally available polysaccharides as substrates for the synthesis of PGOs, or other more complex sugars. As shown in FIG. 3, to get to 5, capping of all hydroxyls on 6 should be done after converting the NAG oligomer derivative 7 into the NAG-NAM oligomer derivative, i.e. add lactate groups onto NAG oligomers' C-3 position in an alternating fashion. To achieve this, the bulky phthaloyl and triisopropylsilyl protecting groups was selected to block all the NAG carbons in chitosan, except at each NAG's C-3 position, as seen in substrate 7. Each 2-bromopropanoate addition at the C-3 position would then hinder 2-bromopropanoate addition at the immediate neighbor C-3 positions, due to the steric hindrance and hydrogen-bonding associated with each propanoate group. Thus, in the presence of optimal amounts of 2-bromopropanoate reagent, an alternating pattern of propanoate-linked NAG units, i.e. NAG-NAM oligomers, as derivatised in substrate 5 will be kinetically and thermodynamically favored. Low molecular weight chitosan 9 is a good choice of the starting polysaccharide, not only because it is readily available and consists of soluble glucosamine-glucosamine oligomers but, also more importantly, the more reactive C-2 amino group in glucosamine presents a good handle to differentiate between the sugar C-2 and C-3 positions, to produce substrate 7 (FIG. 3). The procedure to prepare PGO 1 is described in detail in the examples below.

Materials and Methods

The materials were purchased from the sources as provided below.

Chitosan (Mw 3000 Da, 5000 Da, 10000 Da, degree of deacetylation >85%) were purchased from Carbosynth Ltd. (Berkshire, UK). 1N-(3-Dimethylaminopropyl)-N'-ethylcarbodiimide hydrochloride (EDCl), 1-[Bis(dimethylamino)methylene]-1H-1,2,3-triazolo[4,5-b]pyridinium 3-oxid-hexafluoro-phosphate (HATU), 3H-[1,2,3]-Triazolo[4,5-b]pyridin-3-ol (HOAt), and all amino acids used in synthesis were purchased from GL Biochem Ltd. (Shanghai, China). Membrane dye FM 1-43fx was purchased from Thermo Fisher Scientific Inc. (Waltham, USA). All other chemicals used in synthesis were purchased from Sigma-Aldrich Co. LLC. (St. Louis, USA).

Bacterial strains (*Escherichia coli* ATCC 29425, *Pseudomonas aeruginosa* ATCC 27853, methicillin-resistant *Staphylococcus aureus* ATCC BAA-40 and ATCC 1556, *Enterococcus faecalis* ATCC 700802, and *Bacillus Subtilis* ATCC 6633) were purchased from the American Type Culture Collection (Manassas, USA) and stored at −80° C. Mueller-Hinton broth (MHB, Difco), brain heart infusion broth (BHI, Difco) and trypticase soy broth (TSB, Difco) were purchased from Beckton, Dickinson and company (Franklin Lakes, USA).

Dialysis tubing was purchased from Spectra/Por (Singapore).

The reactions were all performed under nitrogen atmosphere. Starting materials and reagents were all purchased commercially and used as received. Solvents used in reactions were all purified according to standard procedures in literature. Thin layer chromatography (TLC) with Merck TLC silica gel 60 F254 plate was used to check reaction progress. UV, or potassium permanganate staining if necessary, was used to visualize compounds on TLC plates. Flash column chromatography with silica gel 60 (0.010-0.063 mm) and gradient solvent system was used to isolate products. 1H and 13C NMR spectra were obtained using 400 MHz Bruker AVIII 400 spectrometer or 500 MHz Bruker AV 500 spectrometer. Tetramethylsilane (TMS) was used as internal standard in measurement of chemical shifts (ppm). Multiplicities were reported as s (singlet), d (doublet), t (triplet), q (quartet), m (multiplet or unsolved), br s (broad singlet) or dd (doublet of doublets). The number of protons (n) corresponding to a resonance signal was indicated as nH and coupling constants were reported as J values in units of Hz. Characterisation data for known compounds were checked in comparison with literature for consistency and not presented in this report. Polymeric substrates were purified by dialysis using a dialysis tubing cellulose membrane (3.5 kDa molecular weight cut-off (MWCO)) for 2 days. Shimadzu LCsolution and Kromasil 100-5C8 reverse phase column was used for high-performance liquid chromatography (HPLC) analysis with deuterium lamp at 280 nm.

General Procedure 1: Synthesis of Polymer 5 from Chitosan

Polymer/substrate 5 was prepared from chitosan making use of previously reported protocols. Protection of chitosan was done following Ifuku et al (*Green Chem.* 2011, 13, 1499-1502) and Gagnon et al (Biomacromolecules, 2007, 8, 1812-1815). Calculations are based on repeating monosaccharide units on the oligomers.

As a brief summary, starting from (e.g. a low molecular weight) chitosan 9, the C-2 free amino groups were protected with phthaloyl group so as to protect them from subsequent transformation. Subsequently, the primary alcohols and anomeric hydroxyl group group at the reducing terminal were protected by the bulky protecting group triisopropylsilyl group. The C-3 hydroxy groups on chitosan are relatively inert towards this reaction unless harsher conditions are applied. This results in the formation of substrate 7, where the C-3 hydroxyl groups remain unprotected. Next, 2-bromopropanoate was introduced at C-3 by $SN_2$ chemistry, with a molar ratio of 2:1 for glucosamine unit:2-bromopropanoate, approximating the alternating pattern of the peptidoglycan repeating motif, to give the desired substrate 6. It should be noted that compound 6 is actually a mixture of two compounds—the first having the propanoate group in the position illustrated in compound 6 in FIG. 3, while the other has it on the other hydroxyl group, which is shown as unreacted in FIG. 3. The remaining hydroxyl groups were then capped by acetyl esterification to give substrate 5.

An improvement in organic solvent solubility was noted along the protection scheme, from substrate 8 forming a dispersion in dimethylformamide (DMF), to substrate 5 dissolving in $CH_2Cl_2$ as well as other commonly used organic solvents.

Synthesis of Polymer 8

Chitosan 9 (2.0 g, 12.5 mmol; Mw 3000 Da, degree of deacetylation >85% from Carbosynth Ltd.) was dissolved in 100 mL mixture of $AcOH/H_2O$ (v/v, 1:9). Phthalic anhydride (5.6 g, 37.5 mmol) was then added and the solution was stirred at 120° C. for 24 hours before cooling down to room temperature. The solvent was removed under reduced pressure and the residue was washed with ethanol and diethyl ether to give product 8 (3.3 g, 88%) as an off white solid.

Synthesis of Polymer 7

Polymer 8 (1.5 g, 5 mmol) was dissolved in 100 mL DMF. Imidazole (2.7 g, 40 mmol) was added, followed by triisopropyl chloride (6.8 g, 35 mmol) dropwise at 0° C. The reaction mixture was slowly warmed up to room temperature and stirred for 48 hours before solvent was removed under reduced pressure. The residue was washed with ethanol and diethyl ether to give product 7 (1.7 g, 71%) as a yellow solid. $^1$H NMR (400 MHz, DMSO-d$_6$) δ 8.11-7.65 (m, 4H), 5.39-4.21 (m, 5H), 3.97-3.64 (m, 2H), 1.06-0.15 (m, 21H).

Synthesis of Polymer 6

Polymer 7 (0.96 g, 2 mmol) was dissolved in 20 mL DMF at 0° C. Sodium hydride (200 mg, 5 mmol) was added portionwise and then (S)-(−)-2-Bromopropionic acid (153 mg, 1 mmol) was added dropwise. The reaction mixture was slowly warmed up to room temperature and stirred for 48 hours before quenching with methanol. The solvent was removed under reduced pressure and the residue was washed with water and ethanol consecutively to give product 6 (0.69 g, 69%) as a yellow solid. $^1$H NMR (400 MHz, DMSO-d$_6$) δ 8.21-7.28 (m, 4H), 5.22-3.61 (m, 7H), 2.12-1.79 (m, 1H), 1.38-0.41 (m, 23H).

Synthesis of Polymer 5

Polymer 6 (0.50 g, 1 mmol) and 4-dimethylaminopyridine (244 mg, 2 mmol) were dissolved in 20 mL pyridine at 0° C. Acetic anhydride (510 mg, 5 mmol) was added to the solution dropwise with stirring. The reaction was slowly warmed up to room temperature and stirred for 48 hours. Then solvent was removed under reduced pressure and the residue was washed with saturated ammonium chloride solution, followed by water to give product 5 (0.46 g, 92%) as an off white solid. $^1$H NMR (400 MHz, DMSO-d$_6$) δ 8.26-7.28 (m, 4H), 5.22-3.62 (m, 7H), 2.12-1.79 (m, 2H), 1.38-0.41 (m, 23H).

General Procedure 2: Synthesis of Compound 12 (Pentapeptide)

The pentapeptide 12 for coupling to chitosan backbone was synthesised by a condensation reaction between Boc-Ala-D-iso-Glu(OBn)-OH and H-Lys(Fmoc)-D-Ala-D-Ala-OMe to provide 13, followed by Boc removal with hydrogen chloride (deprotection) to form 12 according to methods reported in literature (*J. Am. Chem. Soc.*, 2011, 133, 10748-10751). H-Lys(Fmoc)-D-Ala-D-Ala-OMe was in turn prepared from H-D-Ala-D-Ala-OH. Pentapeptide 12 was chosen as it is commonly found in *S. aureus* and *E. faecalis*, both of which are clinically-relevant strains that have developed antibiotic resistance. The protecting groups on side chain and terminal functionalities were selected to be Fmoc for amine and benzyl or methyl ester for carboxylic acids, so that global deprotection can be realised at the end of synthesis with lithium hydroxide (LiOH).

Synthesis and Characterisation of Compound Boc-Lys(Fmoc)-D-Ala-D-Ala-OMe

H-D-Ala-D-Ala-OH (320 mg, 2.00 mmol) was dissolved in 20 mL MeOH at 0° C. and acetyl chloride (785 mg, 10.0 mmol) was added dropwise. The reaction was stirred for 15 min before slowly warming up to room temperature and stirring overnight. After removing solvents in vacuo, the crude was dissolved in 10 mL anhydrous DMF followed by addition of N,N-diisopropylethylamine (DIPEA; 646 mg, 5.00 mmol). Subsequently, Boc-Lys(Fmoc)-OH (937 mg, 2.00 mmol), HOAt (408 mg, 3.00 mmol) and EDCl (575 mg, 3.00 mmol) were added and the mixture was stirred for 2 hours before pouring into 50 mL water. Then EtOAc (30 mL×2) was used for extraction and the combined organic layer was washed with water (50 mL×5), brine (50 mL) and dried with Na$_2$SO$_4$. The crude product was purified by flash column chromatography (50% CH$_2$Cl$_2$/EtOAc) to give compound Boc-Lys(Fmoc)-D-Ala-D-Ala-OMe as a white solid (0.99 g, 79%).

$^1$H NMR (400 MHz, DMSO-d$_6$) δ 8.18 (d, J=7.2 Hz, 1H), 7.99 (d, J=7.9 Hz, 1H), 7.88 (d, J=7.5 Hz, 2H), 7.68 (d, J=7.5 Hz, 2H), 7.41 (t, J=7.5 Hz, 2H), 7.33 (t, J=7.5 Hz, 2H), 7.25 (t, J=5.9 Hz, 1H), 6.92 (d, J=7.3 Hz, 1H), 4.40-4.15 (m, 6H), 3.60 (s, 3H), 2.95 (q, J=6.6 Hz, 2H), 1.63-1.06 (m, 21H). $^{13}$C NMR (101 MHz, DMSO-d$_6$) δ 173.22, 172.44, 172.24, 156.52, 155.94, 144.39, 141.19, 128.04, 127.49, 125.58, 120.56, 78.60, 65.65, 56.30, 55.36, 54.93, 52.31, 48.00, 47.92, 47.24, 32.56, 31.79, 30.06, 29.52, 28.61, 23.18, 18.64, 17.23. HRMS (ESI) calcd. for C33H45N4O8 [M+H]: 625.3237, found: 625.3237.

Synthesis and Characterisation of Compound 13, Boc-Ala-D-iso-Glu(OBn)-Lys(Fmoc)-D-Ala-D-Ala-OMe To a solution of Boc-Lys(Fmoc)-D-Ala-D-Ala-OMe (624 mg, 1.00 mmol) in 30 mL CH$_2$Cl$_2$ was added 5 mL 2.0 M HCl in Et$_2$O and the mixture was stirred at room temperature for 4 hours. After checking full consumption of Boc-Lys(Fmoc)-D-Ala-D-Ala-OMe by TLC, the solvent was removed in vacuo and the crude H-Lys(Fmoc)-D-Ala-D-Ala-OMe·HCl was used without further purification.

Boc-Ala-OSu (286 mg, 1.00 mmol) and H-D-Glu(OH)-OBn (237 mg, 1.00 mmol) were dissolved in 10 mL DMF and 2 mL saturated NaHCO$_3$ (aq.) solution was added to the mixture. After stirring at room temperature overnight, 30 mL water was added and pH of the solution was adjusted to 2 by careful addition of HCl. The solution was extracted with EtOAc (20 mL×2) and the combined organic layer was washed with 1 mM aq. HCl (30 mL×2), water (30 mL×2) and brine (30 mL). After drying over Na$_2$SO$_4$, the solvent was removed in vacuo and the crude Boc-Ala-D-iso-Glu(OBn)-OH was dissolved in 20 mL DMF.

To the crude Boc-Ala-D-iso-Glu(OBn)-OH solution was added DIPEA (388 mg, 3.00 mmol), crude H-Lys(Fmoc)-D-Ala-D-Ala-OMe·HCl, HATU (760 mg, 2.00 mmol) and HOAt (272 mg, 2.00 mmol). The mixture was stirred at room temperature overnight before 60 mL water was added. Then it was extracted with EtOAc (50 mL×2) and the combined organic layer was washed with water (80 mL×5) and brine (80 mL). After removing solvent in vacuo, the crude was purified by flash column chromatography (60% CH$_2$Cl$_2$/Acetone) to give compound 13 (730 mg, 77%) as a white solid.

$^1$H NMR (400 MHz, DMSO-d$_6$) δ 8.27 (d, J=7.8 Hz, 1H), 8.18 (d, J=7.5 Hz, 2H), 8.02 (d, J=7.2 Hz, 1H), 7.88 (d, J=7.5 Hz, 2H), 7.84 (d, J=7.5 Hz, 2H), 7.41 (t, J=7.5 Hz, 2H), 7.38-7.24 (m, 8H), 6.86 (d, J=7.7 Hz, 1H), 6.60 (t, J=5.9 Hz, 1H), 6.28 (d, J=1.5 Hz, 2H), 5.11 (s, 2H), 4.27 (dh, 3H), 4.15 (q, J=7.2 Hz, 1H), 4.02 (p, J=7.2 Hz, 1H), 3.59 (s, 3H), 2.88 (q, J=6.6 Hz, 2H), 2.19 (q, J=7.7 Hz, 2H), 1.97 (h, J=7.3, 6.6 Hz, 1H), 1.83 (dq, J=15.0, 8.4, 7.6 Hz, 1H), 1.65-0.97 (m, 24H). $^{13}$C NMR (101 MHz, DMSO-d$_6$) δ 173.49, 173.28, 172.52, 171.99, 157.77, 155.44, 143.03, 139.87, 137.88, 136.35, 129.38, 128.84, 128.43, 128.18, 127.74, 121.83, 120.48, 110.19, 78.54, 66.39, 53.50, 52.25, 52.04, 50.13, 48.07, 48.02, 31.85, 31.67, 30.06, 29.84, 28.63, 27.37, 23.11, 18.92, 18.40, 17.22. HRMS (ESI) calcd. for C48H63N6O12 [M+H]: 915.4504, found: 915.4513.

Example 1: Synthesis and Characterisation of Compound (or PGO 1, R=H)

Figure 3A:
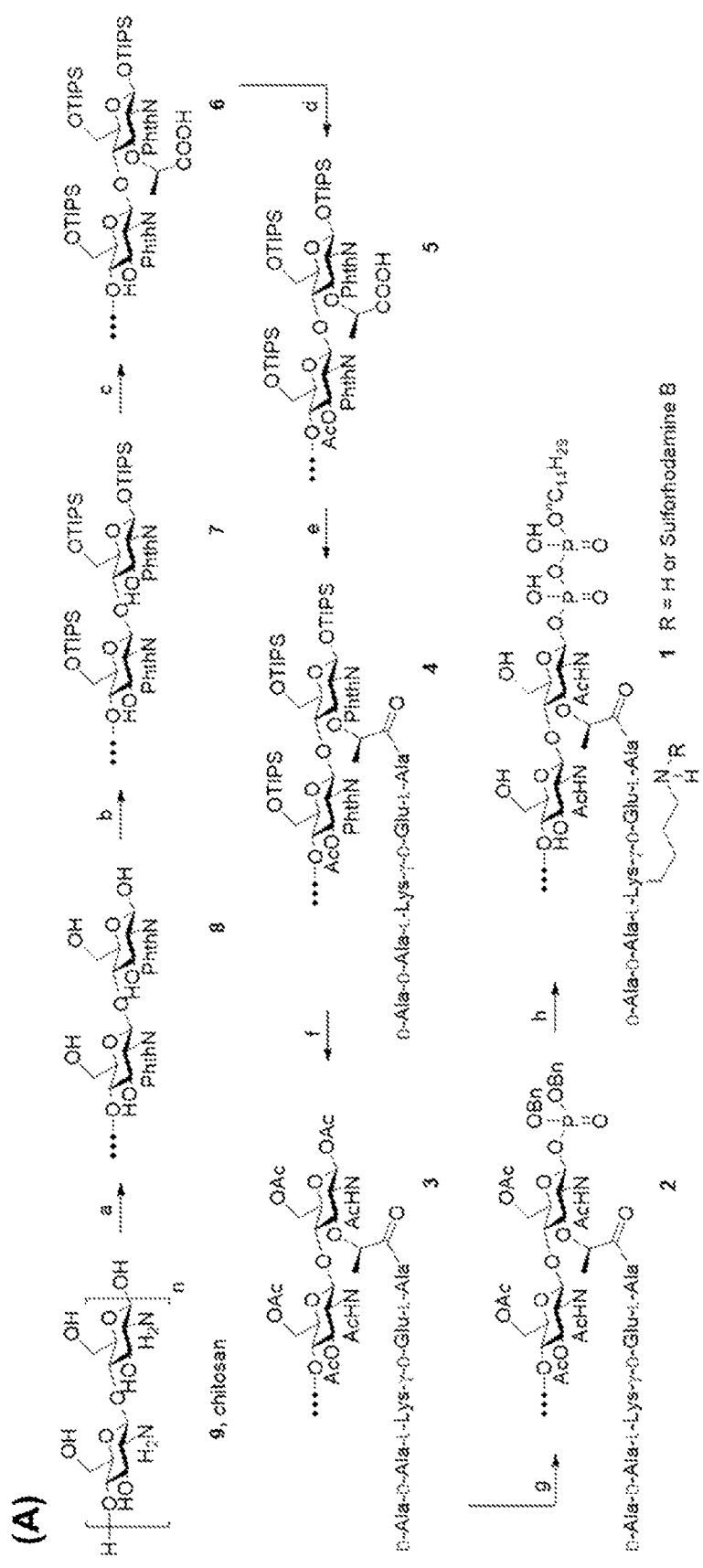

To prepare an unlabelled compound or PGO 1 (R=H, FIG. 3a), polymer 5 was directly linked to pentapeptide 12 under HATU/HOAt/DIPEA coupling conditions. Following partial cleavage and global protection with acetic anhydride, dibenzyl monophosphate was introduced at the reducing terminus. Hydrogenation was used to liberate the phosphate so that it can be coupled with a second lipid-linked monophosphate, to yield the desired oligosaccharide pyrophosphate 1 (FIG. 3a). The tetradecanyl lipid linker was chosen in place of the natural polyprenyl lipid to simplify preparation routes, taking into consideration that the tetradecanyl linker has been found to display a better binding affinity to MurG, one of the key PGTs (*Chem Bio Chem* 2003, 4, 603-609). The resulting crude mixture was dialysed with deionised water, filtered and lyophilised to furnish the pure oligomeric final product as a beige solid.

Synthesis of Polymer 4

To a solution of pentapeptide 12 (91 mg, 0.1 mmol; prepared according to General Procedure 2) in 20 mL $CH_2Cl_2$ was added 4 mL 2.0 M HCl in $Et_2O$ and the mixture was stirred at room temperature for 4 hours. After checking full consumption of 12 by TLC, the solvent was removed in vacuo and the crude H-Ala-D-iso-Glu(OBn)-Lys(Fmoc)-D-Ala-D-Ala-OMe·HCl was used without further purification. Polymer 5 (100 mg, 0.2 mmol; prepared according to General Procedure 1) and DIPEA (52 mg, 0.4 mmol) were dissolved in 25 mL DMF at room temperature. To the stirring solution was added HATU (190 mg, 0.5 mmol) and HOAt (68 mg, 0.5 mmol). After 5 min, the H-Ala-D-iso-Glu(OBn)-Lys(Fmoc)-D-Ala-D-Ala-OMe·HCl (170 mg, 0.2 mmol) was added and the reaction mixture was left stirring overnight. After removing solvent under reduced pressure, the residue was washed with saturated ammonium chloride solution and water to give product 4 (146 mg, 79%) as a brown solid. $^1$H NMR (400 MHz, DMSO-$d_6$) δ 8.20-7.51 (m, 10H), 5.82-3.83 (m, 12H), 3.61-2.99 (m, 4H) 2.47-1.72 (m, 5H), 1.48-0.59 (m, 30H).

Synthesis of Polymer 3

Polymer 4 (92 mg, 0.1 mmol) was dissolved in 30 mL methanol. Acetic acid (120 mg, 2 mmol), tetrabutylammonium fluoride (1.0 M tetrahydrofuran (THF) solution, 2.0 mL) and hydrazine (64 mg, 2 mmol) were added consecutively. The mixture was stirred at room temperature for 48 hours before solvent was removed under reduced pressure. The residue was washed with saturated ammonium chloride solution and water, then dried and redissolved in pyridine together with 4-dimethylaminopyridine (25 mg, 0.2 mmol). Acetic anhydride (51 mg, 0.5 mmol) was added to the solution dropwise at 0° C. with stirring. The reaction was slowly warmed up to room temperature and stirred for 48 h. Then solvent was removed under reduced pressure and the residue was washed with saturated ammonium chloride solution, followed by water to give product 3 as a yellow oil. The crude oil was used without further purification.

Synthesis of polymer 2

Crude polymer 3 was dissolved in 15 mL THF at 0° C. Methylamine (1.0 M THF solution, 0.3 mL) was added dropwise and the mixture was slowly warmed up to room temperature with stirring. After 24 hours, the solvent was removed under reduced pressure. The residue was washed with saturated ammonium chloride solution and water, then evaporated to dryness and dissolved in 30 mL dichloromethane. To this solution was added 1H-tetrazole (21 mg, 0.3 mmol) and dibenzyl N,N-diisopropylphosphoramidite (70 mg, 0.2 mmol) at 0° C. The mixture was warmed up and stirred at room temperature for 5 hours before cooling to −50° C. Then tert-butyl hydroperoxide (70%, 1 mL) was added and the mixture was left stirring overnight. After removing solvent under reduced pressure, the residue was washed with saturated ammonium chloride solution, saturated sodium bicarbonate solution and water to give product 2 as a yellow oil. The crude was used for next step without further purification.

Synthesis of 1

Tetradecyl monophosphate (59 mg, 0.2 mmol) was dissolved in 10 mL mixture of DMF and THF (v/v, 1:1) under room temperature. Then carbonyldiimidazole (CDI; 162 mg, 1 mmol) was added and the solution was stirred for 2 h before 1 mL dried methanol was added. The mixture was stirred for another 1 hour and dried to give activated tetradecyl phosphoroimidazolidate ($C_{14}$Plm).

To a solution of crude polymer 2 in 10 mL MeOH was added 8 mg Pd on activated charcoal. The suspension was stirred under $H_2$ atmosphere at room temperature overnight before filtration through a pad of celite. The solution was dried, and redissolved in 10 mL DMF before transferring to $C_{14}$Plm. Subsequently, 1H-tetrazole (14 mg, 0.2 mmol) was added and the mixture was stirred for 24 hours before evaporation to dryness. Then the residue was dispersed in 20 mL mixture of methanol and water (v/v, 1:1) and LiOH (1 M aqueous solution, 1 mL) was added. The mixture was stirred for 2 hours before dialysis and lyophilisation to give the final product 1 (50 mg, 50% for three steps from 4 to 1) as a beige solid.

The synthesis of 1 can be accomplished with 15% yield over eight one-pot reactions, which is much more efficient (and practical) compared to reported synthetic protocols. Each reaction can also be conducted at reasonable scale to lead to up to gram scale of 1 for each independent batch of synthesis.

Characterisation of PGO 1

The product's purity was analysed with reversed-phase HPLC and the molecular weight profile was characterised by Gel Permeation Chromatography (GPC), and confirmed by Dynamic Light Scattering (DLS).

HPLC analysis was performed using $NH_4OH$/MeOH from 0/100 to 10/90 in 60 min and 1 had a retention time of 7 min. Shimadzu LCsolution and Kromasil 100-5C8 reverse phase column was used for HPLC analysis with deuterium lamp at 280 nm.

Shodex SB-803 HQ and SB-805 HQ columns (Showa Denko, Tokyo, Japan) were connected in series for GPC in Agilent 1260 infinity system (Agilent, CA, USA). Samples were eluted at 0.5 mils through columns using 0.05 M NaCl in deionized water at 40° C. Light scattering was done using Malvern zetasizer (Malvern Instruments Ltd, Malvern, UK) For both HPLC and GPC, samples were dissolved in deionized water at 1 mg/mL before elution through columns. For DLS, samples were prepared at 100 μg/mL in deionized water and measured at 25° C. Backscattering at 173 degrees was adopted as the measuring angle.

As peak broadening was observed and the elution time was shorter than expected in the chromatogram of GPC, existence of secondary structures (self-assemblies with increased hydrodynamic radius) was inferred. This was confirmed by DLS of PGOs in solution, which showed nanoparticles of around 80 nm in diameter.
NMR The molecular structure of 1 was examined by NMR. Comparison of integration values from sugar, peptide and lipid moieties suggested a statistical ratio of 1:0.5:0.1, which totaled around 5 kDa molecular weight on average. This result confirms the desired outcome that half of the sugar repeating units of chitosan having a molecular weight of less than 3 kDA was grafted with the pentapeptide.
Lysozyme Degradation Assay and MS Analysis The finer structure of 1 was evaluated with a lysozyme degradation assay. Lysozyme binds to tetrasaccharides, or longer motifs, in peptidoglycan and cleaves the glycosidic linkages. The fragments were analysed with liquid chromatography-electrospray ionization ion-trap time-of-flight mass spectrometry (LC-ESI-TOF MS).

To prepare the crude product for mass analysis, 2 mg substrate 1 was dissolved in 0.2 mL 10 mM acetate buffer (pH=5.0) before addition of 0.4 mg lysozyme and incubation at 38° C. for 24 hours. Then the enzyme was pelleted by centrifugation at 1,500×g for 5 min, and the solution of crude metabolites was collected, diluted to 2 mL with 0.1% formic acid in deionised water and analysed.

Figure 3B:
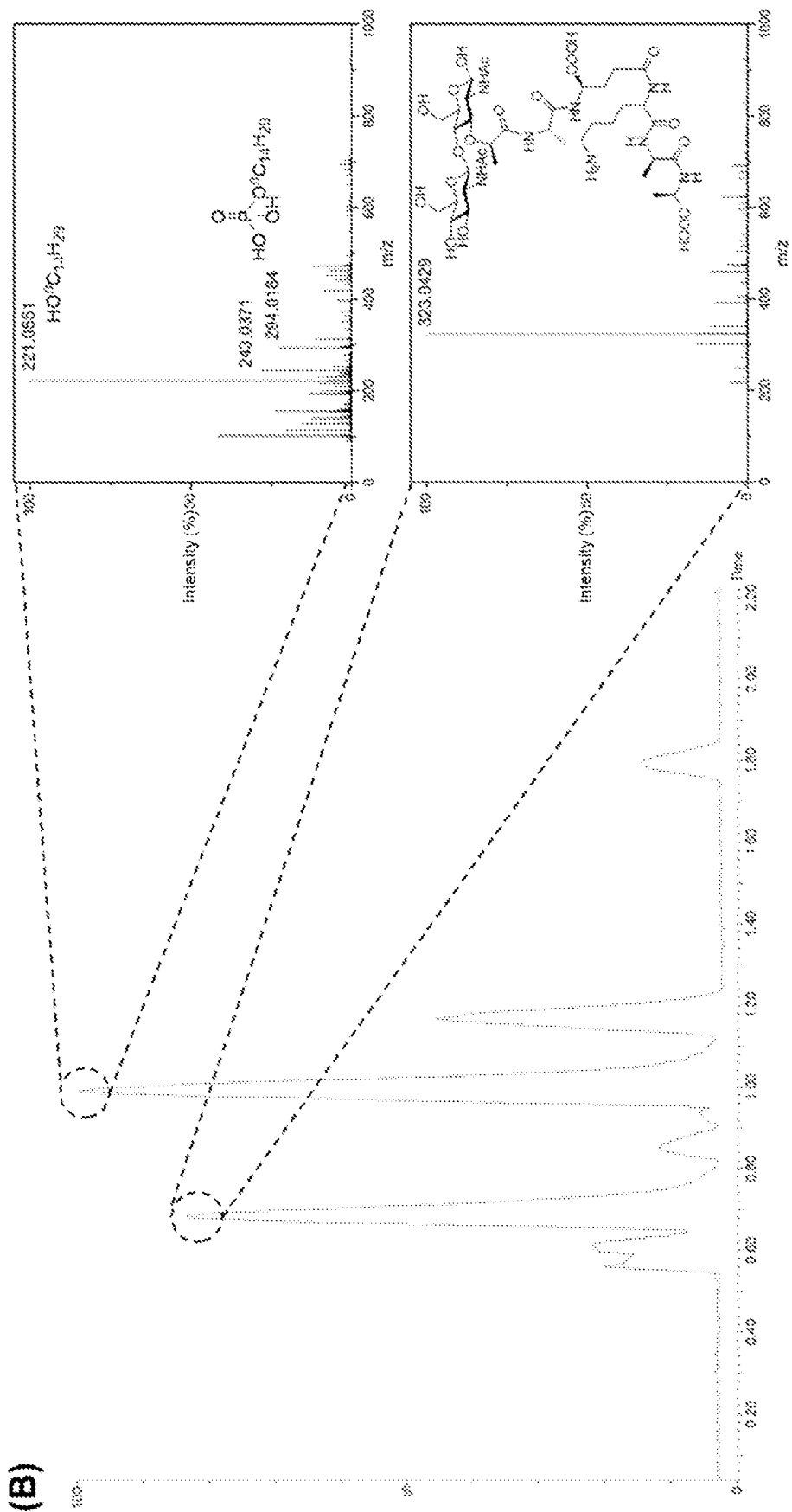

LC-ESI-TOF MS analysis revealed the presence of a m/z fragment consisting of a NAG-NAM with pendant pentapeptide (FIG. 3b). The presence of this fragment, but not NAG-NAG or NAM-NAM fragments in the crude enzyme buffer and phospholipid in buffer, supported the hypothesis that the oligomeric product 1 has an alternating NAG-NAM pattern, as required for a PGO. The resultant structure is similar to that found in natural bacterial cell wall, which is assembled from Lipid II.

Example 2: Labelling PGO 1 to Provide PGOs-Rhodamine or PGO 1 (R=Sulforhodamine B)

PGO 1 was labeled with sulforhodamine B in accordance with previously reported procedures (*Bioconjugate Techniques* (*Third edition*), 2013, 395-463 (Academic Press, Boston)), by covalently binding sulforhodamine B acid chloride (rhodamine) to the free amine on the side chain of lysine moieties of soluble PGO 1. The dye of choice, rhodamine, can be easily coupled to the lysine amine and has a wavelength suitable for the stimulated emission depletion (STED) technique in super-resolution microscopy studies.

The lysine residue has been extensively modified without significant influence on substrates' enzymatic activities, according to previous reports (*Angew. Chem. Int. Ed.*, 2012, 51, 10123-10126). The PG substrate retained similar binding parameters with penicillin binding proteins, which are responsible for peptidoglycan assembly, and could be effectively applied for metabolic labeling of cell wall on live bacteria.

Synthesis and Characterisation of PGOs-Rhodamine

Typically, 10 mg of 1 was dissolved in 2 mL carbonate buffer (0.1 M, pH=9) and a solution of sulforhodamine B acid chloride in DMF (2 mg/mL, 100 μL) was added. The mixture was left to stir in dark at room temperature for 2 hours and dialysed afterwards to give PGOs-rhodamine. The product was characterised with proton NMR. As shown in FIG. 11, proton ratio between f (aromatic, 5H), d (acetyl, 3H) and a (terminal methyl, 3H) suggested an average of 4.4 rhodamine labeled peptide moieties and 9 acetylated glucosamine units connecting to 1 lipid aglycone.

Example 3: Other Labels for PGO 1

PGOs with fluorophore and antibacterial molecules were prepared for various applications. The labels include naphthalimide, rhodamine and cyanine for in vitro or in vivo fluorescence imaging, and antibiotic or antigen molecules for bacteria killing.

Synthesis of PGOs-Cyanine 7.5 (or PGOs-Cy7.5)

PGO 1 was labeled with cyanine 7.5 by analogy to the procedure described in Example 2. No characterisation was carried on the resulting product.

Synthesis of PGOs-napthalimide

PGO 1 was labeled with napthalimide by analogy to the procedure described in Example 2. No characterisation was carried on the resulting product.

Synthesis of PGOs-Imipenem

PGO 1 was labeled with imipenem by analogy to the procedure described in Example 2. No characterisation was carried on the resulting product.

Example 4: Synthesis of Inhibitor

PGOs-inhibitor can be derived from chitosan acetate or polymer 2. The synthetic procedure are described below.

Synthesis of PGOs-Inhibitor (without Pentapeptide) Starting from Chitosan Acetate Chitosan acetate (57 mg, 0.2 mmol, Carbosynth Ltd., Berkshire, UK) was dissolved in 15 mL THF at 0° C. Methylamine (1.0 M THF solution, 0.3 mL) was added dropwise and the mixture was slowly warmed up to room temperature with stirring. After 24 hours, the solvent was removed under reduced pressure. The residue was washed with saturated ammonium chloride solution and water, then evaporated to dryness and dissolved in 30 mL dichloromethane. To this solution was added 1H-tetrazole (21 mg, 0.3 mmol) and methyl (2R)-3-(((benzyloxy)(diisopropylamino) phosphanyl)oxy)-2-(dodecyloxy)propanoate (102 mg, 0.2 mmol) at 0° C. (*J. Am. Chem. Soc.* 2012, 134 (22), 9343-9351). The mixture was warmed up and stirred at room temperature for 5 hours before cooling to −50° C. Then tert-butyl hydroperoxide (70%, 1 mL) was added and the mixture was left stirring overnight. After removing solvent under reduced pressure, the residue was washed with saturated ammonium chloride solution, saturated sodium bicarbonate solution and water to give crude product. Then deprotection was done by dispersing the crude product in 20 mL mixture of methanol and water (v/v, 1:1), followed by addition of LiOH (1 M aqueous solution, 1 mL). The mixture was stirred for 2 hours before dialysis and lyophilization to give the final product (25 mg, 63% for two steps from chitosan acetate) as a yellow solid.

Synthesis of PGOs-Inhibitor (with Pentapeptide) Starting from 2

Crude polymer 2 was dissolved in 15 mL THF at 0° C. Methylamine (1.0 M THF solution, 0.3 mL) was added dropwise and the mixture was slowly warmed up to room temperature with stirring. After 24 hours, the solvent was removed under reduced pressure. The residue was washed with saturated ammonium chloride solution and water, then evaporated to dryness and dissolved in 30 mL dichloromethane. To this solution was added 1H-tetrazole (21 mg, 0.3 mmol) and methyl (2R)-3-(((benzyloxy)(diisopropylamino)phosphanyl)oxy)-2-(dodecyloxy)propanoate (102 mg, 0.2 mmol) at 0° C. (*J. Am. Chem. Soc.* 2012, 134 (22), 9343-9351). The mixture was warmed up and stirred at room temperature for 5 hours before cooling to −50° C. Then tert-butyl hydroperoxide (70%, 1 mL) was added and the mixture was left stirring overnight. After removing solvent under reduced pressure, the residue was washed with saturated ammonium chloride solution, saturated sodium bicarbonate solution and water to give crude product 17. Then the residue was dispersed in 20 mL mixture of methanol and water (v/v, 1:1) and LiOH (1 M aqueous solution, 1 mL) was added. The mixture was stirred for 2 hours before dialysis and lyophilization to give the final product 17 (70 mg, 70% for two steps from 2) as a yellow solid.

Example 5: Metabolic Labeling of Bacteria Cell Walls with PGOs

Figure 4A:
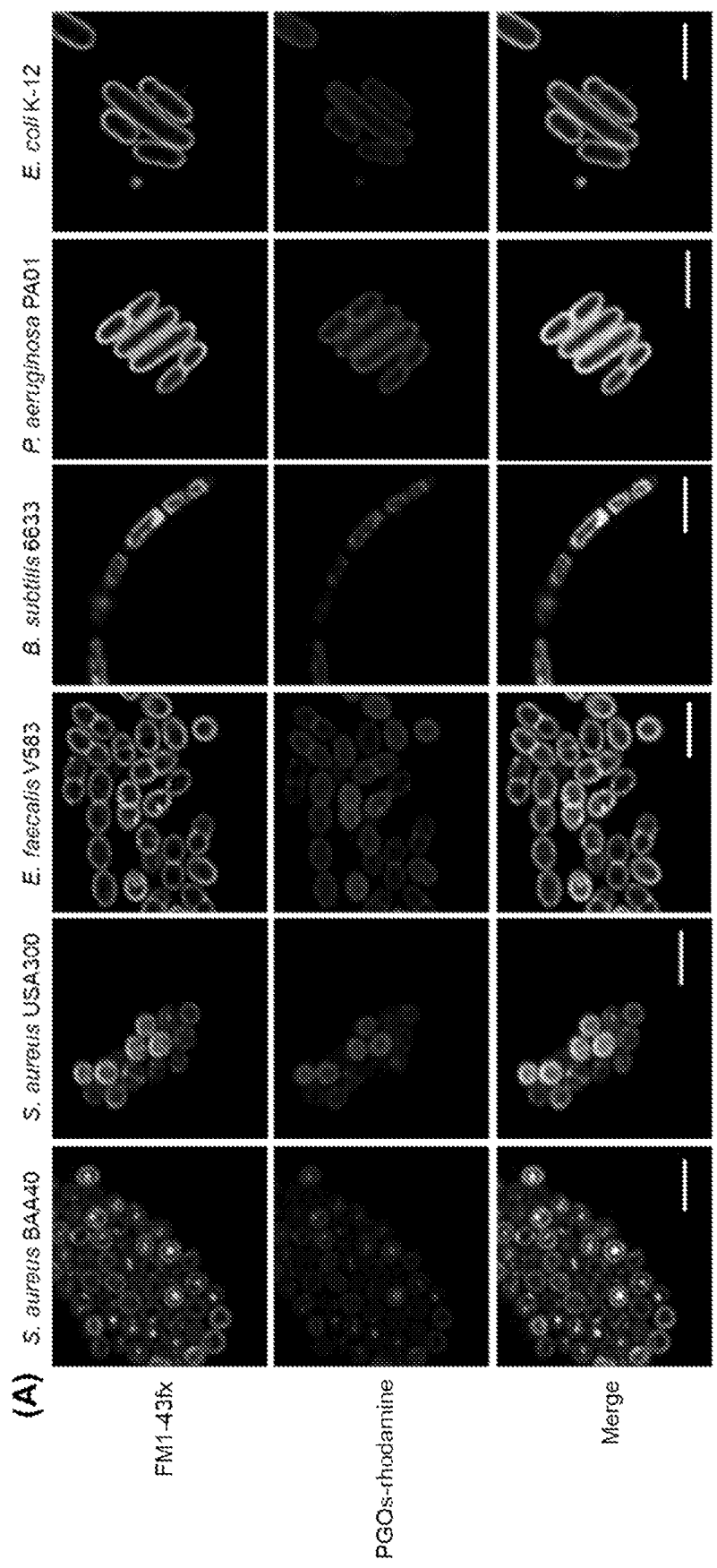

Bacteria strains were cultured in the presence of PGOs-rhodamine, as prepared from Example 2, and analysed under Stimulated Emission Depletion Microscopy (STED). A total of 6 bacteria strains were evaluated for this study, of which 4 were Gram-positive and 2 were Gram-negative (FIG. 4a). Among these, methicillin-resistant *Staphylococcus aureus* (MRSA), vancomycin-resistant *Enterococcus faecalis* and *Pseudomonas aeruginosa* are clinically relevant strains that represent multi-drug resistant (MDR) bacteria. The membrane dye FM 1-43fx was used as an indicator dye for bacterial cell surface localisation (FIG. 4a).
Procedure for Culturing Bacteria with PGOs-Rhodamine and Stimulated Emission Depletion Microscopy (STED)

To prepare samples for super resolution STED microscopy, overnight broth cultures were grown in 5 ml of fresh culture broth (1:100 dilution) to prepare logarithmic phase cultures after incubation at 37° C. for 4 hours in a shaking incubator (225 rpm). Then, bacteria cells were pelleted by centrifugation at 1,500×g for 5 min, suspended in culture media (MHB and BHI) at a concentration of $10^8$ CFU ml$^{-1}$ and incubated for 1 h in the dark in the presence of 100 µg/ml of rhodamine-labeled derivative of 1 at 37° C. with agitation (225 rpm). Bacterial cells were next incubated with the membrane stain FM1-43FX (Life Technologies) at a final concentration of 5 µg/ml for 5 min, as suggested by the manufacturer, and subsequently washed three times with phosphate-buffered saline (PBS) and resuspended in a fixative solution of 2% paraformaldehyde in PBS (pH 7.0). Cells were fixed for 1 h at 37° C. in a shaking incubator (225 rpm), washed three times in PBS and applied to a sterile glass bottom collagen coated dish (MatTek Corporation).

100 µg/mL of PGOs-rhodamine was incubated in mammalian 3T3 cells for 1 h following the procedure used for bacteria (as above), and was analysed under similar conditions.

STED super resolution microscopy was performed on a Leica TCS SP8 STED-3× microscope (Leica Microsystems, Wetzlar, Germany) at SingHealth Advanced Biomaging Core. 479 nm and 556 nm lasers were used for fluorescence excitation, while 660 nm STED laser was used for depletion. In order to achieve maximum lateral resolution, all images were acquired in 2D STED mode. Further image processing required deconvolution, which was done using Huygens Professional software (Scientific Volume Imaging, Hilversum, Netherlands).
Results Based on super-resolution STED microscopy studies, PGOs-rhodamine was colocalised with FM 1-43fx in all of the bacteria strains tested, suggesting PGOs were successfully incorporated into the bacterial cell walls of all 6 tested strains (FIG. 4a).

No significant fluorescent signals were detected in treated mammalian 3T3 cells, with trace amount (white arrow) hypothetically from non-specific adsorption and endocytosis, confirming that the PGOs-rhodamine does not get into mammalian 3T3 cells (FIG. 4c). These results demonstrate the utility of PGOs-rhodamine as a bacteria-specific indicator.

Example 6: Relative Fluorescence Intensity Among Different Bacteria Strains that Incorporated PGOs-Rhodamine The relative fluorescence intensity on bacteria surfaces among bacteria strains after incorporation of PGOs-rhodamine was quantified according to the method reported by Burgess et al. (*Proc. Natl. Acad. Sci. USA*, 2010, 107, 12564-12569; *Cell Cycle*, 2014, 13, 1400-1412).
Measurement of Fluorescence Intensity Calculation was done using Fiji ImageJ according to the procedure reported by Burgess (*Proc. Natl. Acad. Sci. USA*, 2010, 107, 12564-12569; *Cell Cycle*, 2014, 13, 1400-1412). Both the laser power and STED power were kept constant throughout the experiments for the acquisition of the images for calculation purposes. To minimize crosstalk, the excitation wavelength of the red channel was set at 570 nm, with the emission photons collected from 580 nm to 620 nm. Only the cells that were in focus were taken into account for calculation, and the channels of the images (not processed by deconvolution) were split prior to calculation; calculating only those from the red channel. The area with fluorescence on each bacterial cell surface was drawn and the total intensity was normalised by the number of pixels found in the area (mean). A total of hundred or more cells per bacterial strain were computed, and the average was taken for comparison.
Results The quantification results demonstrated that both Gram-negative and Gram-positive species showed significant uptake and labeling by PGOs-rhodamine (FIG. 4b). The broad spectrum of species that can be labelled by PGOs makes it a useful substrate for design of a new class of bacterial bioimaging reagent. In addition, PGOs scaffold could be further exploited as an antimicrobial for therapeutics. As PGOs anchor onto cell wall after incorporation by bacteria, they could facilitate active targeting to kill bacteria, through conjugation of antibiotics or direct structural modification. PGO analogs as described in Example 4 mimicked structure of moenomycin antibiotics to bind PGTs sufficiently strong to prevent the enzymes from carrying out their responsibilities any further, thus resulting in defects in cell wall and inhibition of bacterial growth.

Example 7: Structural Component Leading to Uptake and Incorporation of PGOs in Bacteria To confirm and verify which component of the PGOs led to robust uptake and incorporation, substrates forming part of the PGOs, such as the peptide conjugated-chitosan and the pentapeptide, were labelled with rhodamine. The resulting chitosan-pentapeptide conjugate with rhodamine tag 16, rhodamine labeled pentapeptide 14, as well as PGOs-rhodamine and rhodamine alone, were incubated together with *E. faecalis*, and incorporation was measured by quantifying bacterial cell surface fluorescence intensity according to the procedure in Example 6. The total intensity was normalised by the area of fluorescence.

Synthesis of Rhodamine Labeled Pentapeptide 14

Rhodamine labeled pentapeptide 14 was synthesised by replacing Fmoc on lysine side chain of 12 with rhodamine B to provide 15, followed by removal of Boc with hydrogen chloride using the same procedure as 12 and removal of OBn and OMe with LiOH using the same procedure as 1. The product was dialysed using 100-500 MWCO dialysis tubing and lyophilised without further purification.

Synthesis and Characterisation of Compound 15, Boc-Ala-D-Iso-Glu(OBn)-Lys(Rhodamine)-D-Ala-D-Ala-OMe To a solution of 12 (91.4 mg, 0.10 mmol; prepared according to General Procedure 2) in 10 mL DMF was added 2 mL diethylamine and the mixture was stirred at room temperature for 1 hour. After checking full consumption of 12 by TLC, diethylamine was removed in vacuo and rhodamine B (71.9 mg, 0.15 mmol), HOAt (20.4 mg, 0.15 mmol) and EDCl (28.8 mg, 0.15 mmol) were added. Then DIPEA (38.8 mg, 0.30 mmol) was added into the solution and it was left to stir at room temperature overnight before 30 mL water was added. Then it was extracted with EtOAc (30 mL×2) and the combined organic layer was washed with water (50 mL×5) and brine (50 mL). After removing solvent in vacuo, the crude was purified by flash column chromatography (40% $CH_2Cl_2$/Acetone) to give compound 15 (73.6 mg, 64%) as a red solid.

$^1$H NMR (500 MHz, Chloroform-d) δ 8.34 (d, J=7.9 Hz, 1H), 7.82 (s, 1H), 7.74 (s, 3H), 7.55 (q, J=3.8 Hz, 2H), 7.33 (dd, J=14.2, 5.8 Hz, 4H), 7.24 (d, J=15.1 Hz, 2H), 7.09-6.99 (m, 4H), 6.85 (d, J=9.8 Hz, 2H), 6.77 (s, 2H), 5.01 (s, 2H), 4.24 (t, J=7.2 Hz, 3H), 3.66 (q, J=7.5 Hz, 10H), 3.38-3.31 (m, 1H), 2.94 (d, J=37.7, 35.0 Hz, 1H), 2.33 (s, 1H), 2.14 (s, 1H), 2.02 (s, 2H), 1.74-1.60 (m, 4H), 1.48-1.40 (m, 10H), 1.39-1.33 (m, 23H), 1.32-1.23 (m, 18H), 1.22-1.15 (m, 4H), 0.97-0.82 (m, 16H). $^{13}$C NMR (101 MHz, Chloroform-d) δ 167.88, 165.14, 157.75, 155.61, 134.57, 133.46, 133.23, 132.60, 131.58, 131.33, 131.00, 130.51, 130.38, 128.93, 128.68, 128.65, 128.58, 128.40, 114.23, 113.65, 96.59, 68.30, 67.65, 46.27, 38.89, 30.51, 29.83, 29.07, 28.52, 23.90, 23.11, 14.17, 12.81, 11.09, 1.15.

Synthesis of Polymer 16, Chitosan-Pentapeptide Conjugate with Rhodamine Tag

To a solution of pentapeptide 15 (23.0 mg, 0.02 mmol; prepared as above) in 20 mL $CH_2Cl_2$ was added 4 mL 2.0 M HCl in $Et_2O$ and the mixture was stirred at room temperature for 4 hours. After checking full consumption of 15 by TLC, the solvent was removed in vacuo and DIPEA (12.9 mg, 0.1 mmol) in 20 mL DMF was added at room temperature. Then polymer 5 (10.0 mg, 0.02 mmol; prepared according to General Procedure 1), HATU (19.0 mg, 0.05 mmol) and HOAt (6.8 mg, 0.05 mmol) were added into the solution and the reaction was left to stir overnight. After removing solvent under reduced pressure, the residue was washed with saturated ammonium chloride solution and water to give a crude of protected chitosan-pentapeptide conjugate. The crude was redispersed in 10 mL MeOH, followed by addition of tetrabutylammonium fluoride (261 mg, 1 mmol), hydrazine (32 mg, 1 mmol) and LiOH (1 M aqueous solution, 0.1 mL). The mixture was stirred for another 12 hours before dialysis and lyophilisation to give the final product 16 as a red solid.

Results

Of all the substrates tested, only bacteria incubated with the rhodamine-labeled PGOs showed high fluorescence intensities (FIG. 5). These results are consistent with a previous crystal structure report which suggested that every moiety, including the oligosaccharide chain and the pentapeptide of PGOs, are required for effective binding to the active site of PGT enzymes (*Proc. Natl. Acad. Sci. USA*, 2012, 109, 6496-6501). These results confirmed that the accumulation of PGOs-rhodamine was due to the biological incorporation of PGOs into the bacterial cell surface, and not due to trivial accumulation of any of the components or breakdown products of PGOs-rhodamine.

Example 8: Effect of Increasing Molecular Weight of PGO on Fluorescence Intensity It has been demonstrated that peptidoglycan substrates with four sugar units (Lipid IV) were associated with higher efficiencies of enzymatic metabolism and incorporation in comparison with those having two sugar units (Lipid II) (*J. Am. Chem. Soc.* 2011, 133 (22), 8528-8530). The limit of the correlation between molecular weight and uptake was investigated by synthesizing larger PGOs.

PGO 1 was synthesised based on the procedure in Example 1, except that chitosan 9 having equal or less than 3 kDa MW (corresponding to around 10 sugar units) was replaced with either chitosan of 5 kDA MW (around 25 sugar units) or 10 kDa MW (around 50 sugar units). The respective PGOs obtained were labelled with rhodamine in accordance with Example 2 and subsequently incubated with *S. aureus* ATCC 29213 ($10^7$ CFU/mL) at 100 μg/mL for 1 hour at 37° C. in Mueller Hinton Broth (MHB) in accordance with the procedure in Example 5. After incubation, the bacteria suspension was pelleted and washed with PBS 3 times, and subsequently the fluorescence intensity of bacterial samples was measured in accordance with Example 6.

As shown in FIG. 12, maximum fluorescence intensity was achieved with PGOs that derived from chitosan having 25 sugar units. The results of size preference provided insight into the binding mode of glycosyltransferases with PG substrates. With further structural analysis of the binding complex, this may pave the way for development of better bacteria substrates or inhibitors with enhanced activities.

Example 9: Characterisation of Bacterial Cell Walls that Incorporated PGOs

STED Super-Resolution Microscopy and Cryo-Transition Electron Microscopy (Cryo-TEM)

Figure 6A:
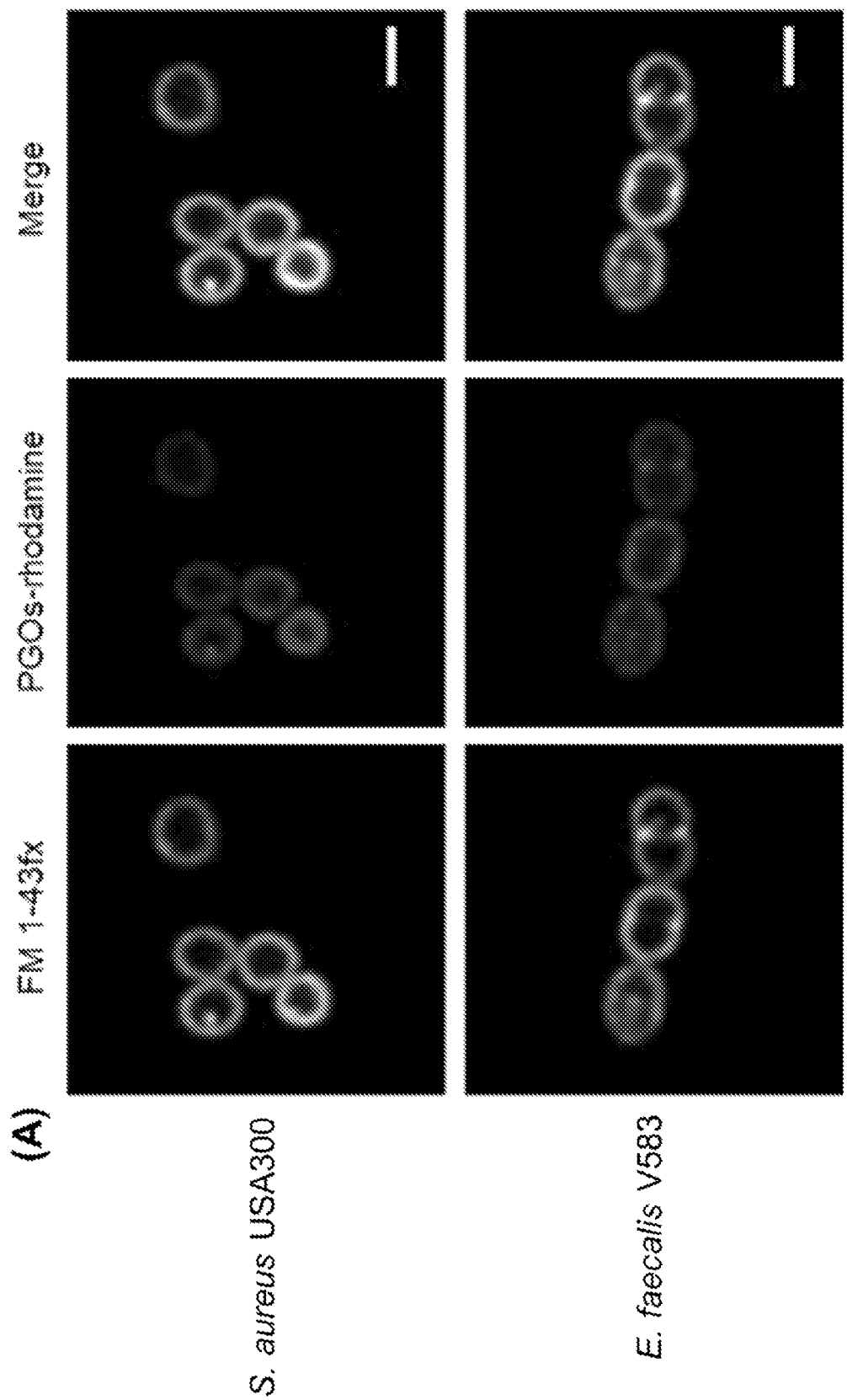

To characterize the bacterial PG cell walls that incorporated PGOs, the microscope images obtained from Example 5 were further analysed. STED super-resolution microscopy for *S. aureus* and *E. faecalis* showed thick cell walls that incorporated PGOs-rhodamine signals (FIG. 6a). Upon closer observation, it was noticed that the PGOs-rhodamine signal resided on the inner part of the bacterial cell, compared to the membrane dye FM 1-43fx which was adsorbed directly onto the bacterial cell surface (FIG. 6a). This incomplete colocalisation ruled out the possibility that the PGOs-rhodamine had been only physically adsorbed onto the exterior of bacterial cells, and indicated that it was specifically transported into bacterial cells. This was confirmed by cryo-electron microscopic studies of the PGOs-rhodamine labeled bacteria cell wall, which showed a slightly thicker layer relative to the control, which replaced PGOs-rhodamine with PBS during incubation, indicating the incorporation of rhodamine into the PG network.

To prepare samples for cryo-TEM, overnight TSB cultures were subsequently grown in 5 ml of fresh culture broth (1:100 dilution) to prepare logarithmic phase cultures after incubation at 37° C. for 4 hours in a shaking incubator (225 rpm). Then, E. faecalis bacteria cells were pelleted by centrifugation at 1,500×g for 5 min, suspended in TSB culture media at a concentration of $10^8$ CFU $ml^{-1}$ and incubated for 2 h in the dark in the presence of 1 mg/mL of substrate 1 (as prepared from Example 1) or its rhodamine-labeled derivative (as prepared from Example 2) at 37° C. with agitation (225 rpm). The cells were subsequently washed three times with PBS and frozen onto copper grid by liquid nitrogen. Cryo-TEM was performed using FEI Titan Krios (300 kV, FEG, Falcon II direct detector, and Gatan Tridiem GIF with 2k×2k post-GIF Gatan CCD) at NUS Centre for BioImaging Sciences. The images were taken at 14,000× magnification and processed subsequently by ImageJ.

TIRF Microscopy of L-Form Bacteria

Figure 6B:
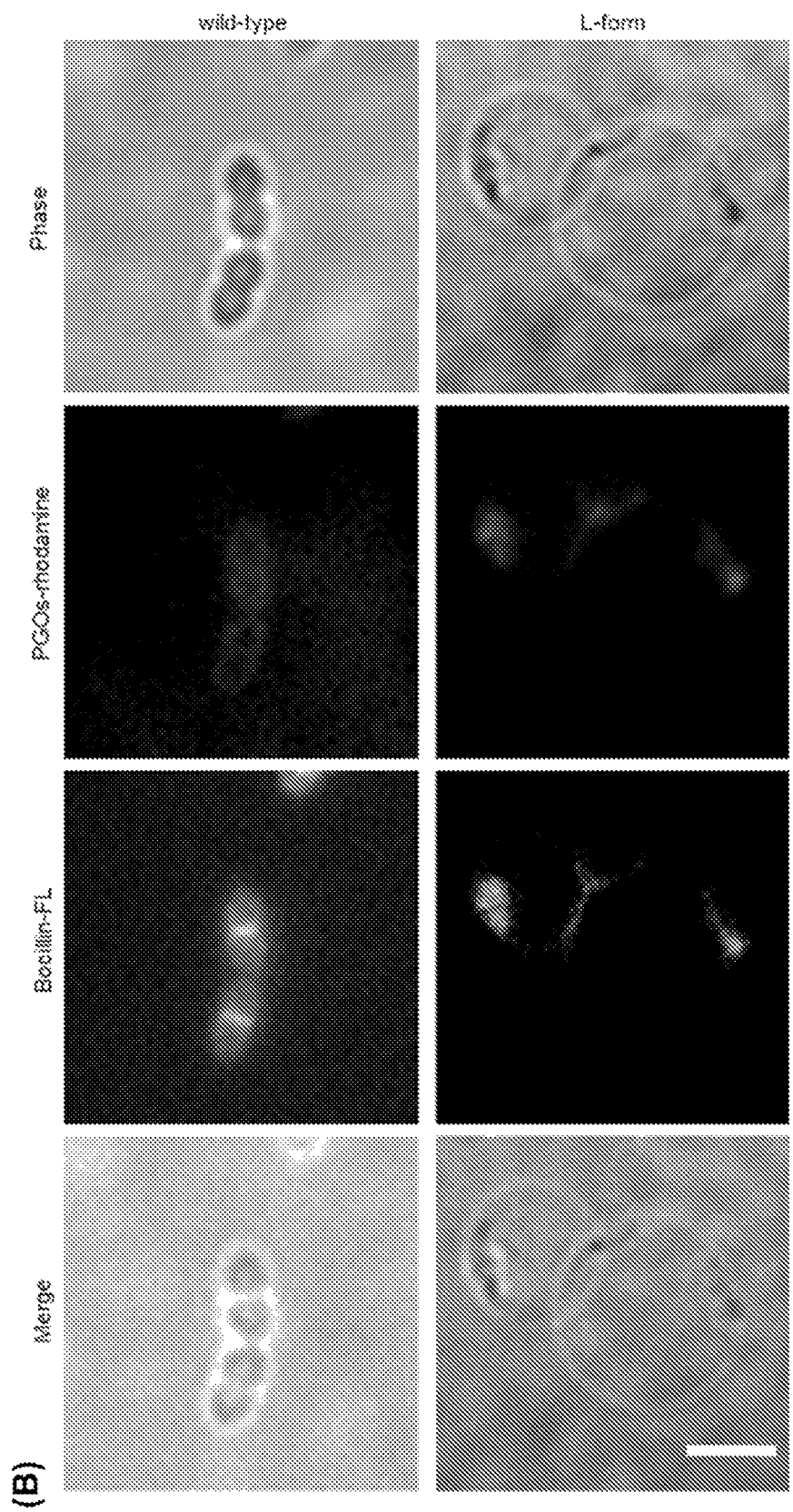

L-form bacteria and fluorescence microscopy were deployed to further study the interaction between PGOs and bacterial cell walls. L-form bacteria are deficient in cell wall components (referring to substrates forming the cell wall) or cell wall fragments (referring to the residues formed after cell autolysis) on their surface. BOCILLIN™ FL (Boc-FL), a fluorescent penicillin-derivative, was used to compare the localisation of penicillin-derivatives to that of PGOs. Incubation of PGOs-rhodamine (red) and Boc-FL (green) with the wild type cells resulted in an intense fluorescence at the septum region and also the adjacent cell surface (FIG. 6b—left column), whereas L-form cell surfaces showed only a few distinct fluorescent punctae for both PGOs-rhodamine and Boc-FL (FIG. 6b—right column). These results showed that PGOs and penicillin-derivatives were colocalised in the same areas, whether it is the division septa of the wild type strain or the distinctive punctae in the L-form strain's cell surfaces.

The localisation of PGOs-rhodamine was also compared to the membrane dye Polymyxin B-BODIPY FL (Polymyxin B). Strong uniform membranous staining by Polymyxin B was observed in the L-form cells, including the region with dense membrane material as indicated (FIG. 9, bottom row). In comparison, the PGOs localised in discrete punctae on the L-form cell surfaces. While wild type cell envelope demonstrated a comprehensible enhancement at septum compared to cell surface, only a few discrete spots of substrate PGOs-rhodamine binding were seen on the L-form surface. Thus, it is concluded that PGOs' localisation patterns within bacterial cell walls strongly resemble penicillin-derivatives (FIG. 9, top row).

L-forms were generated using DM3 agar by modified methods from reported protocol (Molec. Gen. Genet., 1979, 168, 111-115). DM3 medium consists of 1.2 wt % agar, 0.5 wt % Tryptone, 0.5 wt % yeast extract, 1 M Succinate (pH 7.3), 3.5 wt % $K_2HPO_4$ and 1.5 wt % $KH_2PO_4$, 20 wt % Glucose, 1 M $MgCl_2$ and 2 wt % BSA, with the balance being water. Parental strain E. faecalis OG1RF was grown overnight at 37° C. in DM3 broth. 100 µL of an overnight culture was directly plated on DM3 agar plates supplemented with 200 µg/ml penicillin G. The plates were incubated at 37° C. Small fried egg-like shaped colonies appeared after 5 days. The colonies were restreaked on DM3 agar with 200 µg/ml penicillin G for a few times to get pure colonies, and serial passaging (ten times) of pure colonies in DM3 agar with decreasing penicillin G concentrations to generate stable L-forms. The stable L-forms were stored at −80° C. in 20% glycerol.

Fluorescence microscopy was performed on Nikon TIRF microscope (Nikon instruments, NY, USA). BODIPY FL and sulforhodamine B were excited at 488 and 560 nm and emitted at 512 and 580 nm respectively. Three days old L-forms grown in DM3 broth was washed and incubated with 1 µL of Polymyxin B or Boc-FL (1 mg/mL) and 2 µL substrate (2 mg/mL; as prepared from Example 2) for 30 min at 37° C. After 30 min, cells were washed thrice with 1 mL of liquid DM3. The final pellet was suspended in 30 µL liquid DM3. 5 µL of cells were placed on poly-lysine coated slides and observed under TIRF microscope (FIG. 9, bottom row). Image processing was done using MetaMorph Microscopy Automation & Image Analysis Software (Photometrics, AZ, USA). ImageJ was utilised for further image processing.

Isothermal Titration Calorimetry

Figure 6C:
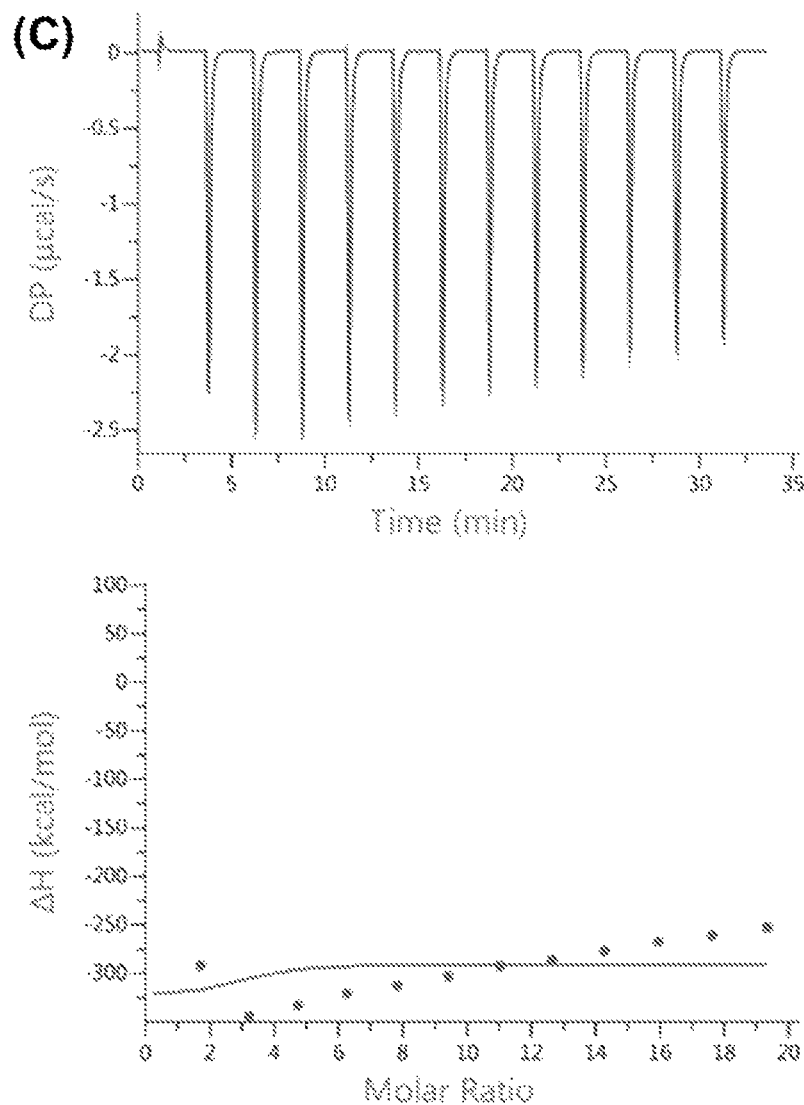

Isothermal titration calorimetry (ITC) was used to check the binding interactions between PGOs and PGT proteins (FIG. 6c). E. coli K12 PBP1a was used, since E. coli K12 was shown to incorporate PGOs, and E. coli K12 PBP1a is known to recognize large substrates. Interestingly, the interaction between PGOs and E. coli K12 PBP1a had an exceptionally high exothermic enthalpy (FIG. 6c) which defied a perfect fit into binding models. ΔH was calculated to be −33 kcal/mol for this interaction. As an earlier work by Wong and Cheng showed a similar trend in the raw heat graph (without curve fitting and calculation) of Lipid II's interaction with PGT (Angew. Chem. Int. Ed., 2012, 51, 10123-10126), this result is plausible, probably due to the extensive hydrogen bonding interaction present in multivalent binding of the oligomers, and thermodynamic parameters following reported protocols was computed. It was found that the binding energy for PGOs and E. coli K12 PBP1a had ΔG=−9.8±0.2 kcal/mol, which is comparable to the binding energy between moenomycin and S. aureus/E. coli PBP1b (Proc. Natl. Acad. Sci. USA, 2012, 109, 6496-6501).

ITC experiments were performed using Microcal PEAQ-ITC instrument (Malvern Instruments Ltd, Malvern, UK). The solutions of PGOs 1 (30 µM; as prepared from Example 1) and E. coli K12 PBP1a (300 nM) in deionised water were prepared fresh before each experiment and three replicates were performed for each setting. 0.4 µL of PGOs solution was titrated into 300 µL E. coli K12 PBP1a solution at 25° C. followed by twelve 3-µL injections at 150 seconds intervals. The reaction cell was stirred at 750 rpm and reference was set at 10 µcal/s. Experiments were performed in triplicates and the integrated fitted curve showed data points using one-site fitting function for 1 to E. coli K12 PBP1a molar ratio. The data were all obtained and analysed using Microcal softwares.

Example 10: Sensitivity and Selectivity in Bacteria Labelling

The potential of the synthetic PGOs as a diagnostic tool was explored. Such a tool has to be sensitive to low bacteria concentration and has to generate results fast enough to be sufficiently practical. Hence, varying bacteria concentrations have been incubated with PGOs-rhodamine at 200 μg/mL for 1 hour (including PBS control) and washed with PBS, and then subject to quantification by fluorospectrometer (FIG. 7). Significant fluorescence was observed in bacteria with concentration as low as $10^1$ CFU/mL when compared to PBS control, and the intensity increases with bacteria concentration.

Procedure: For limit of detection, 1 mL E. coli EC958 was prepared at different concentrations each, and PGOs-rhodamine (200 μg) was added for metabolic labeling for 1 hour at 37° C. All the bacteria were harvested by centrifugation at 5000 rpm for 15 min and washed with PBS for 3 times. The bacteria pellet was finally dispersed in 1 mL PBS for fluorescence analysis with fluorospectrometer.

The low detection limit of PGOs-rhodamine was shown to be useful to identify antibiotic-resistant strains. Infections caused by such bacteria require careful treatment due to their complexity and lethality. Therefore, enormous investment has been dedicated to development of methods to timely diagnose bacterial infections involving antibiotic resistance. The broad spectrum of bacteria recognizing PGOs as substrate was demonstrated in earlier examples, thus it was possible to identify the presence of resistant strains in a rapid manner using PGOs.

As the effective uptake of the PGOs relied heavily on cell growth and metabolism, bacteria samples were first treated with antibiotics to inhibit growth of susceptible cells and subsequently, PGOs-rhodamine was added for fluorescence analysis. In detail, E. coli 958 (drug-resistant), E. coli 8739 (drug-sensitive), methicillin-resistant S. aureus, or drug-sensitive S. aureus (at $10^6$ CFU/mL) were incubated with 0-1000 μg/mL penicillin G sodium salt for 2 hours, washed, and then 50 μg/mL PGOs-rhodamine (as prepared from Example 2) for 1 hour consecutively. Eventually, the bacteria samples were washed and resuspended in 1 mL PBS for analysis by fluorospectrometer.

Procedure:

For resistant strain detection, 1 mL of drug-sensitive and drug-resistant bacteria ($10^6$ CFU/mL) were treated with different concentration of antibiotics (Penicillin G sodium salt) ranging from 0 to 1000 μg/ml for 2 h. PGOs-rhodamine (50 μg) were then added for metabolic labeling for 1 hour at 37° C. All the bacteria were harvested by centrifugation at 5000 rpm for 15 min and washed with PBS for 3 times. The bacteria pellet was finally dispersed in 1 ml PBS for fluorescence analysis with fluorospectrometer.

As shown in FIG. 8, a significant and consistent difference in fluorescence intensity was observed between resistant and susceptible strains for the two bacteria species tested, namely E. coli and S. aureus. The selective labelling of resistant bacterial strains, in combination with the PGOs' excellent selectivity towards bacterial cells in contrast to mammalian cells, would enable the identification of antibiotic-resistant bacteria from samples of infection in a facile and practical manner.

Example 11: In Vivo Uptake of PGOs in Mice

To demonstrate that the PGOs can be used in direct in vivo labelling without bacteria pre-treatment, mice were intravenously injected with PGOs-Cy7.5 (prepared in accordance with Example 3).

An imaging result is shown in FIG. 10.

Procedure: S. aureus (ATCC29213) was intraperitoneally injected into mice to develop bacterial infection in most organs of mice, including liver and kidney. At 2 hours post-infection, 5 mg/kg of PGOs-Cy7.5 was intravenously administrated to non-infected and infected mice. Non-invasive image was taken 8 hours post injection of PGO-Cy7.5 using IVIS SpectrumCT (PerkinElmer, USA) to track fluorescence difference.

Discussion: As shown in FIG. 10, PGOs-Cy7.5 was cleared faster in non-infected mice (left) compared to infected ones (right mice). Liver and kidney are two major organs infected in sepsis model, and it can be clearly seen that clearance of PGOs was retarded due to bacterial infection, demonstrated by strong fluorescence in liver area for infected mice in comparison with insignificant fluorescence for non-infected ones. The results of comparison well demonstrated the in vivo bacterial targeting effect, and in turn the applicability as a diagnostic tool, of the PGOs with minor modification by Cy7.5 dye.

In summary, it was shown that inexpensive chitosan can be transformed into biohybrid PGOs that can be successfully incorporated into the cell walls of different bacteria strains. The PGOs could be suitably modified for bioimaging applications as demonstrated above. The biosynthetic hybrid PGOs could constitute a versatile platform to facilitate further mechanistic studies of the biosynthetic process of bacterial cell walls, and further development of broad-spectrum antibiotics.

The invention claimed is:

1. A compound of formula Ia and/or formula Ib:

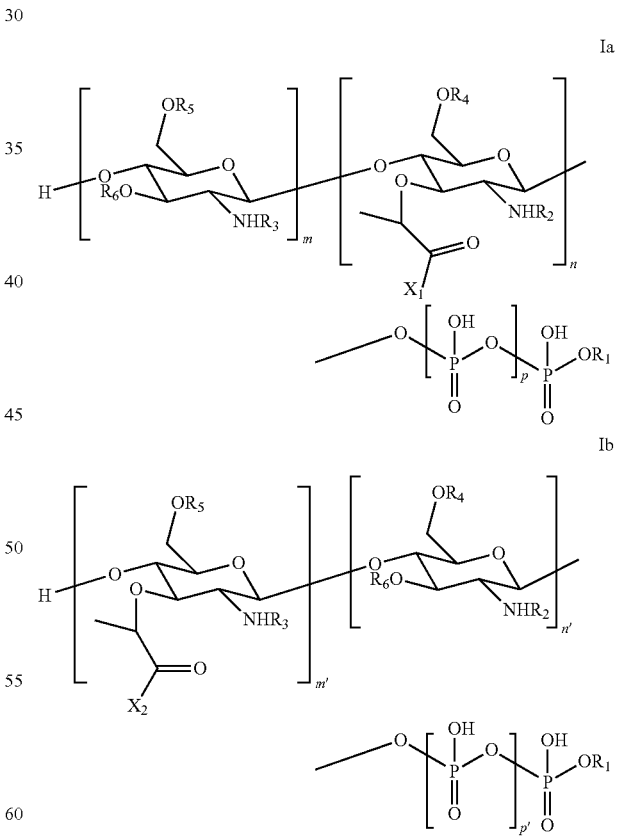

wherein:

$R_1$ represents $C_1$ to $C_{20}$ alkyl or —$CH_2CH(CO_2H)OC_{1-20}$ alkyl;

$R_2$ and $R_3$ each independently represent —C(=O)$R_7$;

$R_4$ to $R_6$ each represent H;

each $R_7$ independently represents $C_1$ to $C_{20}$ alkyl;

$X_1$ and $X_2$ independently represent -$AA_1$-$AA_2$-$AA_3$-D-Ala-$AA_4$, where:

$AA_1$ is selected from $_L$-Ala, $_L$-Gly, $_D$-Gly or $_L$-Ser;

$AA_2$ is selected from $_D$-isoglutamate (γ-$_D$-glutamate, γ-$_D$-Glu), $_D$-isoglutamine, or threo-3-hydroxyglutamate;

$AA_3$ is selected from $_L$-homoserine, $_D$-homoserine, $_D$-5-hydroxylysine, $_D$-Orn, $_L$-Lys, D-Lys, $_L$-Orn, $_L$-2,4-diaminobutyrate, or $_L$-5-hydroxylysine, where the amino group is functionalised to become a $NHR_8$ group and/or, where present, the hydroxyl group is functionalised to become a $OR_8$ group; and $AA_4$ is selected from $_D$-Ala, $_D$-Ser or $_D$-Lacate ($_D$-Lac), at each occurrence $R_8$ is independently selected from one or more of H, a fluorescent group or a pharmaceutically active moiety, n and m, and n' and m' are alternating repeating units, where n is from 5 to 100 and m is from 4 to 100, provided that m has the same value as n or is n−1 and n' is from 5 to 100 and m' is from 4 to 100, provided that m' has the same value as n' or is n'−1, p or p' are 1 or 0, or a pharmaceutically acceptable salt, solvate or prodrug thereof.

2. The compound(s) according to claim 1, wherein the compounds of formula Ia and Ib are Ia' and Ib', respectively

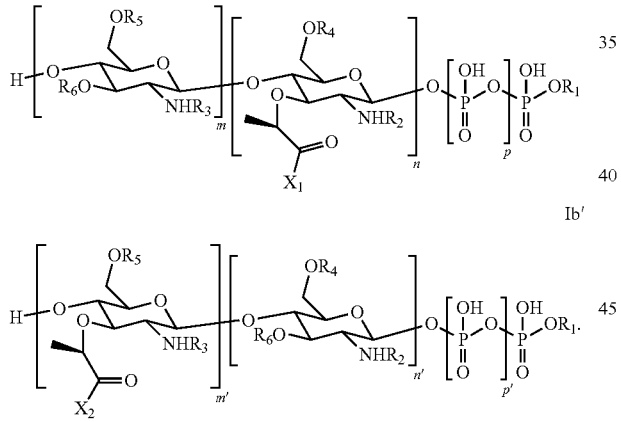

Ia'

Ib'

3. The compound(s) according to claim 1, wherein:

when p and/or p' is 1 and $R_1$ represents $C_1$ to $C_{20}$ alkyl, then $R_8$ represents a fluorescent group or a pharmaceutically active moiety; or when p and/or p' is 0 and $R_1$ represents —$CH_2CH(CO_2H)$ $OC_{1-20}$ alkyl, then $R_8$ represents H.

4. The compound(s) according to claim 1, wherein:

when p and/or p' is 1, $R_1$ represents $C_{10}$ to $C_{15}$ alkyl; or when p and/or p' is 0, $R_1$ represents —$CH_2CH(CO_2H)$ $OC_{10-15}$ alkyl.

5. The compound(s) according to claim 1, wherein each $R_7$ independently represents $C_1$ to $C_6$ alkyl.

6. The compound(s) according to claim 1, wherein:

$AA_1$ is selected from $_L$-Ala, $_L$-Gly, or $_L$-Ser;

$AA_2$ is selected from $_D$-isoglutamate (γ-$_D$-glutamate, γ-$_D$-Glu) or $_D$-isoglutamine;

$AA_3$ is selected from $_L$-Lys, $_D$-Lys, $_L$-Orn or $_L$-2,4-diaminobutyrate, where the amino group is functionalised to become a $NHR_8$ group; and $AA_4$ is selected from $_D$-Ala or $_D$-Ser.

7. The compound(s) according to claim 6, wherein:

$AA_1$ is $_L$-Ala;

$AA_2$ is $_D$-isoglutamate (γ-$_D$-glutamate, γ-$_D$-Glu);

$AA_3$ is selected from $_L$-Lys or $_L$-Orn, where the amino group is functionalised to become a $NHR_8$ group; and $AA_4$ is $_D$-Ala.

8. The compound(s) according to claim 1, wherein:

n is from 5 to 50 and m is from 4 to 50, provided that m has the same value as n or is n−1; and n' is from 5 to 50 and m' is from 4 to 50, provided that m' has the same value as n' or is n'−1.

9. The compound(s) according to claim 1, wherein when a $R_8$ group is a fluorescent group, it is selected from one or more of a rhodamine, a cyanine and a naphthalimide, where the point of attachment of the rhodamine, cyanine and naphthalimide to the rest of the molecule is through a $SO_2$ or C=O moiety.

10. The compound(s) according to claim 9, wherein $R_8$ is selected from one or more of:

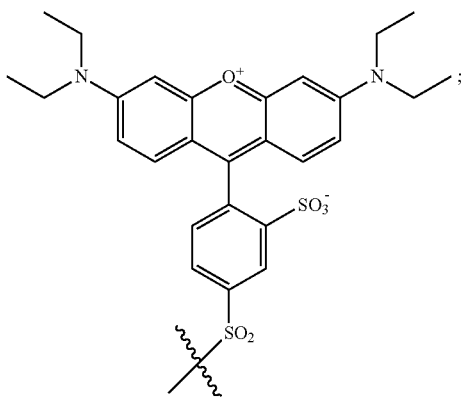

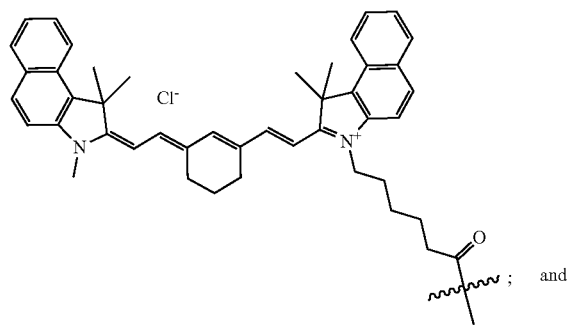

and 67 68

-continued

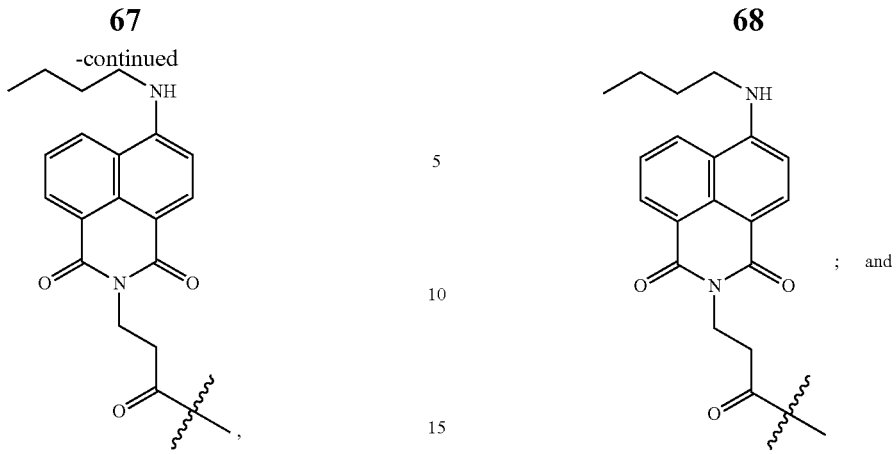

where the wavy line in each of the above moieties represents the point of attachment to the rest of the molecule.

11. The compound(s) according to claim 1, wherein when a $R_8$ group is a pharmaceutically active moiety, it is selected from one or more of an antibiotic and an antigen moiety, where the point of attachment of the antibiotic and the antigen moiety to the rest of the molecule is through a $SO_2$ or C=O moiety.

12. The compound(s) according to claim 11, wherein $R_8$ is selected from one or more of:

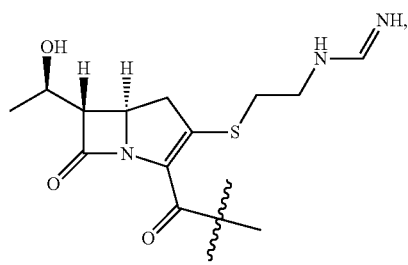

where the wavy line in each of the above moieties represents the point of attachment to the rest of the molecule.

13. The compound(s) according to claim 1, selected from:

(a)

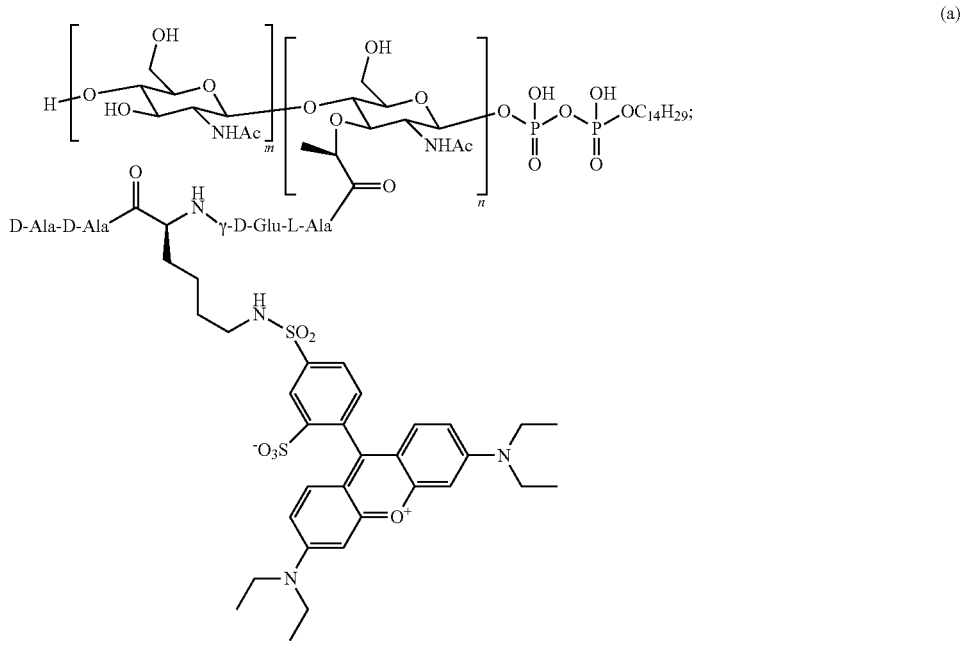

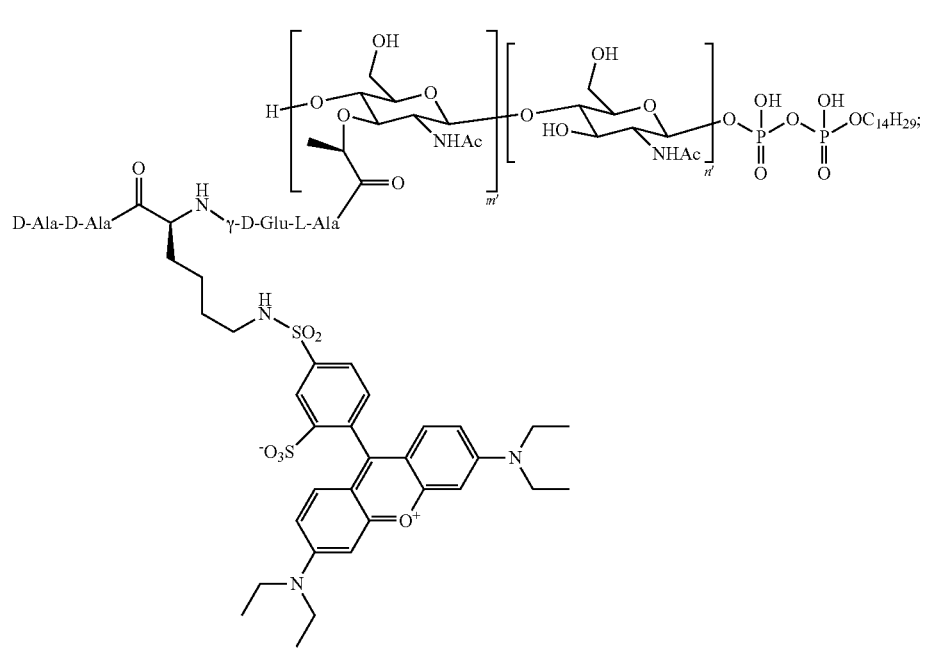
(b)
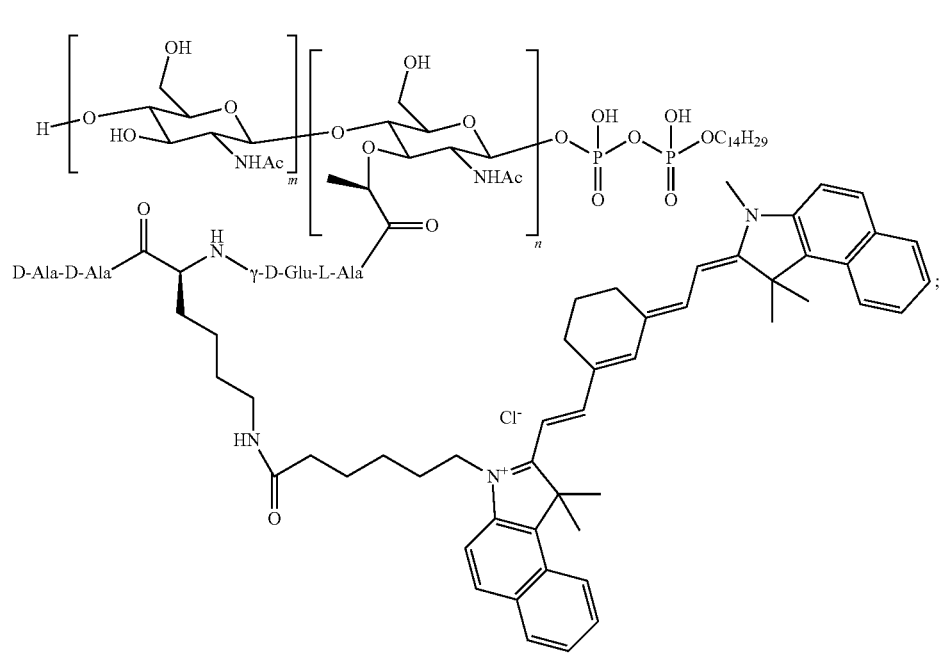
(c)

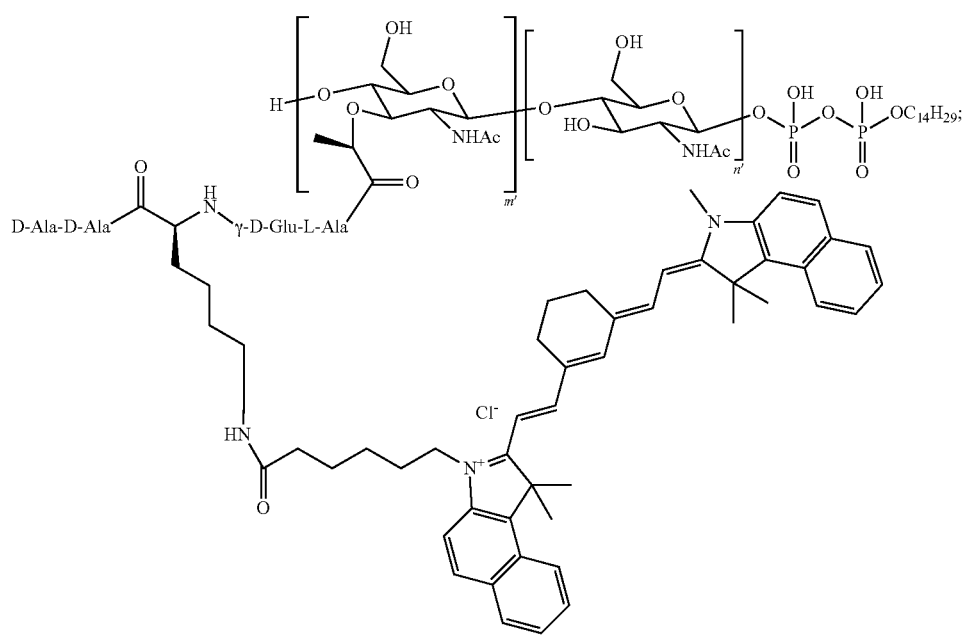
(d)
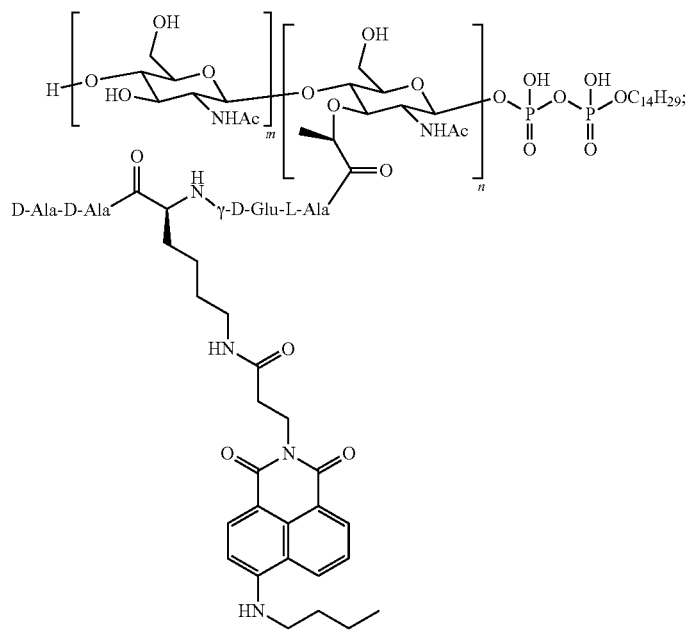
(e)

-continued
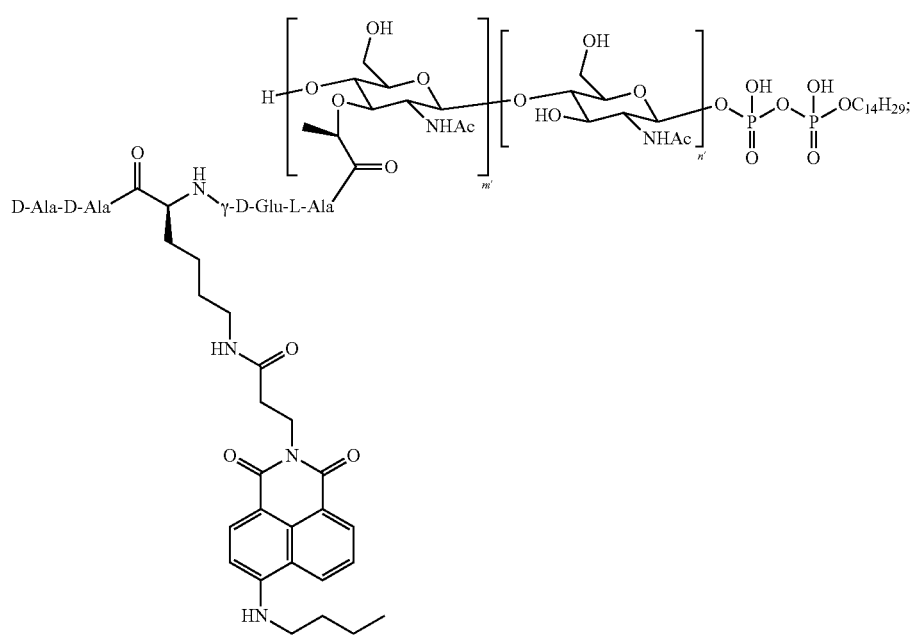
(f)
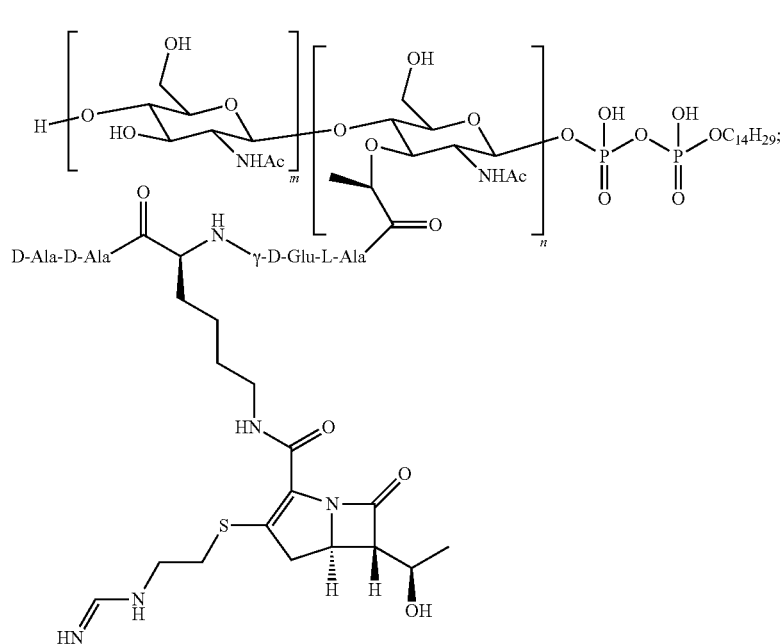
(g)

-continued
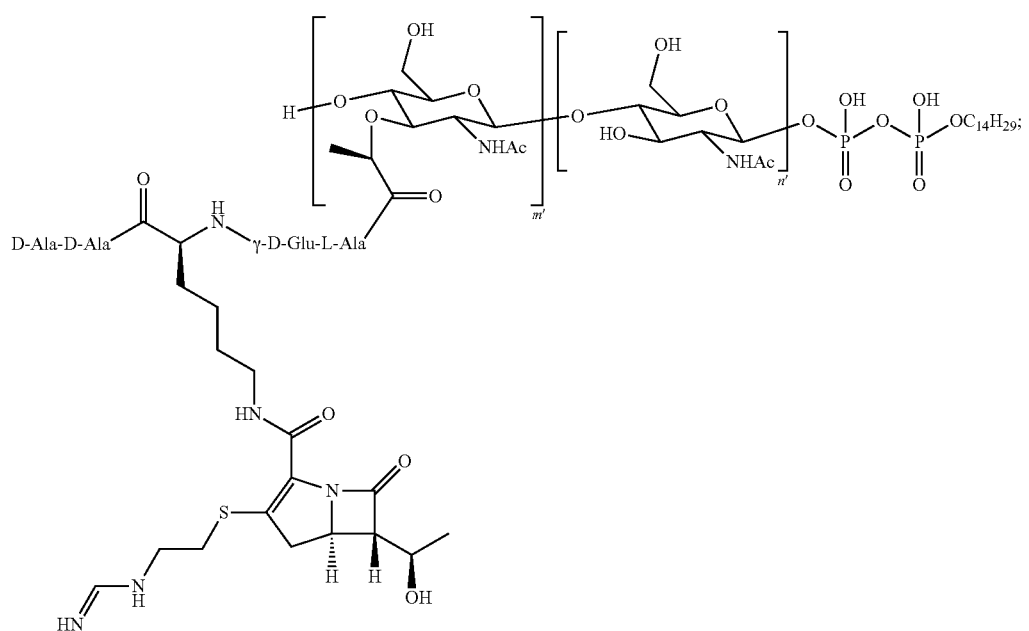
(h)
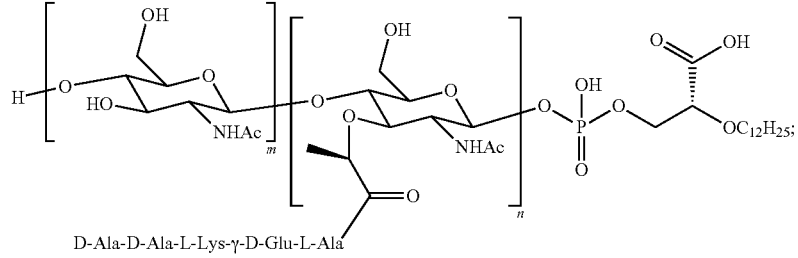
(i)
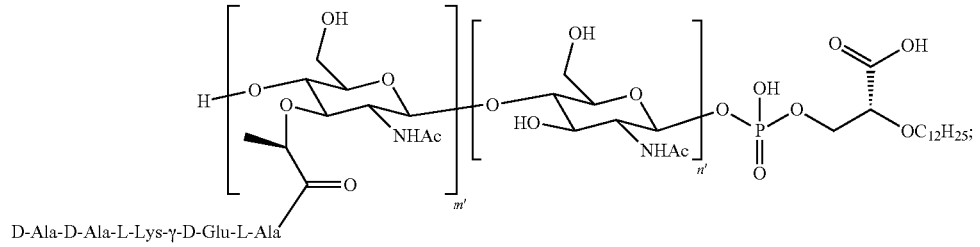
(j)
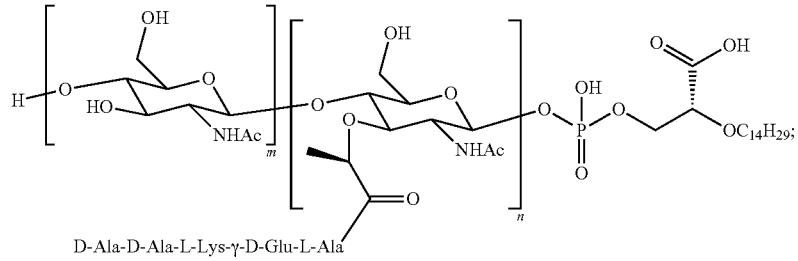
(k)

-continued
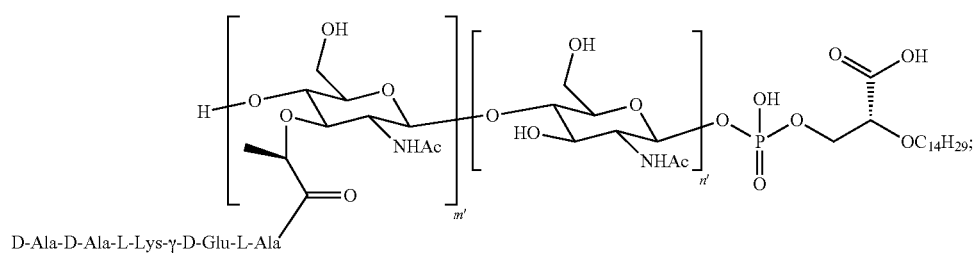
(l)
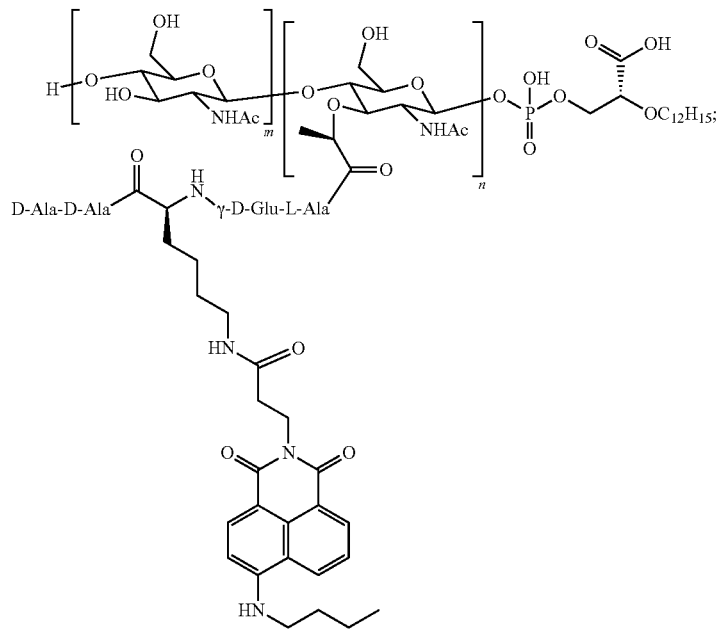
(m)
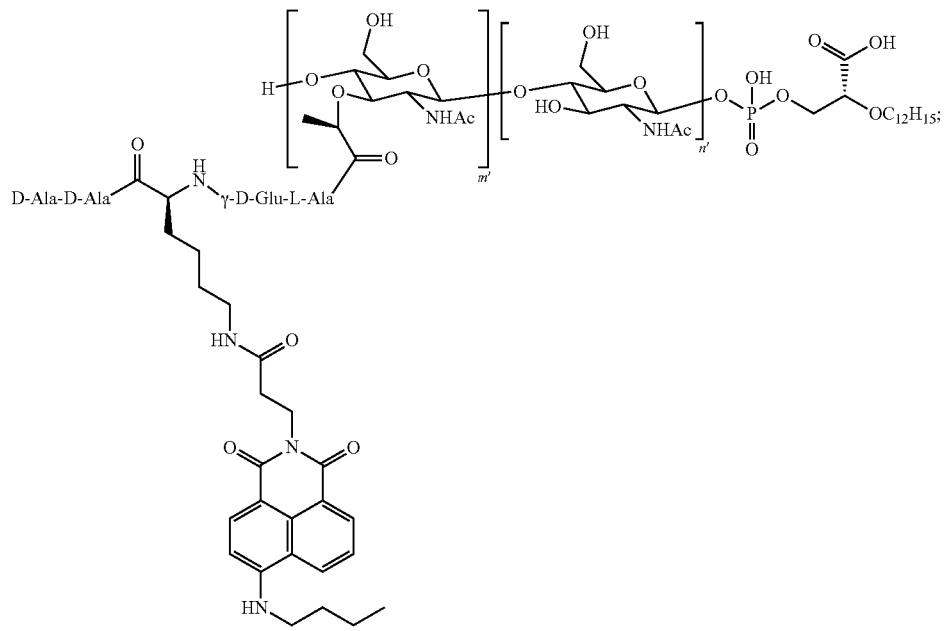
(n)

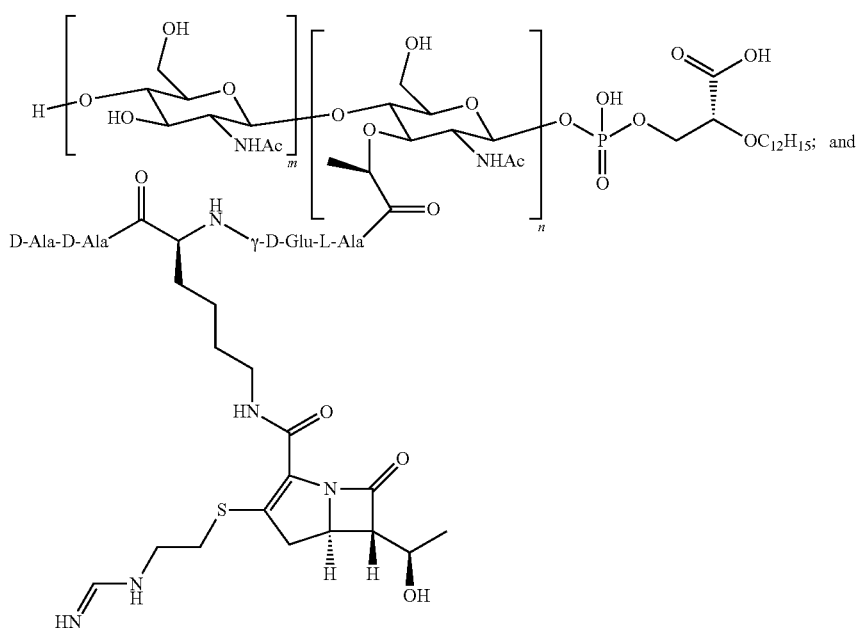

(o)

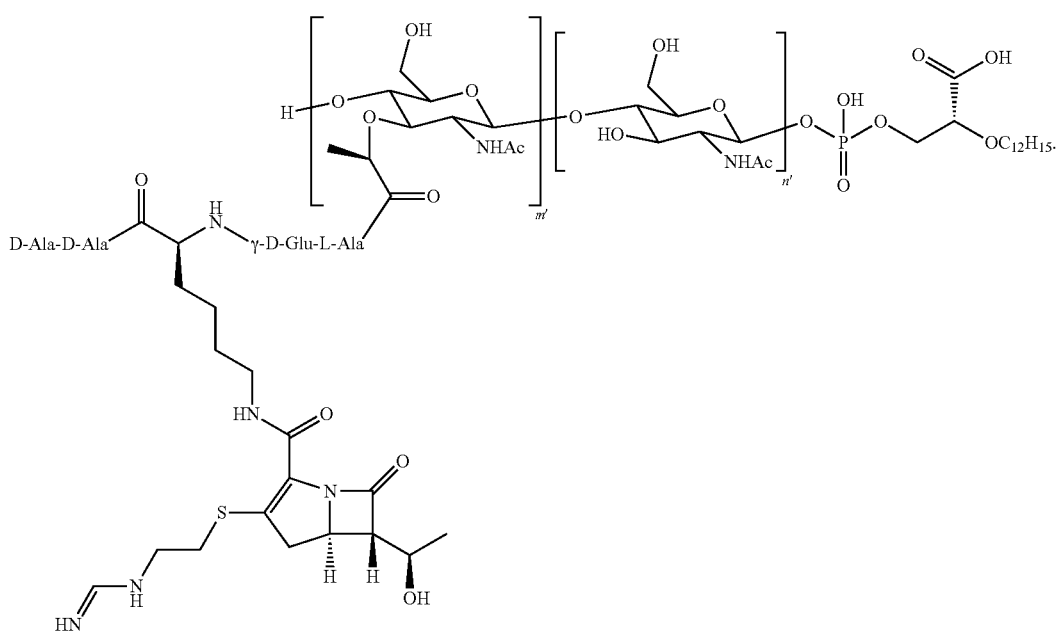

(p)

14. A pharmaceutical formulation comprising one or both of a compound of formula Ia and a compound of formula Ib as described in claim 1 and a pharmaceutically acceptable excipient, diluent or carrier.

15. A method of determining antimicrobial resistance of a microbial infection in a sample in vitro, the method comprising the steps of:

(A) contacting the sample with an antimicrobial to provide an antimicrobial sample;

(B) contacting the antimicrobial sample after a period of time with a compound of formula Ia and/or formula Ib as described in claim 1 where $R_8$ is a fluorescent group, or a pharmaceutically acceptable salt, solvate or prodrug thereof; and (C) detecting fluorescence produced by the fluorescent group upon exposure to a light source, wherein detection of fluorescence is used to determine antimicrobial resistance.

16. The method according to claim 15, wherein the method is conducted in parallel or series, such that multiple samples are subjected to steps (A) to (C) with a plurality of individual antimicrobials and/or combinations of antimicrobials to determine the antimicrobial resistance profile of the microbial infection.

17. A method of determining an effective dose of one or more antimicrobial agents to kill a microorganism, the method comprising the steps of:

(iA) contacting one or more antimicrobial test solutions comprising one or more antimicrobial agents with the microorganism to provide one or more test samples, when there are two or more test samples, the concentration of each of the one or more antimicrobial agents is varied between the two or more antimicrobial test solutions to define a range;

(iB) contacting each of the one or more test samples after a period of time with a compound of formula Ia and/or formula Ib as described in claim 1 where $R_8$ is a fluorescent group, or a pharmaceutically acceptable salt, solvate or prodrug thereof; and (iC) detecting fluorescence produced by the fluorescent group upon exposure to a light source in each of the test samples, wherein detection of fluorescence in a test sample indicates the concentration of the one or more antimicrobial agents in said antimicrobial test solution is not effective, and the lack of detection of fluorescence indicates the concentration of the one or more antimicrobial agents in said antimicrobial test solution is effective, thereby determining the effective dose of the one or more antimicrobial agents.

18. A method of making a compound of formula Ia and/or formula Ib according to claim 1, wherein the compound(s) is obtained and/or obtainable from a chitosan molecule comprising from 9 to 100 sugar units, such as from 10 to 50 sugar units.

19. A method of treatment of a microbial infection comprising administering a pharmaceutically effective amount of one or both of a compound of formula Ia and a compound of formula Ib as described in claim 1 where $R_8$ is a pharmaceutically active moiety, or a pharmaceutically acceptable salt, solvate or prodrug thereof, to a subject in need thereof.

20. A method of detecting a microbial infection in a subject comprising administering a pharmaceutically effective amount of one or both of a compound of formula Ia and a compound of formula Ib as described in claim 1 where $R_8$ is a fluorescent group, or a pharmaceutically acceptable salt, solvate or prodrug thereof, to a subject, subsequently exposing the subject to light irradiation and detecting a microbial infection by the presence of fluorescence.

* * * * *

UNITED STATES PATENT AND TRADEMARK OFFICE
CERTIFICATE OF CORRECTION

| | | |
|---|---|---|
| PATENT NO. | : 12,378,328 B2 | Page 1 of 1 |
| APPLICATION NO. | : 17/267271 | |
| DATED | : August 5, 2025 | |
| INVENTOR(S) | : Liu et al. | |

It is certified that error appears in the above-identified patent and that said Letters Patent is hereby corrected as shown below:

On the Title Page

Item (30), under Foreign Application Priority Data, delete "18, 2019" and insert -- 19, 2018 --.

Signed and Sealed this
Twenty-eighth Day of October, 2025

John A. Squires
*Director of the United States Patent and Trademark Office*